US008568980B2

(12) United States Patent
Ozelius et al.

(10) Patent No.: US 8,568,980 B2
(45) Date of Patent: Oct. 29, 2013

(54) NUCLEIC ACIDS, METHODS AND KITS FOR THE DIAGNOSIS OF DYT6 PRIMARY TORSION DYSTONIA

(75) Inventors: Laurie Ozelius, White Plains, NY (US); Susan Bressman, Englewood, NJ (US)

(73) Assignees: Mount Sinai School of Medicine, New York, NY (US); Beth Israel Medical Center, New York, NY (US)

(*) Notice: Subject to any disclaimer, the term of this patent is extended or adjusted under 35 U.S.C. 154(b) by 0 days.

(21) Appl. No.: 12/694,908

(22) Filed: Jan. 27, 2010

(65) Prior Publication Data

US 2011/0020802 A1    Jan. 27, 2011

Related U.S. Application Data

(60) Provisional application No. 61/147,524, filed on Jan. 27, 2009.

(51) Int. Cl.
*C07H 21/04*    (2006.01)
*C12Q 1/68*    (2006.01)

(52) U.S. Cl.
USPC ....... 435/6.11; 435/6.12; 435/91.2; 536/23.1; 536/24.3

(58) Field of Classification Search
None
See application file for complete search history.

(56) References Cited

U.S. PATENT DOCUMENTS 5,541,308 A * 7/1996 Hogan et al. ............... 536/23.1

FOREIGN PATENT DOCUMENTS

WO    WO 99/52942    * 10/1999

OTHER PUBLICATIONS

Winn-Deen, Molecular Diagnostics, 1998, vol. 3, pp. 217-222.*
Pennisi, Science, 1998; 281 (5384):1787-1789.*
Hacker, Gut, 1997, vol. 40, pp. 623-627.*
Almasy, L. et al., "Idiopathic Torsion Dystonia Linked to Chromosome 8 in Two Mennonite Families", Ann. Neurol., vol. 42, pp. 670-673, 1997.
Bessiere, Damien et al., "Structure-Function Analysis of the THAP Zinc Finger of THAP1, a Large C2CH DNA-binding Module Linked to Rb/E2F Pathways", J. Biol. Chem., vol. 283, pp. 4352-4363, 2008.
Blanchard, Arnaud et al., "DYT6 Dystonia: Review of the Literature and Creation of the UMD Locus-Specific Database (LSDB) for Mutations in the THAP1 Gene", Hum. Mutat., vol. 00, pp. 1-12, 2011.
Blanchard, Arnaud et al., "Singular DYT6 Phenotypes in Association with New THAP1 Frameshift Mutations", Movement Disorders, vol. 26, pp. 1775-1777, 2011.
Bonetti, Monica. et al., "Mutation Screening of the DYT6/THAP1 Gene in Italy", Movement Disorders, vol. 24, pp. 2424-2427, 2009.
Bragg, Cristopher D., et al., "Molecular pathways in dystonia", Neurobiology of Disease , vol. 42, pp. 136-147, 2011.
Bressman, Susan B. et al., "Mutations in THAP1 (DYT6) in early-onset dystonia: a genetic screening study", Lancet Neurol., vol. 8, pp. 441-446, 2009.
Cayrol, Corinne et al., "The THAP—zinc finger protein THAP1 regulates endothelial cell proliferation through modulation of pRB/E2F cell-cycle target genes", Blood, vol. 109, pp. 584-594, 2007.
Cheng, F.B. et al., "Clinical and genetic evaluation of DYT1 and DYT6 primary dystonia in China", Eur. J. Neurol., vol. 18, pp. 497-503, 2011.
Cheng, Fu Bo et al., "THAP1/DYT6 sequence variants in non-DYT1 early-onset primary dystonia in China and their effects on RNA expression", J. Neurol., published online Jul. 29, 2011.
Clot, Fabienne et al., "Screening of the THAP1 gene in patients with early-onset dystonia: myoclonic jerks are part of the dystonia 6 phenotype", Neurogenetics, vol. 12, pp. 87-89, 2011.
Clouaire, Thomas et al., "The THAP domain of THAP1 is a large C2CH module with zinc-dependent sequence-specific DNA-binding activity", Proc. Natl. Acad. Sci. U.S.A., vol. 102, pp. 6907-6912, 2005.
De Carvalho Aguiar, Patricia et al., "Screening of Brazilian Families with Primary Dystonia Reveals a Novel THAP1 Mutation and a De Novo TOR1A GAG Deletion", Movement Disorders, vol. 25, pp. 2854-2857, 2010.
Djarmati, Ana et al., "Mutations in THAP1 (DYT6) and generalised dystonia with prominent spasmodic dysphonia: a genetic screening study", Lancet Neurol., vol. 8, pp. 447-452, 2009.
Duan, Wenzhen et al., "Participation of Prostate Apoptosis Response-4 in Degeneration of Dopaminergic Neurons in Models of Parkinson's Disease", Ann. Neurol., vol. 46, pp. 587-597, 1999.
Fuchs, Tania et al., "Mutations in the THAP1 gene are responsible for DYT6 primary torsion dystonia", Nature Genetics, vol. 41, pp. 286-288, 2009.
Gavarini, Sophie et al., "Direct Interaction between Causative Genes of DYT1 and DYT6 Primary Dystonia", Ann. Neurol., vol. 68, pp. 549-553, 2010.
Groen, Justus L. et al., "DYT6 Dystonia: Mutation Screening, Phenotype, and Response to Deep Brain Stimulation", Movement Disorders, vol. 25, pp. 2420-2427, 2010.

(Continued)

*Primary Examiner* — Sarae Bausch
(74) *Attorney, Agent, or Firm* — Fish & Richardson P.C.

(57) ABSTRACT

The invention relates generally to the THAP1 gene and mutations in this gene, as well as the THAP1 protein and mutations in this protein, that are associated with dystonia. The invention relates to the identification, isolation, cloning and characterization of the DNA sequence corresponding to the wild type and mutant THAP1 genes, as well as isolation and characterization of their transcripts and gene products. The invention further relates to methods and kits useful for detecting mutations in THAP1 that are associated with dystonia, as well as to methods and kits useful for diagnosing dystonia. The present invention also relates to therapies for treating dystonia, including gene therapeutics and protein/antibody based therapeutics.

6 Claims, 4 Drawing Sheets

(56) References Cited

OTHER PUBLICATIONS

Groen, Justus L. et al., "THAP1 Mutations Are Infrequent in Spasmodic Dysphonia", Movement Disorders, vol. 26, pp. 1952-4954, 2011.
Houlden, H. et al., "THAP1 mutations (DYT6) are an additional cause of early-onset dystonia", Neurology 74, pp. 846-850, 2010.
Jech, Robert et al., "DYT 6—A Novel THAP1 Mutation With Excellent Effect on Pallidal DBS", Movement Disorders, vol. 26, pp. 924-925, 2011.
Kaiser, Frank J. et al, "The Dystonia Gene DYT1 Is Repressed by the Transcription Factor THAP1 (DYT6)", Ann. Neurol., vol. 68, pp. 554-559, 2010.
Kramer, P. L. et al., "The DYT I Gene on 9q34 Is Responsible for Most Cases of Early Limb-Onset Idiopathic Torsion Dystonia in Non-Jews", Am. J. Hum. Genet., vol. 55, pp. 468-475, 1994.
Lohmann, Katja et al., "Identification and functional analysis of novel THAP1 mutations", Eur. J. Hum. Gen., pp. 1-5, 2011.
Mazars, Raoul et al., "The THAP-Zinc Finger Protein THAP1 Associates with Coactivator HCF-1 and O-GlcNAc Transferase", J. Biol. Chem., vol. 285, pp. 13364-13371, 2010.
Müller, Ulrich, "A Molecular Link Between Dystonia 1 and Dystonia 6?", Amer. Neurol., vol. 68, pp. 418-420, 2010.
Osmanovic, Alma et al., "Truncating Mutations in THAP1 Define the Nuclear Localization Signal", Movement Disorders, vol. 26, pp. 1565-1567, 2011.
Ozelius, Laurie J. and Bressman, Susan B., "THAP1: Role in focal dystonia?", Neurology, vol. 74, p. 192-193, 2010.
Ozelius, Laurie J. and Bressman, Susan B., "Genetic and clinical features of primary torsion dystonia", Neurobiology of Disease, vol. 42, pp. 127-135, 2011.
Paisan-Ruiz, Coro et al., "Identification of a Novel THAP1 Mutation at R29 Amino-acid Residue in Sporadic Patients with Early-Onset Dystonia", Movement Disorders, vol. 24, pp, 2428-2443, 2009.
Panov, Fedor et al., "Pallidal deep brain stimulation for DYT6 dystonia", J. Neurol. Neurosurg. Psych., pp. 1-7, Published online Sep. 23, 2011.
Roussigne, Myriam et al., "THAP1 is a nuclear proapoptotic factor that links prostate-apoptosis-response-4 (Par-4) to PML nuclear bodies", Oncogene, vol. 22, pp. 2432-2442, 2003.
Roussigne, Myriam et al., "The THAP domain: a novel protein motif with similarity to the DNA-binding domain of P element transposase", Trends Biochem. Sci., vol. 28, pp. 66-69, 2003.
Saunders-Pullman, Rachel et al., "Narrowing the DYT6 Dystonia Region and Evidence for Locus Heterogeneity in the Amish-Mennonites", Am. J. Med. Genet. Part A, vol. 143A, pp. 2098-2105, 2007.
Schneider, Susanne A. et al., "Homozygous THAP1 Mutations as Cause of Early-Onset Generalized Dystonia", Movement Disorders, vol. 26, pp. 858-861, 2011.
Sengel, Cem et al, "Dimerization of the DYT6 dystonia protein, THAP1, requires resides within the coiled-coil domain", J. Neurochem., vol. 118, pp. 1087-1100, 2011.
Söhn, Anne S. et al., "Prevalence of THAP1 Sequence Variants in German Patients with Primary Dystonia", Movement Disorders vol. 25, pp. 1982-1986, 2010.
Song, Wei et al., "Novel THAP1 gene mutations in patients with primary dystonia from Southwest China", J. Neurol. Sci., vol. 309, pp. 63-67, 2011.
Xiao, J. et al., "Novel *THAP1* sequence variants in primary dystonia", Neurology, vol. 74, p. 229-238, 2010.
Xiao, Jianfeng et al., "The C.-237_236GA>TT THAP1Sequence Variant Does Not Increase Risk for Primary Dystonia", Movement Disorders, vol. 26, pp. 549-552, 2011.
Zittel, Simone et al., "Clinical Neuroimaging and Electrophysiological Assessment of Three DYT6 Dystonia Families", Movement Disorders vol. 25, pp. 2405-2412, 2010.
de Carvalho Aguiar, Patricia M., and Ozelius, Laurie J., "Classification and genetics of dystonia", Lancet Neurology, vol. 1, pp. 316-325, 2002.
Ozelius, Laurie J., et al., "The early-onset torsion dystonia gene (DYT1) encodes an ATP-binding protein", Nature Genetics, vol. 17, pp. 40-48, 1997.

\* cited by examiner

NUCLEIC ACIDS, METHODS AND KITS FOR THE DIAGNOSIS OF DYT6 PRIMARY TORSION DYSTONIA

RELATED APPLICATIONS

The present application claims the benefit of U.S. Provisional Patent Application Ser. No. 61/147,524, filed Jan. 27, 2009, which is herein incorporated by reference in its entirety.

STATEMENT REGARDING FEDERALLY SPONSORED RESEARCH OR DEVELOPMENT

This invention was made with government support under grant number NS26636 awarded by the National Institutes of Health. The government has certain rights in the invention.

SEQUENCE LISTING

The instant application contains a Sequence Listing which has been submitted via EFS-Web and is hereby incorporated by reference in its entirety. Said ASCII copy, created on Sep. 23, 2010, is named 27527-0061001.txt, and is 86,894 bytes in size.

FIELD OF THE INVENTION

The present invention relates generally to the THAP1 gene and mutations in this gene, as well as the THAP1 protein and mutations in this protein, that are associated with dystonia. The invention relates to the identification, isolation, cloning and characterization of the DNA sequence corresponding to the wild type and mutant THAP1 genes, as well as isolation and characterization of their transcripts and gene products. The invention further relates to methods and kits useful for detecting mutations in THAP1 that are associated with dystonia, as well as to methods and kits useful for diagnosing dystonia. The present invention also relates to therapies for treating dystonia, including gene therapeutics and protein/antibody based therapeutics.

BACKGROUND OF THE INVENTION

The citation and/or discussion of cited references in this section and throughout the specification is provided merely to clarify the description of the present invention and is not an admission that any such reference is "prior art" to the present invention.

Dystonia is characterized by twisting movements and abnormal postures (Fahn, S. *Adv. Neurol.* (1988) 50: 1-8). At least 15 different types of dystonia can be distinguished genetically, most of which are inherited in an autosomal dominant (AD) manner with reduced penetrance.

DYT1, 2, 4, 6, 7 and 13, comprise primary forms, where dystonia is the only neurologic feature (de Carvalho Aguiar, P. M. and Ozelius, L. J., *Lancet Neurol.* (2002) 1: 316-25). The genetic basis for only one of these, DYT1, responsible for most cases of early onset generalized dystonia, has been identified (Ozelius, L. J. et al., *Nat. Genet.* (1997) 17: 40-8).

DYT6 is dominantly inherited with penetrance of about 60% independent of gender. It is characterized by an average onset age of 16.1 years, cranial or cervical presentation in about half of the cases and frequent progression to involve multiple body regions. First mapped to a 40cM (peri-centromeric) region on chromosome 8 in two Amish-Mennonite families (M and C) (Almasy, L. et al., *Ann. Neurol.* (1997) 42: 670-3), an additional Amish-Mennonite family (R) was shown to share the DYT6 disease haplotype and all three families were descended from several "Old Order Amish" ancestral pairs (Sanders-Pullman, R. et al., *Am. J. Med. Genet. A* (2007) 143A: 2098-105). The linked region was narrowed to 23cM between markers D8S2317 and D8S2323; this region contains ~120 genes (March 2006 UCSC human genome assembly. genome.ucsc.edu) (Sanders-Pullman, R. et al., *Am. J. Med. Genet. A* (2007) 143A: 2098-105).

SUMMARY OF THE INVENTION

In one embodiment, the invention is directed to an isolated THAP1 nucleic acid. In some embodiments, the invention is directed to an isolated THAP1 nucleic acid that encodes a THAP1 peptide comprising the amino acid sequence of SEQ ID NO: 12, SEQ ID NO: 13, SEQ ID NO: 15, SEQ ID NO: 16, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, or SEQ ID NO: 85. In some embodiments, the isolated THAP1 nucleic acid comprises the sequence of SEQ ID NO: 2, SEQ ID NO: 3, SEQ ID NO: 5, SEQ ID NO: 6, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, or SEQ ID NO: 68. In some embodiments, the isolated THAP1 nucleic acid encodes a THAP1 peptide comprising the amino acid sequence of SEQ ID NO: 12. In some embodiments, the isolated THAP1 nucleic acid that encodes a THAP1 peptide comprising the amino acid sequence of SEQ ID NO: 12 includes the sequence of SEQ ID NO: 2. In some embodiments, the isolated THAP1 nucleic acid that encodes a THAP1 peptide comprising the amino acid sequence of SEQ ID NO: 12 includes the sequence of SEQ ID NO: 5.

In one embodiment, the invention is directed to an isolated THAP1 nucleic acid, wherein the nucleic acid encodes a THAP1 peptide comprising the amino acid sequence of SEQ ID NO: 13. In some embodiments, the isolated THAP1 nucleic acid that encodes a THAP1 peptide comprising the amino acid sequence of SEQ ID NO: 13 includes the sequence of SEQ ID NO: 3. In some embodiments, the isolated THAP1 nucleic acid that encodes a THAP1 peptide comprising the amino acid sequence of SEQ ID NO: 13 includes the sequence of SEQ ID NO: 6.

In one embodiment, the invention is directed to an isolated THAP1 nucleic acid, wherein the nucleic acid encodes a THAP1 peptide comprising the amino acid sequence of SEQ ID NO: 15. In some embodiments, an isolated THAP1 nucleic acid that encodes a THAP1 peptide comprising the amino acid sequence of SEQ ID NO: 15 includes the sequence of SEQ ID NO: 2. In some embodiments, an isolated THAP1 nucleic acid that encodes a THAP1 peptide comprising the amino acid sequence of SEQ ID NO: 15 includes the sequence of SEQ ID NO: 5.

In one embodiment, the invention is directed to an isolated THAP1 nucleic acid, wherein the nucleic acid encodes a THAP1 peptide comprising the amino acid sequence of SEQ ID NO: 16. In some embodiments, an isolated THAP1 nucleic acid that encodes a THAP1 peptide comprising the amino acid sequence of SEQ ID NO: 16 includes the sequence of SEQ ID NO: 3. In some embodiments, an isolated THAP1 nucleic acid that encodes a THAP1 peptide comprising the amino acid sequence of SEQ ID NO: 16 includes the sequence of SEQ ID NO: 6.

In one embodiment, the invention is directed to an isolated nucleic acid that includes one or more of the following THAP1 mutations: a c.85C>T mutation, a c.86G>C mutation, a c.241T>C mutation, a c.266A>G mutation, c.115G>A mutation, c.460delC mutation, a c.134_135insGGGTT; 137_139delAAC mutation, a c.161G>A mutation, a c.1A>G mutation, a c.61T>A mutation, a c.67C>T mutation, a c.36C>A mutation, a c.2delT mutation, a c.65T>C mutation, a c.140C>T mutation, a c.392-394delTTT mutation, a c.11C>T mutation, a c.580T>C mutation, a c.424A>G mutation, a c.250-251delAC mutation, and a c.505C>T mutation as compared to wild type THAP1 DNA (e.g., SEQ ID NO: 4).

In one embodiment, the invention is directed to an isolated THAP1 peptide. In some embodiments, an isolated THAP1 peptide includes the sequence of SEQ ID NO: 12, SEQ ID NO: 13, SEQ ID NO: 15, SEQ ID NO: 16, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, or SEQ ID NO: 85.

In some embodiments, the invention is directed to an isolated THAP1 peptide that comprises the sequence of SEQ ID NO: 12. In some embodiments, the invention is directed to an isolated THAP1 peptide, wherein the THAP1 peptide comprises the sequence of SEQ ID NO: 13. In some embodiments, the invention is directed to an isolated THAP1 peptide, wherein the THAP1 peptide comprises the sequence of SEQ ID NO: 15. In some embodiments, the invention is directed to an isolated THAP1 peptide, wherein the THAP1 peptide comprises the sequence of SEQ ID NO: 16.

In one embodiment, the invention is directed to an isolated THAP1 peptide, wherein the THAP1 peptide comprises one or more of the following THAP1 mutations: a p.R29X mutation, a p.R29P mutation, a p.F81L mutation, a p.K89R mutation, a p.A39T mutation, a p.Q154fs18 mutation, a p.F45fs73 mutation, a p.C54Y mutation, a p.S21T mutation, a p.H23Y mutation, a p.N12K mutation, a p.F22S mutation, a p.P47L mutation, a p.ΔF132 mutation, a p.S4F mutation, a p.S194P mutation, a p.T142A mutation, a p.T84X mutation (where X denotes a stop codon), and a p.R169X mutation (where X denotes a stop codon) as compared to a wild type THAP1 protein (e.g., SEQ ID NO: 11).

In one embodiment, the invention is directed to an expression construct. In some embodiments, the invention is directed to an expression construct that includes a promoter operably linked to one or more isolated THAP1 nucleic acids that encode a THAP1 peptide comprising the amino acid sequence of SEQ ID NO: 12, SEQ ID NO: 13, SEQ ID NO: 15, SEQ ID NO: 16, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, or SEQ ID NO: 85.

In some embodiments, the expression construct includes an isolated nucleic acid that encodes a THAP1 peptide comprising the amino acid sequence of SEQ ID NO: 12, wherein the nucleic acid is operably linked to a promoter. In some embodiments, the expression construct includes an isolated nucleic acid that encodes a THAP1 peptide comprising the amino acid sequence of SEQ ID NO: 13, wherein the nucleic acid is operably linked to a promoter. In some embodiments, the expression construct includes an isolated nucleic acid that encodes a THAP1 peptide comprising the amino acid sequence of SEQ ID NO: 15, wherein the nucleic acid is operably linked to a promoter. In some embodiments, the expression construct includes an isolated nucleic acid that encodes a THAP1 peptide comprising the amino acid sequence of SEQ ID NO: 16, wherein the nucleic acid is operably linked to a promoter.

In one embodiment, the invention is directed to an expression construct that includes an isolated nucleic acid that includes one or more of the following THAP1 mutations: a c.85C>T mutation, a c.86G>C mutation, a c.241T>C mutation, a c.266A>G mutation, c.115G>A mutation, c.460delC mutation, a c.134_135insGGGTT;137_139delAAC mutation, a c.161G>A mutation, a c.1A>G mutation, a c.61T>A mutation, a c.67C>T mutation, a c.36C>A mutation, a c.2delT mutation, a c.65T>C mutation, a c.140C>T mutation, a c.392-394delTTT mutation, a c.11C>T mutation, a c.580T>C mutation, a c.424A>G mutation, a c.250-251delAC mutation, and a c.505C>T mutation as compared to a wild type THAP1 DNA (e.g., SEQ ID NO: 4).

In one embodiment, the invention is directed to an isolated cell transfected with an isolated THAP1 nucleic acid. In some embodiments, the invention is directed to an isolated cell transfected with one or more isolated THAP1 nucleic acid that encodes a THAP1 peptide comprising the amino acid sequence of SEQ ID NO: 12, SEQ ID NO: 13, SEQ ID NO: 15, SEQ ID NO: 16, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, or SEQ ID NO: 85.

In some embodiments, the invention is directed to an isolated cell transfected with an isolated THAP1 nucleic acid that encodes a THAP1 peptide comprising the amino acid sequence of SEQ ID NO: 12. In some embodiments, the invention is directed to an isolated cell transfected with an isolated THAP1 nucleic acid that encodes a THAP1 peptide comprising the amino acid sequence of SEQ ID NO: 13. In some embodiments, the invention is directed to an isolated cell transfected with an isolated THAP1 nucleic acid that encodes a THAP1 peptide comprising the amino acid sequence of SEQ ID NO: 15. In some embodiments, the invention is directed to an isolated cell transfected with an isolated THAP1 nucleic acid that encodes a THAP1 peptide comprising the amino acid sequence of SEQ ID NO: 16. In some embodiments, the invention is directed to an isolated cell transfected with an isolated THAP1 nucleic acid that includes one or more of the following THAP1 mutations: a c.85C>T mutation, a c.86G>C mutation, a c.241T>C mutation, a c.266A>G mutation, a c.115G>A mutation, a c.460delC mutation, a c.134_135insGGGTT;137_139delAAC mutation, a c.161G>A mutation, a c.1A>G mutation, a c.61T>A mutation, a c.67C>T mutation, a c.36C>A mutation, a c.2delT mutation, a c.65T>C mutation, a c.140C>T mutation, a c.392-394delTTT mutation, a c.11C>T mutation, a c.580T>C mutation, a c.424A>G mutation, a c.250-251delAC mutation, and a c.505C>T mutation.

In one embodiment, the invention is directed to a method of detecting the presence of a THAP1 mutation in a biological sample from a subject, comprising: obtaining a biological sample comprising DNA or RNA from a subject; if the sample comprises RNA, producing cDNA from the RNA contained in the biological sample; contacting the biological sample with primer pairs that allow for specific amplification of all or part of the THAP1 DNA or cDNA, under conditions permitting hybridization of the primers to the DNA; amplifying the THAP1 DNA or cDNA; and comparing the amplified products obtained from the subject to the amplified products obtained with a normal control biological sample, whereby a difference between the product from the subject and the product from the normal sample indicates the presence of a THAP1 mutation in the subject. In some embodiments, the primer pairs use in this method are selected from SEQ ID NO: 20 and SEQ ID NO: 21; SEQ ID NO: 22 and SEQ ID NO: 23; SEQ ID NO: 24 and SEQ ID NO: 25; SEQ ID NO: 26 and SEQ ID NO: 27; SEQ ID NO: 28 and SEQ ID NO: 29; and SEQ ID NO: 30 and SEQ ID NO: 31. In some embodiments, the THAP1 DNA is amplified by PCR or real-time PCR. In some embodiments, the THAP1 mutation includes one or more of the following THAP1 mutations: a c.134_135insGGGTT;137_139delAAC mutation, a c.241T>C mutation, a c.85>T mutation, a c.86G>C mutation, a c.266A>G mutation, a c.115G>A mutation, a c.460delC mutation, a c.161G>A mutation, a c.1A>G mutation, a c.61T>A mutation, a c.67C>T mutation, a c.36C>A mutation, a c.2delT mutation, a c.65T>C mutation, a c.140C>T mutation, a c.392-394delTTT mutation, a c.11C>T mutation, a c.580T>C mutation, a c.424A>G mutation, a c.250-251delAC mutation, and a c.505C>T mutation. In some embodiments, the method further includes digesting the DNA or cDNA with at least one restriction enzyme and comparing the restriction fragments of the amplified product with the restriction fragments obtained from the amplification of a normal control biological sample, whereby a difference between the restriction fragments from the subject and the restriction fragments from the normal sample indicates the presence of a THAP1 mutation in the subject.

In one embodiment, the invention is directed to a method of detecting the presence of a THAP1 mutation in a biological sample from a subject, comprising: obtaining a biological sample comprising RNA from a subject; producing cDNA from RNA contained in the biological sample; contacting the cDNA with specific oligonucleotides permitting the amplification of all or part of the transcript of the THAP1 gene, under conditions permitting hybridization of the primers with the cDNA; amplifying the cDNA; and comparing the amplified products obtained to the amplified products obtained with a normal control biological sample, whereby a difference between the product from the subject and the product from the normal sample indicates the presence of a THAP1 mutation in the subject. In some embodiments, the cDNA is amplified by PCR or real-time PCR. In some embodiments, the PCR or real-time PCR is performed with a primer pair selected from SEQ ID NO: 20 and SEQ ID NO: 21; SEQ ID NO: 22 and SEQ ID NO: 23; SEQ ID NO: 24 and SEQ ID NO: 25; SEQ ID NO: 26 and SEQ ID NO: 27; SEQ ID NO: 28 and SEQ ID NO: 29; and SEQ ID NO: 30 and SEQ ID NO: 31. In some embodiments, the THAP1 mutation includes one or more of the following THAP1 mutations: a c.134_135insGGGTT; 137_139delAAC mutation, a c.241T→C mutation, a c.85>T mutation, a c.86G>C mutation, a c.266A>G mutation, a c.115G>A mutation, a c.460delC mutation, a c.161G>A mutation, a c.1A>G mutation, a c.61T>A mutation, a c.67C>T mutation, a c.36C>A mutation, a c.2delT mutation, and a c.65T>C mutation, a c.140C>T mutation, a c.392-394delTTT mutation, a c.11C>T mutation, a c.580T>C mutation, a c.424A>G mutation, a c.250-251delAC mutation, and a c.505C>T mutation.

In one embodiment, the invention is directed to a method for detecting the presence of a THAP1 mutation in a biological sample, comprising: obtaining a biological sample from a subject that comprises DNA or RNA; if the sample comprises RNA, producing cDNA from the RNA contained in the biological sample; digesting the DNA or cDNA with at least one restriction enzyme; and comparing the restriction fragments of the amplified product with the restriction fragments obtained from the amplification of a normal control biological sample, whereby a difference between the restriction fragments from the subject and the restriction fragments from the normal sample indicates the presence of a THAP1 mutation in the subject. In some embodiments, the method also includes contacting the DNA or cDNA with specific oligonucleotides permitting the amplification of all or part of the THAP1 gene or transcript of the THAP1 gene prior to digesting the DNA or cDNA with at least one restriction enzyme. In some embodiments, the restriction enzyme is DraI or SspI.

In one embodiment, the invention is directed to a method for detecting the presence of a mutation in THAP1 in a nucleic acid sample, the method comprising: obtaining a biological sample from a subject that comprises DNA or RNA; if the sample comprises RNA, producing cDNA from the RNA contained in the biological sample; contacting the DNA or cDNA with an oligonucleotide, wherein the oligonucleotide comprises the sequence of SEQ ID NO: 7 or comprises a sequence that is complementary to the sequence of SEQ ID NO: 7; and determining whether the oligonucleotide binds to the DNA or cDNA, wherein the absence of binding indicates the presence of a mutation in a THAP1 gene or transcript of the subject.

In one embodiment, the invention is directed to a method for detecting the presence of a mutation in THAP1 in a nucleic acid sample, the method comprising: obtaining a biological sample from a subject that comprises DNA or RNA; if the sample comprises RNA, producing cDNA from the RNA contained in the biological sample; contacting the DNA or cDNA with an oligonucleotide, wherein the oligonucleotide comprises the sequence of SEQ ID NO: 8 or comprises a sequence that is complementary to the sequence of SEQ ID NO: 8; and determining whether the oligonucleotide binds to the DNA or cDNA, wherein the absence of binding indicates the presence of a mutation in a THAP1 gene or transcript of the subject.

In one embodiment, the invention is directed to a method for detecting the presence of a mutation in THAP1 in a nucleic acid sample, the method comprising: obtaining a biological sample from a subject that comprises DNA or RNA; if the sample comprises RNA, producing cDNA from the RNA contained in the biological sample; contacting the DNA or cDNA with an oligonucleotide, wherein the oligonucleotide comprises the sequence of SEQ ID NO: 9 or comprises a sequence that is complementary to the sequence of SEQ ID NO: 9; and determining whether the oligonucleotide binds to the DNA or cDNA, wherein the absence of binding indicates the presence of a mutation in a THAP1 gene or transcript of the subject.

In one embodiment, the invention is directed to a method for detecting the presence of a mutation in THAP1 in a nucleic acid sample, the method comprising: obtaining a biological sample from a subject that comprises DNA or RNA; if the sample comprises RNA, producing cDNA from the RNA contained in the biological sample; contacting the DNA or cDNA with an oligonucleotide, wherein the oligonucleotide comprises the sequence of SEQ ID NO: 10 or comprises a sequence that is complementary to the sequence of SEQ ID NO: 10; and determining whether the oligonucleotide binds to the DNA or cDNA, wherein the absence of binding indicates the presence of a mutation in a THAP1 gene or transcript of the subject.

In one embodiment, the invention is directed to a kit for detecting the presence of a THAP1 mutations in a biological sample. In some embodiments, a kit for detecting the presence of a THAP1 mutation in a biological sample includes an isolated THAP1 nucleic acid that encodes a THAP1 peptide comprising the amino acid sequence of SEQ ID NO: 12, SEQ ID NO: 13, SEQ ID NO: 15, SEQ ID NO: 16, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, or SEQ ID NO: 85. In some embodiments, the kit further comprises a primer pair selected from the group consisting of: SEQ ID NO: 20 and SEQ ID NO: 21; SEQ ID NO: 22 and SEQ ID NO: 23; SEQ ID NO: 24 and SEQ ID NO: 25; SEQ ID NO: 26 and SEQ ID NO: 27; SEQ ID NO: 28 and SEQ ID NO: 29; and SEQ ID NO: 30 and SEQ ID NO: 31.

In some embodiments, a kit for detecting the presence of a THAP1 mutation in a biological sample includes a nucleic acid that includes the sequence of SEQ ID NO: 2, SEQ ID NO: 5, or SEQ ID NO: 9. In some embodiments, a kit for detecting the presence of a THAP1 mutation in a biological sample includes a nucleic acid that includes the sequence of SEQ ID NO: 3, SEQ ID NO: 6 or SEQ ID NO: 10. In some embodiments, a kit for detecting the presence of a THAP1 mutation in a biological sample includes amplification primers selected from the group consisting of: SEQ ID NO: 20 and SEQ ID NO: 21; SEQ ID NO: 22 and SEQ ID NO: 23; SEQ ID NO: 24 and SEQ ID NO: 25; SEQ ID NO: 26 and SEQ ID NO: 27; SEQ ID NO: 28 and SEQ ID NO: 29; and SEQ ID NO: 30 and SEQ ID NO: 31. In some embodiments, a kit for detecting the presence of a THAP1 mutation in a biological sample includes sequence determination primers selected from the group consisting of: SEQ ID NO: 20 and SEQ ID NO: 21; SEQ ID NO: 22 and SEQ ID NO: 23; SEQ ID NO: 24 and SEQ ID NO: 25; SEQ ID NO: 26 and SEQ ID NO: 27; SEQ ID NO: 28 and SEQ ID NO: 29; and SEQ ID NO: 30 and SEQ ID NO: 31. In some embodiments, a kit for detecting the presence of a THAP1 mutation in a biological sample includes an antibody that binds to a wild-type THAP1 protein comprising the amino acid sequence of SEQ ID NO: 11, but not to a mutant THAP1 protein comprising the amino acid sequence of SEQ ID NO: 12 or SEQ ID NO: 13. In some embodiments, a kit for detecting the presence of a THAP1 mutation in a biological sample includes an antibody that binds to a mutant THAP1 protein comprising the amino acid sequence of SEQ ID NO: 12, but not to a wild-type THAP1 protein comprising the amino acid sequence of SEQ ID NO: 11. In some embodiments, a kit for detecting the presence of a THAP1 mutation in a biological sample includes an antibody that binds to a mutant THAP1 protein comprising the amino acid sequence of SEQ ID NO: 13, but not to a wild-type THAP1 protein comprising the amino acid sequence of SEQ ID NO: 11.

In some embodiments, a method for treating dystonia includes administering to a subject a nucleic acid that encodes a THAP1 peptide comprising the amino acid sequence of SEQ ID NO: 11. In some embodiments, a method for treating dystonia includes administering to a subject a THAP1 peptide that comprises the amino acid sequence of SEQ ID NO: 11.

BRIEF DESCRIPTION OF THE DRAWINGS

FIG. 1A shows a DNA sequence alignment of wild type (WT) (bottom) (SEQ ID NO: 90) and Mutant (Mut) (top) (SEQ ID NO: 89) alleles at the site of insertion/deletion in exon 2. Sequence analysis of the THAP1 gene revealed that the inserted pentanucleotide sequence GGGTT occurs in reverse complement orientation (AACCC) 2 bps downstream from the insertion site suggesting that this could serve as a source of the insertion (underlined). Moreover, the 3 bp deletion is contained within this reverse complementary sequence, suggesting that the insertion event preceded the deletion or occurred simultaneously. FIG. 1B shows a schematic representation of the THAP1 protein that depicts the THAP domain (solid black), low-complexity proline rich region (zig zag lines), coiled-coil domain (black diamonds), and nuclear localization signal (white). The exon positions are indicated by brackets and numbers refer to the amino acid sequence. The cross-hatched region on the mutant protein represents the out of frame amino acid sequence of the mutant. FIG. 1C shows a protein sequence from the THAP domain compared across species using ClustalW (SEQ ID NOS 91-107, respectively, in order of appearance). Zinc binding residues are indicated by the bracket labeled "Zn". Four invariant residues necessary for DNA binding are also indicated in bold. The AVPTIF motif (SEQ ID NO: 86), also essential for DNA binding, is shown with a bracket, the F residue of this motif is mutated to an L in family S. The mutation is indicated by an arrow from "F81L".

In FIG. 4A, a Western blot with monoclonal anti-V5 antibody shows the in vitro translated products for in vitro transcribed/translated full-length wild type THAP1 (IVT WT THAP1) and F81L mutant (IVT F81L mutant) proteins. Whole cell lysate of HEK 293T cells transfected with the plasmid expressing the V5 epitope-tagged wild type THAP1 (293T WT THAP1) was used as the positive control, and transcription/translation mix primed with empty expression vector was used as the negative control (IVT Empty Vector). FIG. 4B shows an autoradiogram of electrophoretic mobility shift assay (EMSA) performed with identical amounts of in vitro transcribed/translated products (lanes 2-5, control sample using empty expression vector; lanes 6-9, wild type THAP1; lanes 10-13, F81L mutant) using a radiolabeled THABS probe, in the absence or presence of excess unlabeled THABS oligonucleotides as indicated on the bottom. Anti-THAP1 antibody was used to detect the presence of THAP1 in the complexes. The black arrowhead indicates the THAP1/THABS complex; the white arrowhead indicates the antibody/THAP1/THABS complex. RRL is rabbit reticulocyte lysate primed with empty expression vector.

DETAILED DESCRIPTION

Figure 1:
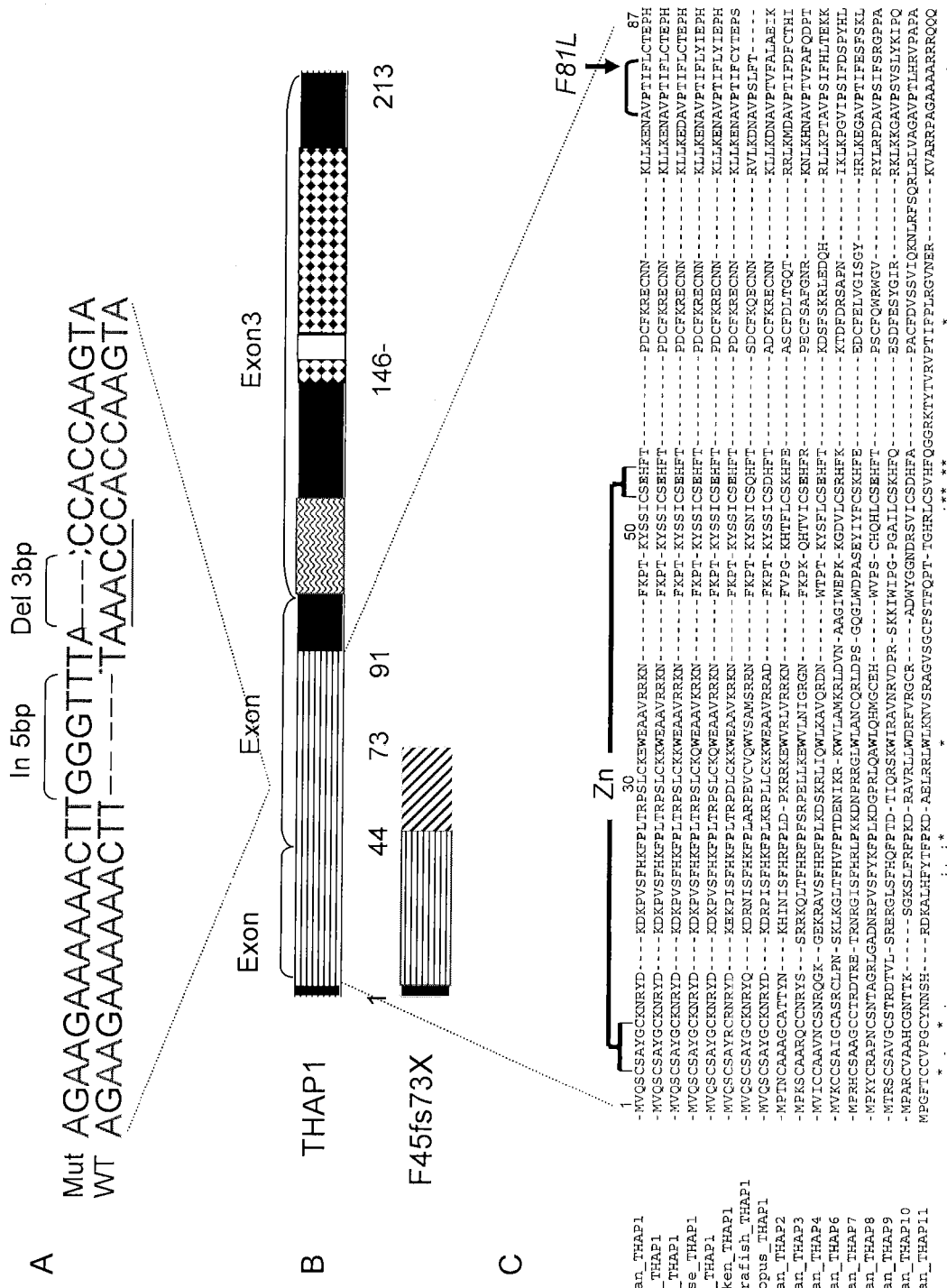
FIG. 1 shows the F45fs73X and F81L mutations identified in THAP1 in individuals with DYT6 dystonia.

The invention relates to mutations in the THAP1 gene, which the inventors of the instant application discovered are associated with dystonia. In particular, the inventors of the instant application discovered that mutations in the THAP1 gene are associated with DYT6 dystonia. As described in more detail in the Examples, a heterozygous 5 bp (GGGTT) insertion followed by a 3 bp deletion (AAC) (c.134_135insGGGTT;137_139delAAC) in exon 2 of the THAP (Thanatos-associated protein) domain containing, apoptosis associated protein 1 (THAP1) gene was found to co-segregate with the disease of dystonia in all affected individuals and obligate carriers in four Amish-Mennonite families (families M, C, W and R), but was not identified in Amish-Mennonite control chromosomes. The mutation causes a frame shift at amino acid position number 44 of the human THAP1 wild-type protein, which corresponds to amino acid position number 44 of SEQ ID NO: 11 (NP_060575), resulting in a premature stop codon at position 73 (F45fs73X; see FIGS. 1A, 1B). Analysis of six single nucleotide polymorphisms (SNPs) in the region of the THAP1 gene in the W and M families confirmed that the F45fs73X mutation is a founder mutation in the Amish-Mennonite population.

A second mutation in exon 2 of the THAP1 gene, a c.241T→C mutation, was found to co-segregate with dystonia in affected individuals in a fifth family (family S) of partial German ancestry, but was not observed in 514 control chromosomes (154 Centre d'Etude du Polymorphisme Humain (CEPH; Center for the Study of Human Polymorphisms), 180 Amish-Mennonite and 190 United Kingdom Caucasian controls). The c.241T→C mutation is a thymine to cytosine mutation at nucleotide position 241 of SEQ ID NO: 4. The c.241T→C mutation replaces a phenylalanine with a leucine at amino acid position number 81, which corresponds to amino acid position 81 of SEQ ID NO: 11 (NP_060575), the human THAP1 wild-type protein. The phenylalanine at amino acid position 81 is located in a highly conserved AVPTIF motif (SEQ ID NO: 86) of the THAP1 protein (FIG. 1C).

The invention is also directed, in part, to mutations in THAP1 as listed in Table 1:

TABLE 1

Mutations in THAP1

| Subject | Ethnicity | Exon | Mutations (SEQ ID NO) | Protein (SEQ ID NO) |
|---|---|---|---|---|
| AE187 | German | Exon 2 | c.85C > T SEQ ID NO: 50 | p.R29X SEQ ID NO: 69 |
| AUS-SP | Australian | Exon 2 | c.85C > T SEQ ID NO: 50 | p.R29X SEQ ID NO: 69 |
| Min5545 | Irish | Exon 2 | c.86G > C SEQ ID NO: 51 | p.R29P SEQ ID NO: 70 |
| S | German/Irish | Exon 2 | c.241T > C SEQ ID NO: 6 | p.F81L SEQ ID NO: 13 |
| AE1573 | Russia | Exon 2 | c.266A > G SEQ ID NO: 52 | p.K89R SEQ ID NO: 71 |
| GUS11075 | Italian | Exon 2 | c.115G > A SEQ ID NO: 53 | p.A39T SEQ ID NO: 72 |
| AE232 | German | Exon 3 | c.460delC SEQ ID NO: 54 | p.Q154fs18 SEQ ID NO: 73 |
| AE189 | German/Irish | Exon 2 | c.134_135insGGGTT; 137_139delAAC SEQ ID NO: 5 | p.F45fs73 SEQ ID NO: 12 |
| GUS17859 | Italian | Exon 2 | c.161G > A SEQ ID NO: 55 | p.C54Y SEQ ID NO: 74 |
| AE714 | Brazil | Exon 1 | c.1A > G SEQ ID NO: 56 | p.? |
| GUS25472 | Italian | Exon 1 | c.61T > A SEQ ID NO: 57 | p.S21T SEQ ID NO: 75 |
| AE1613 | Amish-Mennonite | Exon 1 | c.67C > T SEQ ID NO: 58 | p.H23Y SEQ ID NO: 76 |
| GU25191 | Irish | Exon 1 | c.36C > A SEQ ID NO: 59 | p.N12K SEQ ID NO: 77 |
| AE2719 | Irish | Exon 1 | c.2delT SEQ ID NO: 60 | p.? |
| GUS27111 | Amish-Mennonite | Exon 1 | c.65T > C SEQ ID NO: 61 | p.F22S SEQ ID NO: 78 |
| M | Amish-Mennonite | | c.134_135insGGGTT; 137_139delAAC SEQ ID NO: 5 | p.F45fs73 SEQ ID NO: 12 |
| C | Amish-Mennonite | | c.134_135insGGGTT; 137_139delAAC SEQ ID NO: 5 | p.F45fs73 SEQ ID NO: 12 |
| R | Amish-Mennonite | | c.134_135insGGGTT; 137_139delAAC SEQ ID NO: 5 | p.F45fs73 SEQ ID NO: 12 |
| W | Amish-Mennonite | | c.134_135insGGGTT; 137_139delAAC SEQ ID NO: 5 | p.F45fs73 SEQ ID NO: 12 |
| AE2558 | Amish-Mennonite | | c.134_135insGGGTT; 137_139delAAC SEQ ID NO: 5 | p.F45fs73 SEQ ID NO: 12 |
| AE3048 | Amish-Mennonite | Exon 2 | C.134_135insGGGTT; 137_139delAAC SEQ ID NO: 5 | p.F45fs73 SEQ ID NO: 12 |
| 15855 | | Exon 2 | c.140C > T SEQ ID NO: 62 | p.P47L SEQ ID NO: 79 |

TABLE 1-continued

Mutations in THAP1

| Subject | Ethnicity | Exon | Mutations (SEQ ID NO) | Protein (SEQ ID NO) |
|---|---|---|---|---|
| 19820 | | Exon 3 | c.392-394delTTT SEQ ID NO: 63 | p.ΔF132 (deletes F132 but protein stays in frame) SEQ ID NO: 80 |
| 20149 | | Exon 1 | c.11C > T SEQ ID NO: 64 | p.S4F SEQ ID NO: 81 |
| MIN | Italian, | Exon 3 | c.580T > C | p.S194P |
| 18749 | Portuguese, Irish | | SEQ ID NO: 65 | SEQ ID NO: 82 |
| GUS13411 | Italian | Exon 3 | C.424A > G SEQ ID NO: 66 | p.T142A SEQ ID NO: 83 |
| MIN5175 | Dutch | Exon 2 | C.250-251delAC SEQ ID NO: 67 | p.T84X SEQ ID NO: 84 |
| JANK 4132 | | Exon 3 | c.505C > T SEQ ID NO: 68 | p.R169X SEQ ID NO: 85 |

In Table 1, the number in the description of the mutation is in relation to SEQ ID NO: 4. For example, c.134_135insGGGTT;137_139delAAC refers to a mutation in which there is an insertion of GGGTT between nucleotides 134 and 135 of SEQ ID NO: 4 and a deletion of AAC corresponding to nucleotides 137-139 of SEQ ID NO: 4. Likewise, c.241T>C refers to a mutation in which there is a thymine to cytosine mutation at nucleotide position 241 of SEQ ID NO: 4. In Table 1, the number in the description of the protein is in relation to SEQ ID NO: 11. For example, F81L refers to a phenylalanine to leucine mutation at amino acid position 81 of SEQ ID NO: 11. In Table 1, "p.?" indicates that the mutation affects the start codon so the nature of the protein produced, if any, is unclear.

THAN is a member of a family of cellular factors sharing a highly conserved THAP domain, which is an atypical zinc finger (CysX$_{2-4}$CysX$_{35-53}$CysX$_2$H is (SEQ ID NO: 87)) (Clouaire, T. et al., *Proc. Natl. Acad. Sci. U.S.A.* (2005) 102: 6907-12; Roussigne, M. et al., *Oncogene* (2003) 22: 2432-42; Roussigne, M. et al., *Trends Biochem. Sci.* (2003) 28: 66-9). Associated with its DNA binding domain, THAP1 regulates endothelial cell proliferation via modulation of pRb/E2F cell cycle target genes (Cayrol, C. et al., Blood (2007) 109: 584-94). In addition to the THAP domain at the N-terminus, THAP1 possesses a low complexity, proline rich region, a coiled-coil domain and nuclear localization signal (NLS) at its C-terminus (FIG. 1). In vitro, the C-terminal region of THAP1 interacts with prostate apoptosis response-4 protein (Par-4) (Roussigne, M. et al., *Oncogene* (2003) 22: 2432-42), an effector of cell death linked to prostate cancer and neurodegenerative diseases, including Parkinson's disease (Duan, W. et al., *Ann. Neurol.* (1999) 46: 587-97). THAP1 may recruit Par-4 to specific promoters to modulate transcriptional activation of genes involved in apoptosis (Roussigne, M. et al., *Oncogene* (2003) 22: 2432-42).

Recently, the three-dimensional structure of the THAP domain from human THAP1 was resolved and structure-function relationships were determined (Bessiere, D. et al., *J. Biol. Chem.* (2008) 283: 4352-63). It revealed four Zn-binding residues participating in Zinc finger formation, as well as a number of critical residues for DNA binding (FIG. 1C). Further, a deletion mutant, containing amino acids 1-63, resulted in unfolded protein with no DNA-binding activity. This suggests that the frameshift mutation, F45fs73X, in the Amish-Mennonite families, should be similarly nonfunctional. Moreover, F45fs73X lacks the Cys54 and His57 residues needed for Zn binding and several of the other conserved residues critical for DNA binding: Phe58, Pro78 and the AVPTIF motif (SEQ ID NO: 86) (FIG. 1C). Alanine mutagenesis of each of these residues alone as well as deletion of the AVPTIF motif (SEQ ID NO: 86) is sufficient to abolish the DNA binding activity of THAP1 (Bessiere, D. et al., *J. Biol. Chem.* (2008) 283: 4352-63).

Nucleic Acids and Proteins

In one embodiment, the invention relates to an isolated nucleic acid encoding a THAP1 peptide. As used herein, a "THAP1 peptide" is THAP (Thanatos-associated protein) domain containing, apoptosis associated protein 1. The term "THAP1 peptide" includes a peptide having an amino acid sequence of SEQ ID NO: 11, as well as peptides having an amino acid sequence that has at least 80% sequence identity to SEQ ID NO: 11 over a region of at least 40 amino acids. Preferably, the THAP1 peptide has at least 90%, at least 95%, or at least 99% sequence identity to SEQ ID NO: 11 over a region of at least 40 amino acids.

As used herein, the term "nucleic acid" or "oligonucleotide" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. The term "nucleic acid" or "oligonucleotide" includes, for example, genomic DNA, cDNA, DNA, RNA, and mRNA. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear (e.g., restriction fragments) or circular DNA molecules, plasmids, and chromosomes. In discussing the structure of particular double-stranded DNA molecules, sequences may be described herein according to the normal convention of giving only the sequence in the 5' to 3' direction along the non-transcribed strand of DNA (i.e., the strand having a sequence homologous to the mRNA). A "recombinant DNA molecule" is a DNA molecule that has undergone a molecular biological manipulation.

The sequence of nucleic acids disclosed herein are written according to The International Union of Pure and Applied Chemistry (IUPAC) DNA codes. Specifically, "A" is Adenine; "C" is Cytosine; "G" is Guanine; "T" is Thymine; "U" is Uracil; "R" is any Purine (A or G); "Y" is any Pyrimidine (C, T, or U); "M" is C or A; "K" is T, U, or G; "W" is T, U, or A; "S" is C or G; "B" is C, T, U, or G (not A); "D" is A, T, U, or G (not C); "H" is A, T, U, or C (not G); "V" is A, C, or G (not T, not U); and "N" is any base (A, C, G, T, or U).

As used herein, the term "isolated" means that the referenced material is removed from the environment in which it is normally found. Thus, an isolated biological material can be free of cellular components, i.e., components of the cells in which the material is found or produced. Isolated nucleic acid molecules include, for example, a PCR product, an isolated mRNA, a cDNA, or a restriction fragment. Isolated nucleic acid molecules also include, for example, sequences inserted into plasmids, cosmids, artificial chromosomes, and the like. An isolated nucleic acid molecule is preferably excised from the genome in which it may be found, and more preferably is no longer joined to non-regulatory sequences, non-coding sequences, or to other genes located upstream or downstream of the nucleic acid molecule when found within the genome. An isolated protein may be associated with other proteins or nucleic acids, or both, with which it associates in the cell, or with cellular membranes if it is a membrane-associated protein.

The wild-type nucleic acid encoding for human wild-type THAP1 peptide corresponds to the sequence set forth in SEQ ID NO: 4. GenBank accession number NM_018105.2, which corresponds to SEQ ID NO: 1, is also a nucleic acid that encodes a human wild-type THAP1 peptide; this sequence includes 5' UTR and 3'UTR regions. One of skill in the art will understand that a nucleic acid that is a ribonucleic acid (RNA) will have uracil in place of thymine.

The amino acid sequence for human wild-type THAP1 peptide corresponds to the sequence with GenBank accession number NP_060575, which is SEQ ID NO: 11.

In one embodiment, the invention relates to an isolated nucleic acid that encodes a THAP1 peptide wherein the nucleic acid sequence comprises a c.134_135insGGGTT; 137_139delAAC mutation (e.g., SEQ ID NO: 5). As used herein, "c.134_135insGGGTT;137_139delAAC" refers to a 5 bp (GGGTT) insertion followed by a 3 bp deletion (AAC) in a THAP1 peptide as follows: With reference to SEQ ID NO: 4, the location of the 5bp (GGGTT) insertion is after nucleotide 134 of SEQ ID NO: 4 (see FIG. 1). With reference to SEQ ID NO: 4, the location of the 3 bp deletion (AAC) corresponds to nucleotides 137-139 of SEQ ID NO: 4. That is, the nucleic acid sequence TTTAAACC (SEQ ID NO: 7), which corresponds to nucleotides 133-140 of SEQ ID NO: 4, is mutated to TTGGGTTTAC (SEQ ID NO: 9) in the c.134_135insGGGTT;137_139delAAC mutant.

The c.134_135insGGGTT;137_139delAAC mutation (e.g., SEQ ID NO: 5) causes a frame shift at amino acid position number 44 of the human THAP1 wild-type protein, which corresponds to amino acid position number 44 of SEQ ID NO: 11 (NP 060575), resulting in a premature stop codon at an amino acid that corresponds to position 74 of SEQ ID NO: 11 (NP_060575) (see FIGS. 1A, 1B). This protein mutation is referred to herein as "F45fs73X." SEQ ID NO: 2 is a nucleic acid that comprises the c.134_135insGGGTT;137_139delAAC mutation (e.g., SEQ ID NO: 5) and encodes a peptide that comprises the F45fs73X mutation. In particular, SEQ ID NO: 2 encodes the peptide of SEQ ID NO: 12. Likewise, SEQ ID NO: 5 is a nucleic acid that comprises the c.134_135insGGGTT;137_139delAAC mutation and encodes a peptide that comprises the F45fs73X mutation. In particular, SEQ ID NO: 5 encodes SEQ ID NO: 12.

The present invention relates to nucleic acids of at least 10 nucleotides that comprise TTGGGTTTAC (SEQ ID NO: 9).

In another embodiment, the invention relates to an isolated nucleic acid that encodes a THAP1 peptide wherein the nucleic acid sequence comprises a c.241T→C mutation. As used herein, "c.241T→C" refers to a thymine to cytosine mutation at a nucleotide position that corresponds to nucleotide position 241 of SEQ ID NO: 4. That is, the nucleic acid sequence ATATTTCTT (SEQ ID NO: 8), which corresponds to nucleotides 238-246 of SEQ ID NO: 4, is mutated to ATACTTCTT (SEQ ID NO: 10) in the c.241T→C mutant.

With respect to the human THAP1 wild-type peptide (NP_060575; SEQ ID NO: 11), the c.241T→C mutation replaces a phenylalanine with a leucine at amino acid position 81 of SEQ ID NO: 11. As used herein, "F81L" refers to a phenylalanine to leucine mutation in a protein at an amino acid position that corresponds to amino acid position 81 of SEQ ID NO: 11 (NP_060575).

SEQ ID NO: 3 is a nucleic acid that comprises the c.241T→C mutation and encodes a peptide that comprises the F81L mutation. In particular, SEQ ID NO: 3 encodes the peptide of SEQ ID NO: 13. Likewise, SEQ ID NO: 6 is a nucleic acid that comprises the c.241T→C mutation and encodes a peptide that comprises the F81L mutation. In particular, SEQ ID NO: 6 encodes SEQ ID NO: 13.

The invention further comprises a nucleic acid with a sequence that is complementary to a nucleic acid encoding a THAP1 peptide. For example, a nucleic acid can be an antisense sequence that may be used to inhibit the expression of a THAP1 gene or mRNA in a cell. The complementary nucleic acid may be used as a probe to identify the presence of a nucleic acid encoding a THAP1 peptide.

In one embodiment, the invention relates to THAP1 peptides. More specifically, the invention relates to peptides comprising an amino acid sequence that comprises the F45fs73X mutation including, for example, SEQ ID NO: 12 and SEQ ID NO: 15. The invention further relates to peptides comprising an amino acid sequence that comprises the F81L mutation including, for example, SEQ ID NO: 13 and SEQ ID NO: 16.

In a further embodiment, the invention relates to peptides comprising an amino acid sequence of at least six amino acids that comprises the amino acid corresponding to position 145 of SEQ ID NO: 11 and amino acids immediately downstream and/or upstream of this amino acid. The invention relates to peptides that comprise an amino acid sequence of at least six amino acids that comprise the amino acid sequence of SEQ ID NO: 15. The invention further relates to peptides having an amino acid sequence of at least six amino acids comprising the amino acid corresponding to position 81 of SEQ ID NO: 11 and amino acids immediately downstream and/or upstream of this amino acid, wherein the peptide includes the F81L mutation. For example, the amino acid sequence PTILLCTE (SEQ ID NO: 16) comprises the amino acid corresponding to position 81 of SEQ ID NO: 11 and includes the F81L mutation.

Methods of obtaining isolated nucleic acids and oligonucleotides of the present invention are well known to those of skill in the art. For example, nucleic acid molecules encoding THAP1 and mutant THAP1 peptides may be obtained by restriction enzyme digestion of THAP1 genes or gene fragments, by automated synthesis of nucleic acid molecules, or by using the polymerase chain reaction (PCR) with oligonucleotide primers having nucleotide sequences that are based upon known nucleotide sequences of, for example, THAP1 genomic DNA and mRNA. Nucleotide sequences encoding peptides with amino acid substitutions or other mutations can be obtained, for example, by oligonucleotide-directed mutagenesis, linker-scanning mutagenesis, mutagenesis using the polymerase chain reaction, and the like (see Ausubel (1995): 8-10 through 8-22; and McPherson (ed.), *Directed Mutagenesis: A Practical Approach*, IRL Press (1991)).

In one embodiment, nucleic acids and oligonucleotides of the present invention are obtained by PCR amplification. For example, DNA can be extracted from white blood cells using the Purgene procedure (Gentra Systems Inc, Minneapolis, Minn.) or by other methods known in the art. Intron based, exon-specific primers can be designed from the UCSC human genome assembly sequence (March 2006 UCSC human genome assembly. genome.ucsc.edu) using Integrated DNA Technologies Primer Quest online server which is derived from Primer3 software (release 0.9) www.idtdna.com/Scitools/Applications/Primerquest/Default.aspx. For example, the following primers can be used to amplify THAP1 exons as follows:

In another embodiment, the nucleic acids and oligonucleotides of the invention can be obtained by cloning. For example, PCR fragments bearing the c.134_135insGGGTT; 137_139delAAC mutant allele, the c.241T→C mutant allele, or other mutant alleles described in Table 1 can be subcloned using the TOPO TA Cloning® Kit (Invitrogen) as described by the manufacturer and confirmed by forward and reverse sequencing. PCR can be performed according to techniques known to those of skill in the art. In one embodiment, PCR is performed using the THAP1 exon 2 primers described in Table 2 using the following PCR conditions: 35 cycles of 1 min at 95° C., 1 min at annealing temperature identified in Table 2 (57° for exons 2 and 3 and 60° for exon1) and 1 min at 72° C. The first step of denaturation and the last step of extension can each be 10 minutes at 95° C. and 72° C., respectively. Methods for optimizing PCR conditions are known to those of skill in the art. PCR products can be cloned into, for example, the TOPO® vector. The products of the

TABLE 2

Primers to Amplify THAP1 Exons

| Gene-Exon | Forward Primer Sequence | Reverse Primer Sequence | Annealing Temp. |
|---|---|---|---|
| THAP1-exon1 | TGTTCCAGGAGCGCGAGAAA (SEQ ID NO: 20) | AAACACCTGGCCTCAGCCAATA (SEQ ID NO: 21) | 60 |
| THAP1-exon2 | TCCTAAGCTGGAAAGTTTGGGTGC (SEQ ID NO: 22) | CACTGTTAACTACAAGGTTCCAGGCA (SEQ ID NO: 23) | 57 |
| THAP1-exon3 | GCCTGGTCAGTCCACAGATTCTT (SEQ ID NO: 24) | ACTCCTTTACAGGCTAGAGGAGGATA (SEQ ID NO: 25) | 57 |
| THAP1-exon3A | AGGCAAGAACGGCAGCTTGAAA (SEQ ID NO: 26) | AACTGGATGTCCTTCAGCTAGGGT (SEQ ID NO: 27) | 57 |
| THAP1-exon3B | AGTATGGGTCAGATCATGGGACA (SEQ ID NO: 28) | AGCCTTGTCCCAACTCAGTCAA (SEQ ID NO: 29) | 57 |
| THAP1-exon3C | ACTGGGACCTGATCTATGATACGCT (SEQ ID NO: 30) | TGAATCACAGTGCTATCCACTGGC (SEQ ID NO: 31) | 57 |

The following PCR conditions can be used with the primers identified in Table 2: 35 cycles of 1 min at 95° C., 1 min at annealing temperature identified in Table 2 (57° for exons 2 and 3 and 60° for exon1) and 1 min at 72° C. The first step of denaturation and the last step of extension are each 10 minutes at 95° C. and 72° C., respectively. THAP1 Exon1 sequence is GC rich and therefore the PCR reaction can be performed with AccuPrime™ GC-rich DNA polymerase (Invitrogen). The PCR amplification of the other THAP1 exons can be performed with, for example, Taq DNA polymerase from Applied Biosystems (ABI). The amplified fragments can be subjected to an enzymatic cleanup process with exonuclease I and shrimp alkaline phosphatase (USB, Corporation, Cleveland, Ohio) for 15 min at 37° C. and 15 min at 85° C., followed by standard dideoxy cycle sequencing. Sequence analysis can be performed, for example, by using Sequencher™ version 4.8 (Gene Codes, Ann Arbor, Mich.).

The primers in Table 2 can be used to amplify nucleic acids that comprise the mutations in Table 1. For example, the primers for exon 2 (SEQ ID NO: 22 and SEQ ID NO: 23) can be used to amplying nucleic acids comprising the mutations in Table 1 that are located in Exon 2 (as indicated by the third column of Table 1. Likewise, the primers for exon 1 (SEQ ID NO: 20 and SEQ ID NO: 21) can be used to amplifying nucleic acids comprising the mutations in Table 1 that are located in Exon 1.

cloning reaction can then be transformed into competent cells such as, for example, One Shot® chemically competent *E. coli* cells by heat shock. The bacterial culture can be plated on a media plate containing a drug to select for those cells that express the selectable marker. For example, a bacterial culture can be plated on a pre-warmed LB agar plate containing, for example, 100 µg/ml spectinomycin, and incubated overnight at 37° C. Cells that grow on the media containing drug can then be screen for the constructs of interest. For example, PCR can be performed using the PCR conditions described above for exon 2 of THAP1 and the products can be sequenced using procedures known to those of skill in the art to determine if the construct is wild-type THAP1 or mutant THAP1.

In yet another embodiment, the nucleic acids and oligonucleotides can be obtained by mutagenesis of the wild type THAP1 nucleic acid. For example, the full-length cDNA for the gene encoding human THAP1 (Ultimate ORF clone ID: IOH10776) can be purchased from Invitrogen. Human THAP1 can be transferred from the entry vector to the pcDNA3.1/nV5-Dest expression vector by Gateway recombinational cloning technique according to the manufacturer's instructions to introduce a V5 epitope tag at the N-terminus of THAP1, yielding pcDNA3.1/nV5-hTHAP1. The pcDNA3.1/nV5-hTHAP1-F81L mutant construct can be generated by QuikChange mutagenesis (Stratagene, La Jolla, Calif.), with the forward primer 5'-AGAATGCTGTGCCCACAATAcT-TCTTTGTACTGAGCC-3' (SEQ ID NO: 18) and the reverse primer 5'-GGCTCAGTACAAAGAAgTATTGTGGGCA-CAGCATTCT-3' (SEQ ID NO: 19) (the point mutation is indicated in lower case), using the pcDNA3.1/nV5-hTHAP1 construct as template. Preferably, all constructs are verified by sequencing. Primers that can be used to obtain other THAP1 mutant nucleic acids are listed in Table 3: AGCTGT-CAGAAGAAAAAACTTGGGTTTACCAC-CAAGTATAGCAG (SEQ ID NO: 40).

TABLE 3

Primers for Making THAP1 Mutant Nucleic Acids

| Mutation | Primers |
| --- | --- |
| C54Y | Forward Primer:<br>CCACCAAGTATAGCAGTATTTaTTCAGAGCACTTTACTCC<br>(SEQ ID NO: 32)<br>Reverse Primer:<br>GGAGTAAAGTGCTCTGAAtAAATACTGCTATACTTGGTGG<br>(SEQ ID NO: 33) |
| F81L | Forward Primer:<br>AGAATGCTGTGCCCACAATAcTTCTTTGTACTGAGCC<br>(SEQ ID NO: 18)<br>Reverse Primer:<br>GGCTCAGTACAAAGAAgTATTGTGGGCACAGCATTCT<br>(SEQ ID NO: 19) |
| H23Y | Forward Primer:<br>GACAAGCCCGTTTCTTTCtACAAGTTTCCTCTTACTC<br>(SEQ ID NO: 34)<br>Reverse Primer:<br>GAGTAAGAGGAAACTTGTaGAAAGAAACGGGCTTGTC<br>(SEQ ID NO: 35) |
| K89R | Forward Primer:<br>GTACTGAGCCACATGACAgGAAAGAAGATCTTCTGGA<br>(SEQ ID NO: 36)<br>Reverse Primer:<br>TCCAGAAGATCTTCTTTCcTGTCATGTGGCTCAGTAC<br>(SEQ ID NO: 37) |
| N12K | Forward Primer:<br>GCCTACGGCTGCAAGAAaCGCTACGACAAGG<br>(SEQ ID NO: 38)<br>Reverse Primer:<br>CCTTGTCGTAGCGtTTCTTGCAGCCGTAGGC<br>(SEQ ID NO: 39) |
| F45fs73 | Forward Primer:<br>AGCTGTCAGAAGAAAAAACTTGGGTTTACCACCAAGT<br>ATAGCAG<br>(SEQ ID NO: 40)<br>Reverse Primer:<br>AAGTTTTTCTTCTGACAGCTGCCTCCCATTCTTTAC<br>AAAGAC<br>(SEQ ID NO: 41) |
| R29P | Forward Primer:<br>CACAAGTTTCCTCTTACTCcACCCAGTCTTTGTAAAGAA<br>(SEQ ID NO: 42)<br>Reverse Primer:<br>TTCTTTACAAAGACTGGGTgGAGTAAGAGGAAACTTGTG<br>(SEQ ID NO: 43) |
| S21T | Forward Primer:<br>CAAGGACAAGCCCGTTaCTTTCCACAAGTTTCCT<br>(SEQ ID NO: 44)<br>Reverse Primer:<br>AGGAAACTTGTGGAAAGtAACGGGCTTGTCCTTG<br>(SEQ ID NO: 45) |

TABLE 3-continued

Primers for Making THAP1 Mutant Nucleic Acids

| Mutation | Primers |
| --- | --- |
| 154fsX180 | Forward Primer:<br>GGAAAAGGATTCATCAGCTAGAAAGCAAGTTGAAAAA<br>CTCAG<br>(SEQ ID NO: 46)<br>Reverse Primer:<br>CTGAGTTTTTCAACTTGCTTTCTAGCTGATGAATCCT<br>TTTCC<br>(SEQ ID NO: 47) |

The presence of a particular codon may have an adverse effect on expression in a particular host; therefore, a nucleic acid sequence may be optimized for a particular host system, such as prokaryotic or eukaryotic cells. Methods for altering nucleotide sequences to alleviate the codon usage problem are well known to those of skill in the art (see, e.g., Kane, *Curr. Opin. Biotechnol.* (1995) 6: 494; Makrides, *Microbiol. Rev.* (1996) 60: 512; and Brown (Ed.), *Molecular Biology LabFax*, BIOS Scientific Publishers, Ltd. (1991), which provides a Codon Usage Table at page 245 through page 253).

Peptides may be synthesized by recombinant techniques (see e.g., U.S. Pat. No. 5,593,866) and a variety of host systems are suitable for production of wild-type and mutant (e.g., F45fs73X, F81L and the other THAP1 mutations described in Table 1) THAP1, including bacteria (e.g., *E. coli*), yeast (e.g., *Saccharomyces cerevisiae*), insect (e.g., Sf9), and mammalian cells (e.g., CHO, COS-7). Many expression vectors have been developed and are available for each of these hosts. Vectors and procedures for cloning and expression in *E. coli* are discussed herein and, for example, in Sambrook et al. (Sambrook et al., *Molecular Cloning: A Laboratory Manual*, Cold Spring Harbor Laboratory Press, Cold Spring Harbor, N.Y. (1987)) and in Ausubel et al., 1995.

In one embodiment, the invention is directed to expression constructs that may be used to express, for example, wild-type or mutant (e.g., c.134_135insGGGTT;137_139de-1AAC, c.241T→C, or any of the other THAP1 mutations described in Table 1) THAP1 mRNA and protein. By "expression construct" is meant a nucleic acid sequence comprising a target nucleic acid sequence or sequences whose expression is desired, operatively associated with expression control sequence elements which provide for the proper transcription and translation of the target nucleic acid sequence(s) within the chosen host cells. Such sequence elements may include a promoter and a polyadenylation signal. The "expression construct" may further comprise "vector sequences". By "vector sequences" is meant any of several nucleic acid sequences established in the art which have utility in the recombinant DNA technologies of the invention to facilitate the cloning and propagation of the expression constructs including (but not limited to) plasmids, cosmids, phage vectors, viral vectors, and yeast artificial chromosomes.

Expression constructs of the present invention may comprise vector sequences that facilitate the cloning and propagation of the expression constructs. A large number of vectors, including plasmid and fungal vectors, have been described for replication and/or expression in a variety of eukaryotic and prokaryotic host cells. Standard vectors useful in the current invention are well known in the art and include (but are not limited to) plasmids, cosmids, phage vectors, viral vectors, and yeast artificial chromosomes. The vector sequences may contain a replication origin for propagation in *Escherichia coli* (*E. coli*); the SV40 origin of replication; an ampicillin, neomycin, or puromycin resistance gene for selection in host cells; and/or genes (e.g., dihydrofolate reductase gene) that amplify the dominant selectable marker plus the gene of interest.

A DNA sequence encoding wild type or mutant (e.g., c.134_135insGGGTT;137_139delAAC, c.241T→C, or any of the other THAP1 mutations described in Table 1) THAP1 can be introduced into an expression vector appropriate for the host. Potential host-vector systems include but are not limited to mammalian cell systems transfected with expression plasmids or infected with virus (e.g., vaccinia virus, adenovirus, adeno-associated virus, herpes virus, etc.); insect cell systems infected with virus (e.g., baculovirus); microorganisms such as yeast containing yeast vectors; or bacteria transformed with bacteriophage, DNA, plasmid DNA, or cosmid DNA.

The DNA sequence can be derived from an existing cDNA or genomic clone or it can be synthesized. A convenient method is amplification of the gene from a single-stranded template. The template can be the product of an automated oligonucleotide synthesis or can be denatured double-stranded template. Amplification primers are derived from the 5' and 3' ends of the template and typically incorporate restriction sites chosen with regard to the cloning site of the vector. If necessary, translational initiation and termination codons can be engineered into the primer sequences. The sequence encoding the protein may be codon-optimized for expression in the particular host. Codon optimization is accomplished by automated synthesis of the entire gene or gene region, ligation of multiple oligonucleotides, mutagenesis of the native sequence, or other techniques known to those in the art.

In some embodiments, the DNA sequence is cloned into a vector to create a fusion protein. The fusion partner of the invention may function to transport the fusion protein to certain cellular locations such as inclusion bodies, the periplasm, the outer membrane, or the extracellular environment. The fusion partner may function to allow the fusion protein to be visualized or detected. For example, the fusion partner may contain an epitope that is recognized by an antibody, a domain that binds to a peptide or nucleic acid, or a peptide that is more readily detectable (e.g., HA, myc, 6×His (SEQ ID NO: 88), Green Fluorescent Protein). Fusion partner include, but are not limited to, HA, myc, 6×His (SEQ ID NO: 88), Green Fluorescent Protein, glutathione-S-transferase (GST), protein A from *Staphylococcus aureus*, two synthetic IgG-binding domains (ZZ) of protein A, outer membrane protein F, β-galactosidase (lacZ), and various products of bacteriophage λ and bacteriophage T7. From the teachings provided herein, it is apparent that other proteins may be used as fusion partners. To facilitate isolation of the THAP1 sequence from the fusion protein, amino acids susceptible to chemical cleavage (e.g., CNBr) or enzymatic cleavage (e.g., V8 protease, trypsin) may be used to bridge the THAP1 wild-type or mutant peptide and the fusion partner.

A wide variety of host cell/expression vector combinations may be employed in expressing the DNA sequences of this invention. Useful expression vectors, for example, may consist of segments of chromosomal, non chromosomal and synthetic DNA sequences. Suitable vectors include derivatives of SV40 and known bacterial plasmids, e.g., *E. coli* plasmids col E1, pCR1, pBR322, pMal-C2, pET, pGEX (Smith et al., *Gene* (1988) 67: 31-40), pCR2.1 and pcDNA 3.1+ (Invitrogen, Carlsbad, Calif.), pMB9 and their derivatives, plasmids such as RP4; phage DNAs, e.g., the numerous derivatives of phage 1, e.g., NM989, and other phage DNA, e.g., M13 and filamentous single stranded phage DNA; yeast plasmids such as the 2m plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

Other suitable vectors include viral vectors, such as lentiviruses, retroviruses, herpes viruses, adenoviruses, adeno-associated viruses, vaccinia virus, baculovirus, and other recombinant viruses with desirable cellular tropism. Thus, a gene encoding a functional or mutant PTPN11 protein or polypeptide domain fragment thereof can be introduced in vivo, ex vivo, or in vitro using a viral vector or through direct introduction of DNA. Expression in targeted tissues can be effected by targeting the transgenic vector to specific cells, such as with a viral vector or a receptor ligand, or by using a tissue-specific promoter, or both. Targeted gene delivery is described in International Patent Publication WO 95/28494, published October 1995.

Viral vectors commonly used for in vivo or ex vivo targeting and therapy procedures (see below), as well as in vitro expression, are DNA-based vectors and retroviral vectors. Methods for constructing and using viral vectors are known in the art (see, e.g., Miller and Rosman, *BioTechniques* (1992) 7: 980-990). Preferably, the viral vectors are replication defective; that is, they are unable to replicate autonomously in the target cell. In general, the genome of the replication defective viral vectors which are used within the scope of the present invention lack at least one region which is necessary for the replication of the virus in the infected cell. These regions can either be eliminated (in whole or in part), or can be rendered non-functional by any technique known to a person skilled in the art. These techniques include the total removal, substitution (by other sequences, in particular by the inserted nucleic acid), partial deletion or addition of one or more bases to an essential (for replication) region. Such techniques may be performed in vitro (on the isolated DNA) or in situ, using the techniques of genetic manipulation or by treatment with mutagenic agents. Preferably, the replication defective virus retains the sequences of its genome which are necessary for encapsidating the viral particles.

DNA viral vectors include an attenuated or defective DNA virus, such as but not limited to herpes simplex virus (HSV), papillomavirus, Epstein Barr virus (EBV), adenovirus, adeno-associated virus (AAV), baculovirus, and the like. RNA viral vectors include, for example, retroviruses, lentiviruses, and alphaviruses (e.g., Sindbis virus and Venezuelan Equine Encephalitis virus), and the like. Defective viruses, which entirely or almost entirely lack viral genes, are preferred. Defective virus is not infective after introduction into a cell. Use of defective viral vectors allows for administration to cells in a specific, localized area, without concern that the vector can infect other cells. Thus, a specific tissue can be specifically targeted. Examples of particular vectors include, but are not limited to, a defective herpes virus 1 (HSV1) vector (Kaplitt et al., *Molec. Cell. Neurosci.* (1991) 2: 320-330), defective herpes virus vector lacking a glyco-protein L gene (Patent Publication RD 371005 A), or other defective herpes virus vectors (International Patent Publication No. WO 94/21807, published Sep. 29, 1994; International Patent Publication No. WO 92/05263, published Apr. 2, 1994); an attenuated adenovirus vector, such as the vector described by Stratford-Perricaudet et al. (J. Clin. Invest. (1992) 90: 626-630; see also La Salle et al., *Science* (1993) 259: 988-990); and a defective adeno-associated virus vector (Samulski et al., *J. Virol.* (1987) 61: 3096-3101; Samulski et al., *J. Virol.* (1989) 63: 3822-3828; Lebkowski et al., *Mol. Cell. Biol.* (1988) 8: 3988-3996).

Various companies produce viral vectors commercially, including but by no means limited to Avigen, Inc. (Alameda, Calif.; AAV vectors), Cell Genesys (Foster City, Calif.; retroviral, adenoviral, AAV vectors, and lentiviral vectors), Clontech (retroviral and baculoviral vectors), Genovo, Inc. (Sharon Hill, Pa.; adenoviral and AAV vectors), Genvec (adenoviral vectors), IntroGene (Leiden, Netherlands; adenoviral vectors), Molecular Medicine (retroviral, adenoviral, AAV, and herpes viral vectors), Norgen (adenoviral vectors), Oxford BioMedica (Oxford, United Kingdom; lentiviral vectors), Transgene (Strasbourg, France; adenoviral, vaccinia, retroviral, and lentiviral vectors) and Invitrogen (Carlbad, Calif.).

Within a preferred embodiment, the vector is capable of replication in bacterial cells. Thus, the vector may contain a bacterial origin of replication. Preferred bacterial origins of replication include f1-ori and col E1 ori, especially the on derived from pUC plasmids. Low copy number vectors (e.g., pPD100) may also be used, especially when the product is deleterious to the host. The plasmids also preferably include at least one selectable marker that is functional in the host. A selectable marker gene confers a phenotype on the host that allows transformed cells to be identified and/or selectively grown. Suitable selectable marker genes for bacterial hosts include the chloroamphenicol resistance gene ($Cm^r$), ampicillin resistance gene ($Amp^r$), tetracycline resistance gene ($Tc^r$), kanamycin resistance gene ($Kan^r$), and others known in the art. To function in selection, some markers may require a complementary deficiency in the host. The vector may also contain a gene coding for a repressor protein, which is capable of repressing the transcription of a promoter that contains a repressor binding site. Altering the physiological conditions of the cell can depress the promoter. For example, a molecule may be added that competitively binds the repressor, or the temperature of the growth media may be altered. Repressor proteins include, but are not limited to the E. coli lacI repressor (responsive to induction by IPTG), the temperature sensitive λcI857 repressor, and the like.

Preferably, the expression vector contains a promoter sequence. Suitable promoters, including both constitutive and inducible promoters, are widely available and are well known in the art. Commonly used promoters for expression in bacteria include promoters from T7, T3, T5, and SP6 phages, and the trp, lpp, and lac operons. Hybrid promoters (see, U.S. Pat. No. 4,551,433), such as tac and trc, may also be used. Examples of plasmids for expression in bacteria include the pET expression vectors pET3a, pET 11a, pET 12a-c, and pET 15b (see U.S. Pat. No. 4,952,496; available from Novagen, Madison, Wis.). Low copy number vectors (e.g., pPD100) can be used for efficient overproduction of peptides deleterious to the E. coli host (Dersch et al., FEMS Microbiol. Lett. 123: 19, 1994). Bacterial hosts for the T7 expression vectors may contain chromosomal copies of DNA encoding T7 RNA polymerase operably linked to an inducible promoter (e.g., lacUV promoter; see, U.S. Pat. No. 4,952,496), such as found in the E. coli strains HMS174(DE3)pLysS, BL21(DE3) pLysS, HMS174(DE3) and BL21(DE3). T7 RNA polymerase can also be present on plasmids compatible with the T7 expression vector. The polymerase may be under control of a lambda promoter and repressor (e.g., pGP1-2; Tabor and Richardson, Proc. Natl. Acad. Sci. USA (1985) 82: 1074, 1985).

Other promoters that may be used to control THAP1 expression include, but are not limited to, cytomegalovirus (CMV) promoter (U.S. Pat. Nos. 5,385,839 and 5,168,062), the SV40 early promoter region (Benoist and Chambon, Nature 1981, 290:304-310), the promoter contained in the 3' long terminal repeat of Rous sarcoma virus (Yamamoto, et al., Cell 1980, 22:787-797), the herpes thymidine kinase promoter (Wagner et al., Proc. Natl. Acad. Sci. U.S.A. (1981) 78: 1441-1445), the regulatory sequences of the metallothionein gene (Brinster et al., Nature 1982; 296:39 42); prokaryotic expression vectors such as the β-lactamase promoter (Villa-Komaroff et al., Proc. Natl. Acad. Sci. U.S.A. (1978) 75: 3727-3731), or the tac promoter (DeBoer et al., Proc. Natl. Acad. Sci. U.S.A. 1983; 80:21-25); see also "Useful proteins from recombinant bacteria" in Scientific American 1980; 242:74-94. Still other useful promoters that may be used include promoter elements from yeast or other fungi such as the Gal 4 promoter, the ADC (alcohol dehydrogenase) promoter, PGK (phosphoglycerol kinase) promoter, alkaline phosphatase promoter; and transcriptional control regions that exhibit hematopoietic tissue specificity, in particular: beta-globin gene control region which is active in myeloid cells (Mogram et al., Nature 1985; 315:338-340; Kollias et al., Cell 1986; 46:89-94), hematopoietic stem cell differentiation factor promoters, erythropoietin receptor promoter (Maouche et al., Blood 1991; 15:2557), etc.

Other regulatory sequences may also be included. Such sequences include an enhancer, ribosome binding site, transcription termination signal sequence, secretion signal sequence, origin of replication, selectable marker, and the like. The regulatory sequences are operably linked with one another to allow transcription and subsequent translation.

The invention further provides for an isolated cell comprising an expression construct. The expression construct comprises a nucleic acid that encodes a THAP1 peptide, including a THAP1 peptide that comprises the F45fs73X mutation, the F81L mutation or any of the other THAP1 mutations described in Table 1. For example, the THAP1 nucleic acid may comprise any of SEQ ID NOS: 2, 3, 5, 6, 9 or 10. The nucleic acid may encode a peptide that comprises any of SEQ ID NOS: 12, 13, 15, or 16. In one embodiment, the cell is a eukaryotic cell. In another embodiment, the isolated cell is a prokaryotic cell.

Expression constructs of the invention can be introduced into host cells by methods well known to those of skill in the art including, for example, electroporation, microinjection, cell fusion, DEAE dextran, $Ca^{2+}$-mediated techniques, use of a gene gun, or use of a DNA vector transporter (see, e.g., Wu et al., J. Biol. Chem. (1992) 267: 963-967; Wu and Wu, J. Biol. Chem. (1988) 263: 14621-14624; Hartmut et al., Canadian Patent Application No. 2,012,311, filed Mar. 15, 1990; Williams et al., Proc. Natl. Acad. Sci. U.S.A. 1991; 88:2726-2730). Receptor-mediated DNA delivery approaches can also be used (Curiel et al., Hum. Gene Ther. 1992; 3:147-154; Wu and Wu, J. Biol. Chem. 1987; 262:4429-4432). U.S. Pat. Nos. 5,580,859 and 5,589,466 disclose delivery of exogenous DNA sequences, free of transfection facilitating agents, in a mammal. Recently, a relatively low voltage, high efficiency in vivo DNA transfer technique, termed electrotransfer, has been described (Mir et al., C. P. Acad. Sci. 1998; 321:893; WO 99/01157; WO 99/01158; WO 99/01175).

In one embodiment, the expression construct can be introduced in vivo by lipofection, as naked DNA, or with other transfection facilitating agents (peptides, polymers, etc.). Synthetic cationic lipids can be used to prepare liposomes for in vivo transfection of a gene encoding a marker (Felgner et al., Proc. Natl. Acad. Sci. U.S.A. (1987) 84: 7413-7417; Feigner and Ringold, Science (1989) 337: 387-388; Mackey et al., Proc. Natl. Acad. Sci. U.S.A. (1988) 85: 8027-8031; Ulmer et al., Science (1993) 259: 1745-1748). Useful lipid compounds and compositions for transfer of nucleic acids are described in International Patent Publications WO 95/18863 and WO 96/17823, and in U.S. Pat. No. 5,459,127. Lipids may be chemically coupled to other molecules for the purpose of targeting (see, Mackey et al., *Proc. Natl. Acad. Sci. U.S.A.* (1988) 85: 8027-8031). Targeted peptides, and proteins such as antibodies, or non-peptide molecules could be coupled to liposomes chemically. Other molecules are also useful for facilitating transfection of a nucleic acid in vivo, such as a cationic oligopeptide (e.g., International Patent Publication WO 95/21931), peptides derived from DNA binding proteins (e.g., International Patent Publication WO 96/25508), or a cationic polymer (e.g., International Patent Publication WO 95/21931).

Preferably, for in vivo administration, an appropriate immunosuppressive treatment is employed in conjunction with a viral vector, e.g., adenovirus vector, to avoid immuno-deactivation of the viral vector and transfected cells. For example, immunosuppressive cytokines, such as interleukin-12 (IL-12), interferon-γ (IFN-γ), or anti-CD4 antibody, can be administered to block humoral or cellular immune responses to the viral vectors (see, e.g., Wilson, Nat. Med. 1995; 1:887-889). In that regard, it is advantageous to employ a viral vector that is engineered to express a minimal number of antigens.

Soluble forms of the protein can be obtained by collecting culture fluid, or solubilizing-inclusion bodies, e.g., by treatment with detergent, and if desired sonication or other mechanical processes, as described above. The solubilized or soluble protein can be isolated using various techniques, such as polyacrylamide gel electrophoresis (PAGE), isoelectric focusing, 2 dimensional gel electrophoresis, chromatography (e.g., ion exchange, affinity, immunoaffinity, and sizing column chromatography), centrifugation, differential solubility, immunoprecipitation, or by any other standard technique for the purification of proteins.

Methods of Detecting a THAP1 Mutation

According to the invention, mutated forms of THAP1 nucleic acids and proteins, as well as deregulated expression of THAP1 (e.g. over-expression of THAP1), can be detected by a variety of suitable methods known to those of skill in the art.

In a preferred embodiment, the determination of mutations in the THAP1 gene encompasses the use of nucleic acid sequences, such as specific oligonucleotides, to detect mutations in, for example, THAP1 genomic DNA or mRNA in a biological sample. Such oligonucleotides may specifically hybridize to a site of mutation, or to a region adjacent to this site of mutation present in a THAP1 nucleic acid. One may also employ primers that permit amplification of all or part of THAP1. Alternatively, or in combination with such techniques, oligonucleotide sequencing described herein or known to the skilled artisan can be applied to detect THAP1 mutations.

In one embodiment, one skilled in the art may use oligonucleotide primers in an amplification technique, such as the polymerase chain reaction (PCR), to specifically amplify the target DNA in a biological sample. Thus, the present invention is directed to a method of detecting the presence of a THAP1 mutation in a biological sample from a subject, comprising:

a) obtaining a biological sample comprising DNA from a subject;
b) contacting the biological sample with primer pairs that allow for specific amplification of all or part of the THAP1 DNA, under conditions permitting hybridization of the primers to the DNA;
c) amplifying the THAP1 DNA; and
d) comparing the amplified products obtained from the subject to the amplified products obtained with a normal control biological sample, whereby a difference between the product from the subject and the product from the normal sample indicates the presence of a THAP1 mutation in the subject.

PCR is a method that allows exponential amplification of a DNA sequence (including sequences up to several kilobases) from a double stranded DNA. PCR entails the use of a pair of primers that are complementary to a defined sequence on each of the two strands of the DNA. These primers are extended by a DNA polymerase so that a copy is made of the designated sequence. After making this copy, the same primers can be used again, not only to make another copy of the input DNA strand but also of the copy made in the first round of synthesis. This leads to logarithmic amplification. Since it is necessary to raise the temperature to separate the two strands of the double strand DNA in each round of the amplification process, a major step forward was the discovery of a thermo-stable DNA polymerase (Taq polymerase) that was isolated from *Thermus aquaticus*, a bacterium that grows in hot pools; as a result it is not necessary to add new polymerase in every round of amplification. After several (often about 40) rounds of amplification, the PCR product is usually abundant enough to be detected with an ethidium bromide stain so that it can be analyzed on an agarose gel.

In other embodiments, real-time PCR, also called quantitative real time PCR, quantitative PCR (Q-PCR/qPCR), or kinetic polymerase chain reaction, is a laboratory technique based on PCR, which is used to amplify and simultaneously quantify a targeted DNA molecule. qPCR enables both detection and quantification (as absolute number of copies or relative amount when normalized to DNA input or additional normalizing genes) of a specific sequence in a DNA sample. For example, in the embodiments disclosed herein, qPCR may be used to quantify the amount of fungal DNA in a patient sample. The procedure follows the general principle of PCR; its key feature is that the amplified DNA is quantified as it accumulates in the reaction in real time after each amplification cycle. Two common methods of quantification are the use of fluorescent dyes that intercalate with double-stranded DNA, and modified DNA oligonucleotide probes that fluoresce when hybridized with a complementary DNA. The qPCR results may be quantitated using the ΔΔCt method. This method involves calculating a ΔCt between the average target gene Ct and average housekeeping gene Ct for a given target in each treatment group. The ΔΔCt is used to calculate the "n-fold" change in gene expression between groups.

As used herein, a "polymerase" refers to an enzyme that catalyzes the polymerization of nucleotides. Generally, the enzyme will initiate synthesis at the 3'-end of the primer annealed to a nucleic acid template sequence. "DNA polymerase" catalyzes the polymerization of deoxyribonucleotides. Known DNA polymerases include, for example, *Pyrococcus furiosus* (Pfu) DNA polymerase (Lundberg et al., 1991, Gene, 108:1), *E. coli* DNA polymerase I (Lecomte and Doubleday, 1983, Nucleic Acids Res. 11:7505), T7 DNA polymerase (Nordstrom et al., 1981, J. Biol. Chem. 256: 3112), *Thermus thermophilus* (Tth) DNA polymerase (Myers and Gelfand 1991, Biochemistry 30:7661), *Bacillus stearothermophilus* DNA polymerase (Stenesh and McGowan, 1977, Biochim Biophys Acta 475:32), *Thermococcus litoralis* (Tli) DNA polymerase (also referred to as Vent DNA polymerase, Cariello et al., 1991, Nucleic Acids Res, 19: 4193), *Thermotoga maritima* (Tma) DNA polymerase (Diaz and Sabino, 1998 Braz J. Med. Res, 31:1239), *Thermus aquaticus* (Taq) DNA polymerase (Chien et al., 1976, J. Bacteoriol, 127: 1550), *Pyrococcus kodakaraensis* KOD DNA polymerase (Takagi et al., 1997, Appl. Environ. Microbiol. 63:4504), JDF-3 DNA polymerase (Patent application WO 0132887), AccuPrime™ GC-rich DNA polymerase (Invitrogen, Carlsbad, Calif.), and *Pyrococcus* GB-D (PGB-D) DNA polymerase (Juncosa-Ginesta et al., 1994, Biotechniques, 16:820). The polymerase activity of any of the above enzymes can be determined by means well known in the art.

The term "primer," as used herein, refers to an oligonucleotide capable of acting as a point of initiation of DNA synthesis under conditions in which synthesis of a primer extension product complementary to a nucleic acid strand is induced, i.e., either in the presence of four different nucleoside triphosphates and an agent for extension (e.g., a DNA polymerase or reverse transcriptase) in an appropriate buffer and at a suitable temperature. A primer is preferably a single-stranded DNA. The appropriate length of a primer depends on the intended use of the primer but typically ranges from 6 to 50 nucleotides, preferably from 15-35 nucleotides. Short primer molecules generally require cooler temperatures to form sufficiently stable hybrid complexes with the template. A primer need not reflect the exact sequence of the template nucleic acid, but must be sufficiently complementary to hybridize with the template. The design of suitable primers for the amplification of a given target sequence is well known in the art and described in the literature cited herein. As used herein, a "forward primer" is understood to mean a primer that is capable of hybridizing to a region of DNA along the 5' (coding) strand of DNA. A "reverse" primer is understood to mean a primer that is capable of hybridizing to a region of DNA along the 3' (non-coding) strand of DNA.

As used herein, a primer is "specific," for a target sequence if, when used in an amplification reaction under sufficiently stringent conditions, the primer hybridizes primarily only to the target nucleic acid. Typically, a primer is specific for a target sequence if the primer-target duplex stability is greater than the stability of a duplex formed between the primer and any other sequence found in the sample. One of skill in the art will recognize that various factors, such as salt conditions as well as base composition of the primer and the location of the mismatches, will affect the specificity of the primer, and that routine experimental confirmation of the primer specificity will be needed in most cases. Hybridization conditions can be chosen under which the primer can form stable duplexes only with a target sequence. Thus, the use of target-specific primers under suitably stringent amplification conditions enables the specific amplification of those target sequences which contain the target primer binding sites. The use of sequence-specific amplification conditions enables the specific amplification of those target sequences which contain the exactly complementary primer binding sites.

A "primer set" or "primer pair" refers to a specific combination of a forward primer and a reverse primer. The "primer set" or "primer pair" may be used in a PCR reaction to generate a specific PCR product or amplicon.

In certain embodiments, the term "primer" is also intended to encompass the oligonucleotides used in ligation-mediated amplification processes, in which one oligonucleotide is "extended" by ligation to a second oligonucleotide which hybridizes at an adjacent position. Thus, the term "primer extension", as used herein, refers to both the polymerization of individual nucleoside triphosphates using the primer as a point of initiation of DNA synthesis and to the ligation of two oligonucleotides to form an extended product.

Methods of obtaining a biological sample comprising nucleic acid, such as DNA, from a subject are well known in the art. In a preferred embodiment, DNA is extracted from white blood cells using the Purgene procedure (Gentra Systems Inc, Minneapolis, Minn.). DNA can also be obtained from buccal cells either from a cheek swab or from a mouthwash sample and extracted using the Puregene procedure.

Useful primer pairs that permit specific amplification of all or part of THAP1 genomic DNA or cDNA can be designed from the UCSC human genome assembly sequence (March 2006 UCSC human genome assembly. genome.ucsc.edu) using Integrated DNA Technologies Primer Quest online server which is derived from Primer3 software (release 0.9) www.idtdna.com/Scitools/Applications/Primerquest/Default.aspx. Examples of primers that can be used include the primers set forth in Table 2. For example, the c.241T>C mutation (e.g., SEQ ID NO: 6) can be amplified using exon 2 forward (SEQ ID NO: 22) and reverse (SEQ ID NO: 23) primers and the following amplification conditions: 95° C. 10 min; 95° C. 1 min-57° C. 1 min-72° C. 1 min (35 cycles); 72° C. 10 min.

The amplified nucleic acid from the subject is then compared to the amplified products obtained with a normal control biological sample or to the sequence of wild-type THAP1 nucleic acid, including a THAP1 genomic DNA or mRNA, such as SEQ ID NO: 1 and SEQ ID NO: 4. Differences between the sequence of the THAP1 nucleic acid from the subject and the sequence of the wild-type THAP1 nucleic acid (or amplification products obtained from a normal control biological sample) are identified as THAP1 mutations. In particular, a c.134_135insGGGTT;137_139delAAC mutation (e.g., SEQ ID NO: 5), a c.241T→C mutation, or any of the mutations identified in Table 1 would be identified as a THAP1 mutation.

The method of the invention can also be applied to the detection of an abnormality in the transcript of the THAP1 gene, e.g. by amplifying the mRNAs contained in a biological sample, for example by RT-PCR. Thus another aspect of the present invention is a method of detecting the presence of a THAP1 mutation in a biological sample from a subject, comprising the steps of:

a) obtaining a biological sample comprising RNA from a subject;
b) producing cDNA from RNA contained in the biological sample;
c) contacting the cDNA with specific primers permitting the amplification of all or part of the transcript of the THAP1 gene, under conditions permitting hybridization of the primers with the cDNA;
d) amplifying the cDNA; and
e) comparing the amplified products obtained from the subject to the amplified products obtained with a normal control biological sample, whereby a difference between the product from the subject and the product from the normal sample indicates the presence of a THAP1 mutation in the subject.

A biological sample comprising RNA from a subject may be obtained from any cell source from which RNA can be isolated using standard methods well known to those of ordinary skill in the art such as guanidium thiocyanate-phenol-chloroform extraction (Chomocyznski et al., Anal. Biochem. 1987; 162-156) Other methods of obtaining a biological sample comprising RNA include homogenizing tissue samples prior to RNA extraction and extracting total RNA from tissue homogenates, cell or blood samples using Trizol reagent (Invitrogen, Carlsbad, Calif.) in conjugation with PureLink™ Micro-to-Midi Total RNA purification system (Invitrogen, Carlsbad, Calif.) according to the manufacturer's instructions. In particular, lysates can be prepared using 1 ml of Trizol reagent and incubating for 5 minutes at room temperature. After homogenization, ethanol is added to the sample and then the sample is processed through a spin cartridge. RNA binds to the silica based membrane in the spin cartridge and impurities are effectively removed by washing. The purified total RNA is eluted, for example in 30 μl of RNase free water. Complementary DNA (cDNA) can then be produced from the RNA by procedures known to those of skill in the art. For example, reverse transcription (RT) can be used to reverse transcribe RNA, including total cellular RNA or poly(A) RNA, using a reverse transcriptase enzyme, a primer, dNTPs and an RNase inhibitor. As one of skill in the art will appreciate, several different types of primers can be used, including oligo (dT) primers, random (hexamer) primers and gene specific primers.

For a RT reaction, 1-2 micrograms of RNA is typically used. Generally, the RNA is first incubated with a primer at 70° C. to denature the RNA secondary structure and then quickly chilled on ice to let the primer anneal to the RNA. Generally, other components of the RT reaction are added including dNTPs, RNase inhibitor, reverse transcriptase and RT buffer. The RT reaction can be extended at 42° C. for, for example, 1 hr. The reaction can then be heated at 70° C. degree to inactivate the enzyme. Sometimes removal of the template RNA by treating the RT reaction with RNase H is performed before using the reaction in RT-PCR. The isolated RNA can alternatively be subjected to coupled reverse transcription and amplification by polymerase chain reaction (RT-PCR), using specific oligonucleotide primers that are specific for a selected site. In one embodiment, RT-PCR can be performed using the Platinum™ quantitative RT-PCR ThermoScrip™ one-step system (GIBCO BRL). In one embodiment, first strand cDNA is prepared using SuperScript™ First Strand Synthesis System for RT-PCR (Invitrogen, Carlsbad, Calif.) according to the manufacturer's instructions. In one embodiment, for reverse transcription 500 ng to 1 μg of RNA is used. The RNA is incubated with random hexamer primers and dNTPs at 65° C. to denature RNA secondary structure and then quickly chilled on ice to let the primer anneal to the RNA. The cDNA Synthesis Mix containing 10×RT buffer, 25 mM $MgCl_2$, 0.1M DTT, RNase OUT Recombinant RNase Inhibitor and SuperScript™ III Reverse Transcriptase enzyme is added. The reaction is performed in two steps: 50 minutes at 50° C. followed by 5 minutes at 85° C. Then the reaction is treated by RNaseH to remove the RNA template.

Amplification of the cDNA and comparison of the amplified products with a normal control biological sample or to the sequence of wild-type THAP1 nucleic acid such as a THAP1 genomic DNA or mRNA can be performed as described above. In particular, a c.134_135insGGGTT;137_139delAAC, a c.241T→C mutation, or any other mutation identified in Table 1 would be identified as a THAP1 mutation.

The primers and conditions for primer annealing can be chosen to ensure specific reverse transcription and amplification only of a particular (e.g., mutant) THAP1 sequence; thus, the appearance of an amplification product can be diagnostic of the presence of a particular genetic variation. In another embodiment, the primers and conditions for primer annealing can be chosen so that an amplification product is obtained with wild-type or mutant THAP1, but not both. The mRNA is reverse-transcribed and amplified, after which the amplified sequences are identified by, e.g., direct sequencing.

In a preferred embodiment, the amplified fragments are subjected to an enzymatic cleanup process with exonuclease I and shrimp alkaline phosphatase (USB, Corporation, Cleveland, Ohio) for 15 min at 37° C. and 15 min at 85° C., followed by standard dideoxy cycle sequencing.

Sequence analysis can be performed by a variety of suitable methods known to those of skilled in the art. In a preferred embodiment, sequence analysis is performed using Sequencher™ (Gene Codes, Ann Arbor, Mich.).

In still another embodiment, the DNA or cDNA obtained from RNA can be first cloned and then sequenced to identify a mutation. Methods of cloning DNA and cDNA are well known to those of skill in the art. In a preferred embodiment, the DNA or cDNA is subcloned using the TOPO TA Cloning$^R$ Kit (Invitrogen) as described by the manufacturer and confirmed by forward and reverse sequencing.

In a further embodiment, a method of detecting the presence of a THAP1 mutation in a biological sample from a subject comprises obtaining a biological sample from a subject that comprises DNA or RNA; optionally producing cDNA from the RNA contained in the biological sample (e.g., if the biological sample comprises mRNA and not DNA); contacting the DNA or cDNA with specific oligonucleotides permitting the amplification of all or part of the THAP1 gene or transcript of the THAP1 gene; digesting the amplified product with at least one restriction enzyme; and comparing the restriction fragments of the amplified product from the subject with the restriction fragments obtained from the amplification of a normal control biological sample, whereby a difference between the restriction fragments from the subject and the restriction fragments from the normal sample indicates the presence of a THAP1 mutation in the subject. If sufficient cDNA or DNA is present, the cDNA or DNA may be treated with at least one restriction enzyme without an intervening amplification step. For example, DNA or cDNA (obtained from RNA) PCR products can be digested with the restriction enzymes DraI to test for a c.134_135insGGGTT; 137_139delAAC mutation (e.g., SEQ ID NO: 5) or SspI to test for a c.241T>C mutation (e.g., SEQ ID NO: 6). For SspI, digestion of a 400 bp PCR product from wild-type THAP1, obtained using the exon 2 primers in Table 2, will result in restriction fragments of 245, 108, and 47 base pairs in length. Digestion of a 400 bp PCR product from a c.241T>C THAP1 mutant will result in restriction fragments of 292 and 108 base pairs. The c.241T>C mutation (e.g., SEQ ID NO: 6) lacks a SspI restriction site in the 292 base pair fragment that is present in wild type. Therefore, in a heterozygous individual (one wild type and one c.241T>C allele), a SspI digestion of the PCR products would result in restriction fragments of 292, 245, 108, and 47 base pairs. DraI digestion of a 400 bp PCR product from wild type THAP1 results in restriction fragments of 36, 105, 113 and 146 base pairs. Digestion of a 400 bp PCR product from a c.134_135insGGGTT;137_139delAAC mutant results in restriction fragments of 36 bp, 113 bp and 251 base pairs. The c.134_135insGGGTT;137_139delAAC mutant is missing a DraI restriction site in the 251 base pair fragment. Therefore, in a heterozygous individual (one wild type and one c.134_135insGGGTT;137_139delAAC allele), a DraI digestion of the PCR products would result in restriction fragments of 36, 105, 113, 146, and 251 base pairs. The disease is dominantly inherited so we would not expect any homozygous mutation carriers. The restriction enzyme Taq1 may be used to test for a R29X mutation and the restriction enzyme MwoI may be used to test for a Q154fs180X mutation.

One skilled in the art may use hybridization probes in solution and in embodiments employing solid-phase procedures. In embodiments involving solid-phase procedures, the test nucleic acid is adsorbed or otherwise affixed to a selected matrix or surface. The fixed, single-stranded nucleic acid is then subjected to specific hybridization with selected probes.

The THAP1 nucleic acids of the invention can also be used as probes, e.g., in therapeutic and diagnostic assays. For instance, the present invention provides a probe comprising an oligonucleotide that comprises a sequence that is capable of hybridizing specifically to a region of a wild-type THAP1 gene. In one embodiment, a method for detecting the presence of a THAP1 mutation comprises:

obtaining a biological sample from a subject that comprises DNA or RNA;

if the sample comprises RNA, producing cDNA from the RNA contained in the biological sample;

contacting the DNA or cDNA with an oligonucleotide, wherein the oligonucleotide comprises the sequence of SEQ ID NO: 7 or comprises a sequence that is complementary to the sequence of SEQ ID NO: 7; and determining whether the oligonucleotide bound to the DNA or cDNA.

Lack of binding of an oligonucleotide that comprises the sequence of SEQ ID NO: 7 or that comprises a sequence that is complementary to the sequence of SEQ ID NO: 7 to the DNA or cDNA from a subject indicates the presence of a mutation in a THAP1 gene or transcript of the subject.

In another embodiment, a method for detecting the presence of a THAP1 mutation comprises:

obtaining a biological sample from a subject that comprises DNA or RNA;

if the sample comprises RNA, producing cDNA from the RNA contained in the biological sample;

contacting the DNA or cDNA with an oligonucleotide, wherein the oligonucleotide comprises the sequence of SEQ ID NO: 8 or comprises a sequence that is complementary to the sequence of SEQ ID NO: 8; and determining whether the oligonucleotide bound to the DNA or cDNA.

Lack of binding of an oligonucleotide that comprises the sequence of SEQ ID NO: 8 or that comprises a sequence that is complementary to the sequence of SEQ ID NO: 8 to the DNA or cDNA from a subject indicates the presence of a mutation in a THAP1 gene or transcript of the subject.

The present invention also provides a probe comprising a substantially purified oligonucleotide, which oligonucleotide comprises a sequence that is capable of hybridizing specifically to a region of a THAP1 gene which differs from that of the wild-type THAP1 gene or mRNA (e.g., SEQ ID NO: 1, SEQ ID NO: 4), e.g., a mutant or polymorphic region. Such probes can then be used to specifically detect which mutation of the THAP1 gene is present in a sample taken from a subject. The mutant or polymorphic region can be located in the promoter, exon, or intron sequences of the THAP1 gene.

In one embodiment, a method for detecting the presence of a THAP1 mutation comprises obtaining a biological sample from a subject that comprises DNA or RNA;

if the sample comprises RNA, producing cDNA from the RNA contained in the biological sample;

contacting the DNA or cDNA with an oligonucleotide, wherein the oligonucleotide comprises the sequence of SEQ ID NO: 9 or comprises a sequence that is complementary to the sequence of SEQ ID NO: 9; and determining whether the oligonucleotide bound to the DNA or cDNA.

Binding of an oligonucleotide that comprises the sequence of SEQ ID NO: 9 or that comprises a sequence that is complementary to the sequence of SEQ ID NO: 9 to the DNA or cDNA from a subject indicates the presence of a c.134_135insGGGTT;137_139delAAC mutation (e.g., SEQ ID NO: 5) in a THAP1 gene or transcript of the subject.

In one embodiment, a method for detecting the presence of a THAP1 mutation comprises obtaining a biological sample from a subject that comprises DNA or RNA;

if the sample comprises RNA, producing cDNA from the RNA contained in the biological sample;

contacting the DNA or cDNA with an oligonucleotide, wherein the oligonucleotide comprises the sequence of SEQ ID NO: 10 or comprises a sequence that is complementary to the sequence of SEQ ID NO: 10; and determining whether the oligonucleotide bound to the DNA or cDNA.

Binding of an oligonucleotide that comprises the sequence of SEQ ID NO: 10 or that comprises a sequence that is complementary to the sequence of SEQ ID NO: 10 to the DNA or cDNA from a subject indicates the presence of a c.241T>C mutation (e.g., SEQ ID NO: 6) in a THAP1 gene or transcript of the subject.

Probes of the invention include one or more of the nucleotide substitutions listed in Table 1, as well as the wild-type flanking regions (see, e.g., SEQ ID NOS: 2, 3, 5, 6, 9 or 10). For each such probe, the complement of that probe is also a preferred probe of the invention. Particularly preferred probes of the invention have a number of nucleotides sufficient to allow specific hybridization to the target nucleotide sequence. Thus, probes of suitable lengths that include one or more of the nucleotide substitutions listed in Table 1, including sequences that include SEQ ID NOS: 2, 3, 5, 6, 9, 10 or 50-68), or that are complementary to the mutant sequences provided herein, can be constructed and tested by the skilled artisan for the appropriate level of specificity depending on the application intended. Where the target nucleotide sequence is present in a large fragment of DNA, such as a genomic DNA fragment of several tens or hundreds of kilobases, the size of the probe may have to be longer to provide sufficiently specific hybridization, as compared to a probe which is used to detect a target sequence which is present in a shorter fragment of DNA. For example, in some diagnostic methods, a portion of the THAP1 gene may first be amplified and thus isolated from the rest of the chromosomal DNA and then hybridized to a probe. In such a situation, a shorter probe will likely provide sufficient specificity of hybridization. For example, a probe having a nucleotide sequence of about 10 nucleotides may be sufficient, although probes of about 15 nucleotides, even more preferably 20 nucleotides, are preferred.

In a preferred embodiment, the probe or primer further comprises a label attached thereto, which preferably is capable of being detected. The label can, for example, be selected from radioisotopes, fluorescent compounds, enzymes, and enzyme co-factors.

In another preferred embodiment of the invention, the isolated nucleic acid, which is used, e.g., as a probe or a primer, is modified, such as to become more stable. Exemplary nucleic acid molecules which are modified include phosphoramidate, phosphothioate and methylphosphonate analogs of DNA (see also U.S. Pat. Nos. 5,176,996; 5,264,564; and 5,256,775).

In yet another embodiment, one may use HPLC or denaturing HPLC (DHPLC) techniques to analyze the THAP1 nucleic acids. DHPLC was developed when observing that, when HPLC analyses are carried out at a partially denaturing temperature, i.e., a temperature sufficient to denature a heteroduplex at the site of base pair mismatch, homoduplexes can be separated from heteroduplexes having the same base pair length (Hayward-Lester et al., Genome Research (1995) 5:494; Underhill et al., Proc. Natl. Acad. Sci. USA (1996)

93:193; Doris et al., DHPLC Workshop (1997) Stanford University). Thus, the use of DHPLC was applied to mutation detection (Underhill et al., Genome Research (1997) 7:996; Liu et al., Nucleic Acid Res. (1998) 26:1396). DHPLC can separate heteroduplexes that differ by as little as one base pair. "Matched Ion Polynucleotide Chromatography" (MIPC), or Denaturing "Matched Ion Polynucleotide Chromatography" (DMIPC) as described in U.S. Pat. Nos. 6,287,822 or 6,024,878, are separation methods that can also be useful in connection with the present invention.

Alternatively, one can use the DGGE method (Denaturing Gradient Gel Electrophoresis), or the SSCP method (Single Strand Conformation Polymorphism) for detecting an abnormality in the THAP1 gene. DGGE is a method for resolving two DNA fragments of identical length on the basis of sequence differences as small as a single base pair change, using electrophoresis through a gel containing varying concentrations of denaturant (Guldberg et al., Nuc. Acids Res. (1994) 22:880). SSCP is a method for detecting sequence differences between two DNAs, comprising hybridization of the two species with subsequent mismatch detection by gel electrophoresis (Ravnik-Glavac et al., Hum. Mol. Genet. (1994) 3:801). "HOT cleavage", a method for detecting sequence differences between two DNAs, comprising hybridization of the two species with subsequent mismatch detection by chemical cleavage (Cotton et al., Proc. Natl. Acad. Sci. USA (1988) 85:4397), can also be used. Such methods are preferably followed by direct sequencing. Advantageously, the RT-PCR method may be used for detecting abnormalities in the THAP1 transcript, as it allows one to visualize the consequences of a splicing mutation such as exon skipping or aberrant splicing due to the activation of a cryptic site. Preferably this method is followed by direct sequencing as well.

More recently developed techniques using microarrays, preferably microarray techniques allowing for high-throughput screening, can also be advantageously implemented for detecting an abnormality in the THAP1 gene or for assaying expression of the THAP1 gene. Microarrays may be designed so that the same set of identical oligonucleotides is attached to at least two selected discrete regions of the array, so that one can easily compare a normal sample, contacted with one of the selected regions of the array, against a test sample, contacted with another of the selected regions. These arrays avoid the mixture of normal sample and test sample, using microfluidic conduits. Useful microarray techniques include those developed by Nanogen, Inc (San Diego, Calif.) and those developed by Affymetrix. However, all types of microarrays, also called "gene chips" or "DNA chips", may be adapted for the identification of mutations. Such microarrays are well known in the art (see for example the following: U.S. Pat. Nos. 6,045,996; 6,040,138; 6,027,880; 6,020,135; 5,968,740; 5,959,098; 5,945,334; 5,885,837; 5,874,219; 5,861,242; 5,843,655; 5,837,832; 5,677,195 and 5,593,839).

The solid support on which oligonucleotides are attached may be made from glass, silicon, plastic (e.g., polypropylene, nylon), polyacrylamide, nitrocellulose, or other materials. One method for attaching the nucleic acids to a surface is by printing on glass plates, as is described generally by Schena et al., Science (1995) 270:467-470. This method is especially useful for preparing microarrays of cDNA. See also DeRisi et al., Nature Genetics (1996) 14:457-460; Shalon et al., Genome Res. (1996) 6:639-645; and Schena et al., Proc. Natl. Acad. Sci. USA (1995) 93:10539-11286. Another method of making microarrays is by use of an inkjet printing process to bind genes or oligonucleotides directly on a solid phase, as described, e.g., in U.S. Pat. No. 5,965,352.

Other methods for making microarrays, e.g., by masking (Maskos and Southern, Nuc. Acids Res. (1992) 20:1679-1684), may also be used. In principal, any type of array, for example, dot blots on a nylon hybridization membrane (see Sambrook et al., Molecular Cloning A Laboratory Manual (2nd Ed.), Vol. 1-3, Cold Spring Harbor Laboratory, Cold Spring Harbor, N.Y., 1989) could be used, although, as will be recognized by those of skill in the art, very small arrays will be preferred because hybridization volumes will be smaller. For these assays nucleic acid hybridization and wash conditions are chosen so that the attached oligonucleotides "specifically bind" or "specifically hybridize" to at least a portion of the THAP1 nucleic acid present in the tested sample, i.e., the probe hybridizes, duplexes or binds to the THAP1 locus with a complementary nucleic acid sequence but does not hybridize to a site with a non-complementary nucleic acid sequence. As used herein, one polynucleotide sequence is considered complementary to another when, if the shorter of the polynucleotides is less than or equal to 25 bases, there are no mismatches using standard base-pairing rules or, if the shorter of the polynucleotides is longer than 25 bases, there is no more than a 5% mismatch. Preferably, the polynucleotides are perfectly complementary (no mismatches). It can easily be demonstrated that specific hybridization conditions result in specific hybridization by carrying out a hybridization assay including negative controls (see, e.g., Shalon et al., supra, and Chee et al., Science (1996) 274:610-614).

A variety of methods are available for detection and analysis of the hybridization events. Depending on the reporter group (fluorophore, enzyme, radioisotope, etc.) used to label the DNA probe, detection and analysis are carried out fluorimetrically, colorimetrically or by autoradiography. By observing and measuring emitted radiation, such as fluorescent radiation or a particle emission, information may be obtained about the hybridization events. When fluorescently labeled probes are used, the fluorescence emissions at each site of transcript array can, preferably be detected by scanning confocal laser microscopy. In one embodiment, a separate scan, using the appropriate excitation line, is carried out for each of the two fluorophores used. Alternatively, a laser can be used that allows simultaneous specimen illumination at wavelengths specific to the two fluorophores and emissions from the two fluorophores can be analyzed simultaneously (see Shalon et al. Genome Res. (1996) 6:639-695).

As an alternative to analyzing THAP1 nucleic acids, the THAP1 protein can be evaluated (e.g. overproduction or underproduction of the protein, dysregulated expression of the protein, functional characteristics of the protein). In addition, the ability of the THAP1 protein to bind to DNA (see Example 3) can be evaluated to determine THAP1 activity.

In preferred embodiments, THAP1 protein is detected by immunoassay. For example, Western blotting permits detection of a specific variant, or the presence of THAP1 peptides. In particular, an immunoassay can detect a specific (wild-type or mutant) amino acid sequence in a THAP1 protein. Other immunoassay formats can also be used in place of Western blotting, as described below for the production of antibodies. These include enzyme-linked immunosorbent assays (ELISA).

An ELISA is a biochemical technique used to detect the presence of an antibody or an antigen in a sample. In ELISA, an unknown amount of antigen is affixed to a surface, and then a specific antibody is washed over the surface so that it can bind to the antigen. This antibody is linked to an enzyme, and in the final step a substance is added so that the enzyme can convert to some detectable signal. Thus in the case of fluorescence ELISA, when light of the appropriate wavelength is shone upon the sample, any antigen/antibody complexes will fluoresce so that the amount of antigen in the sample can be inferred through the magnitude of the fluorescence. Performing an ELISA involves at least one antibody with specificity for a particular antigen. The sample with an unknown amount of antigen is immobilized on a solid support (usually a polystyrene microtiter plate) either non-specifically (via adsorption to the surface) or specifically (via capture by another antibody specific to the same antigen, in a "sandwich" ELISA). After the antigen is immobilized the detection antibody is added, forming a complex with the antigen. The detection antibody can be covalently linked to an enzyme, or can itself be detected by a secondary antibody which is linked to an enzyme through bioconjugation. Between each step the plate is typically washed with a mild detergent solution to remove any proteins or antibodies that are not specifically bound. After the final wash step the plate is developed by adding an enzymatic substrate to produce a visible signal, which indicates the quantity of antigen in the sample. Older ELISAs utilize chromogenic substrates, though newer assays employ fluorogenic substrates enabling much higher sensitivity.

In one embodiment, an antibody against THAP1, or an epitopic fragment of THAP1 is immobilized onto a selected surface, for example, a surface capable of binding proteins such as the wells of a polystyrene microtiter plate. After washing to remove incompletely adsorbed polypeptides, a nonspecific protein such as a solution of bovine serum albumin (BSA) may be bound to the selected surface. This allows for blocking of nonspecific adsorption sites on the immobilizing surface and thus reduces the background caused by nonspecific bindings of antisera onto the surface. The immobilizing surface is then contacted with a sample, to be tested in a manner conducive to immune complex (antigen/antibody) formation. This may include diluting the sample with diluents, such as solutions of BSA, bovine gamma globulin (BGG) and/or phosphate buffered saline (PBS)/Tween. The sample is then allowed to incubate for from 2 to 4 hours, at temperatures between about 25° to 37° C. Following incubation, the sample-contacted surface is washed to remove non-immunocomplexed material. The washing procedure may include washing with a solution, such as PBS/Tween or borate buffer. Following formation of specific immunocomplexes between the test sample and the bound antibody, and subsequent washing, the occurrence, and an even amount of immunocomplex formation may be determined by subjecting the immunocomplex to a second antibody against THAP1 that recognizes a different epitope on the protein. To provide detecting means, the second antibody may have an associated activity such as an enzymatic activity that will generate, for example, a color development upon incubating with an appropriate chromogenic substrate. Quantification may then be achieved by measuring the degree of color generation using, for example, a visible spectra spectrophotometer.

Typically the detection antibody is conjugated to an enzyme such as peroxidase and the protein is detected by the addition of a soluble chromophore peroxidase substrate such as tetramethylbenzidine followed by 1 M sulfuric acid. The test protein concentration is determined by comparison with standard curves.

These protocols are detailed in Current Protocols in Molecular Biology, V. 2 Ch. 11 and Antibodies, a Laboratory Manual, Ed Harlow, David Lane, Cold Spring Harbor Laboratory (1988) pp 579-593.

Alternatively, a biochemical assay can be used to detect expression, or accumulation of THAP1 protein, e.g., by detecting the presence or absence of a band in samples analyzed by polyacrylamide gel electrophoresis; by the presence or absence of a chromatographic peak in samples analyzed by any of the various methods of high performance liquid chromatography, including reverse phase, ion exchange, and gel permeation; by the presence or absence of THAP1 in analytical capillary electrophoresis chromatography, or any other quantitative or qualitative biochemical technique known in the art.

The immunoassays discussed above involve using antibodies directed against the THAP1 protein or fragments thereof. The production of such antibodies is described below.

Anti-THAP1 Antibodies

Anti-THAP1 antibodies include but are not limited to polyclonal antibodies, monoclonal antibodies, anti-idiotypic antibodies, humanized antibodies, chimeric antibodies, single chain antibodies, antibody fragments (e.g., Fab, and $F(ab')_2$, $F_V$ variable regions, or complementarity determining regions), and a Fab expression library (see, in general, *Antibodies: A Laboratory Manual*, Harlow and Lane (eds.), Cold Spring Harbor Laboratory Press, 1988).

Various procedures known in the art may be used for the production of polyclonal antibodies to THAP1 polypeptides or derivatives or analogs thereof. For the production of antibody, various host animals can be immunized by injection with the antigenic polypeptide, including but not limited to rabbits, mice, rats, sheep, goats, etc. Generally, the peptide or a conjugated peptide (e.g., conjugated to bovine serum albumin (BSA), ovalbumin, etc.) is injected subcutaneously into rabbits, mice, other rodents or another suitable host animal. After twelve weeks, blood samples are taken and serum is separated for testing in an ELISA assay against the original peptide, with a positive result indicating the presence of antibodies specific to the target peptide. This serum can then be stored and used in ELISA assays to specifically measure the amount of the specific antimicrobial cationic peptide and/or analog or derivative thereof.

Monoclonal antibodies directed toward THAP1 may be readily generated from hybridoma cell lines using conventional techniques (see U.S. Pat. Nos. RE 32,011, 4,902,614, 4,543,439, and 4,411,993; see also *Antibodies: A Laboratory Manual*, 1988). These include but are not limited to the hybridoma technique originally developed by Kohler and Milstein (Nature 1975; 256:495-497), as well as the trioma technique, the human B-cell hybridoma technique (Kozbor et al., Immunology Today 1983; 4:72; Cote et al., Proc. Natl. Acad. Sci. U.S.A. 1983; 80:2026-2030), and the EBV-hybridoma technique to produce human monoclonal antibodies (Cole et al., in Monoclonal Antibodies and Cancer Therapy, Alan R. Liss, Inc., pp. 77-96, 1985). In an additional embodiment of the invention, monoclonal antibodies can be produced in germ-free animals (International Patent Publication No. WO 89/12690, published 28 Dec. 1989). Briefly, within one embodiment, a subject animal, such as a rat or mouse, is injected with a peptide of choice. The peptide is generally administered in an emulsion with an adjuvant, such as Freund's complete or incomplete adjuvant, which is intended to increase the immune response. The animal is generally boosted at least once prior to harvest of the spleen and/or lymph nodes and immortalization of those cells. Various immortalization techniques, such as mediated by Epstein-Barr virus or fusion to produce a hybridoma, may be used. In a preferred embodiment, immortalization occurs by fusion with a suitable myeloma cell line to create a hybridoma that secretes monoclonal antibody. Suitable myeloma lines include, for example, NS-1 (ATCC No. TIB 18), and P3×63-Ag 8.653 (ATCC No. CRL 1580). The preferred fusion partners do not express endogenous antibody genes. After about seven days, the hybridomas may be screened for the presence of antibodies that are reactive against an antimicrobial cationic peptide and analog or derivative thereof. A wide variety of assays may be utilized (see *Antibodies: A Laboratory Manual*, 1988).

Other techniques known in the art may be utilized to construct monoclonal antibodies (see Huse et al., *Science* 246: 1275-1281, 1989; Sastry et al., *Proc. Natl. Acad. Sci. USA* 86:5728-5732, 1989; Alting-Mees et al., *Strategies in Molecular Biology* 3:1-9, 1990; describing recombinant techniques). These techniques include cloning heavy and light chain immunoglobulin cDNA in suitable vectors, such as λImmunoZap(H) and λImmunoZap(L). These recombinants may be screened individually or co-expressed to form Fab fragments or antibodies (see Huse et al., supra; Sastry et al., supra). Positive plaques may subsequently be converted into non-lytic plasmids to allow high-level expression of monoclonal antibody fragments in a host, such as *E. coli*.

According to the invention, techniques described for the production of single chain antibodies (U.S. Pat. Nos. 5,476, 786 and 5,132,405 to Huston; U.S. Pat. No. 4,946,778) can be adapted to produce THAP1 polypeptide-specific single chain antibodies. Indeed, these genes can be delivered for expression in vivo. An additional embodiment of the invention utilizes the techniques described for the construction of Fab expression libraries (Huse et al., Science 1989; 246:1275-1281) to allow rapid and easy identification of monoclonal Fab fragments with the desired specificity for a THAP1 polypeptide, or its derivatives, or analogs.

Similarly, portions or fragments of antibodies, such as Fab and Fv fragments, may also be constructed utilizing conventional enzymatic digestion or recombinant DNA techniques to yield isolated variable regions of an antibody. Within one embodiment, the genes that encode the variable region from a hybridoma producing a monoclonal antibody of interest are amplified using nucleotide primers for the variable region. In addition, techniques may be utilized to change a "murine" antibody to a "human" antibody, without altering the binding specificity of the antibody to the antimicrobial cationic peptide and analog or derivative thereof.

Antibody fragments which contain the idiotype of the antibody molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment, and the Fab fragments which can be generated by treating the antibody molecule with papain and a reducing agent.

Antibodies are generally accepted as specific if they bind with a $K_d$ of greater than or equal to $10^{-7}$ M, preferably greater than of equal to $10^{-8}$ M, and more preferably greater than of equal to $10^{-9}$ M. The affinity of a monoclonal antibody or binding partner may be readily determined by one of ordinary skill in the art (see, e.g., Scatchard, Ann. N.Y. Acad. Sci. (1949) 51:660-672).

Once suitable antibodies have been identified, they may be isolated or purified by many techniques well known to those of ordinary skill in the art. In the production of antibodies, screening for the desired antibody can be accomplished by techniques known in the art, e.g., radioimmunoassay, ELISA, "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immuno-electrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention.

Kits

The invention further relates to kits for determining the presence of one or more THAP1 mutations in a biological sample from a subject. In one embodiment, the invention relates to nucleic acid-based diagnostic kits. The nucleic acid-based diagnostic kits of the invention include reagents for determining the sequence of the THAP1 gene or mRNA at particular positions in a biological sample. The sequence of the THAP1 gene or mRNA can be determined using any suitable procedure known in the art, including hybridization with specific probes for PCR amplification, restriction fragmentation, direct sequencing, SSCP, and other techniques known in the art.

A kit for determining the presence of a THAP1 mutation may comprise probe DNA. The probe DNA may be pre-labeled, for example with a fluorescent compound, a radioisotope, an enzyme or any other molecule that allows the probe to be detected; alternatively, the probe DNA may be unlabeled and the ingredients for labeling may be included in the kit. Ingredients for labeling the probe may include, for example, fluorescent compounds, radioisotopes, enzymes, and enzyme co-factors.

In one embodiment, the probe DNA comprises a nucleic acid sequence that comprises SEQ ID NO: 1, SEQ ID NO: 4, SEQ ID NO: 7 or SEQ ID NO: 8. In another embodiment, the probe DNA comprises a nucleic acid sequence that comprises SEQ ID NO: 2, SEQ ID NO: 5, or SEQ ID NO: 9. In yet another embodiment, the probe DNA comprises a nucleic acid sequence that comprises SEQ ID NO: 3, SEQ ID NO: 6 or SEQ ID NO: 10. In some embodiments, the probe DNA comprises a nucleic acid sequence that comprises the nucleic acid mutations identified in Table 1.

The probe DNA should be competent to discriminate between the wild-type THAP1 gene or transcript and a mutant THAP1 gene or transcript. One of skill in the art will understand how to modify the length and sequence of the DNA probe, as well as the hybridization conditions such as temperature, salt concentration, and detergent concentration so that the DNA probe is competent to discriminate between wild-type and mutant THAP1.

The kit may also include hybridization reagents, including solid-phase matrices, hybridization buffers or components for making hybridization buffers.

The kits of the invention may also include reagents for producing cDNA from RNA. This includes reverse transcriptase, buffer for the reverse transcriptase reaction, RNase inhibitors, deoxyribonucleotides (dATP, dCTP, dGTP, and dTTP), and primers such as oligo (dT) primers, random (hexamer) primers or gene specific primers. The kit may include reagents for isolating DNA or RNA from a subject.

In some embodiments, a kit for determining the presence of a THAP1 mutation comprises primers that may be used to amplify a region of the THAP1 gene by PCR. Such amplification primers include, for example, the primers set forth in Table 2.

The kit may include sequence determination primers. Sequence determination primers are primers that may be used to sequence a region of the THAP1 gene or transcript.

Sequence determination primers may be pre-labeled or may contain an affinity purification or attachment moiety. Exemplary sequence determination primer include the primers set forth in Table 2. The kit may further include materials needed for sequencing the THAP1 gene or transcript such as DNA polymerase, deoxyribonucleotides (e.g., dATP, dCTP, dGTP, dTTP), and deoxyribonucleotide analogs that terminate DNA elongation when incorporated. The deoxyribonucleotide analogs may be labeled to allow for detection of their incorporation.

The invention also provides antibody-based methods for detecting mutant (or wild type) THAP1 proteins in a biological sample. The methods comprise the steps of: (i) contacting a sample with one or more antibody preparations, wherein each of the antibody preparations is specific for mutant (or wild type) THAP1 under conditions in which a stable antigen-antibody complex can form between the antibody and THAP1 in the sample; and (ii) detecting any antigen-antibody complex formed in step (i) using any suitable means known in the art, wherein the detection of a complex indicates the presence of mutant (or wild type) THAP1.

Typically, immunoassays use either a labeled antibody or a labeled antigenic component (e.g., that competes with the antigen in the sample for binding to the antibody). Suitable labels include without limitation enzyme-based, fluorescent, chemiluminescent, radioactive, or dye molecules. Assays that amplify the signals from the probe are also known, such as, for example, those that utilize biotin and avidin, and enzyme-labeled immunoassays, such as ELISA assays.

Kits for detecting the presence of a THAP1 mutation may include antibodies that are capable of binding specifically to, for example, wild-type THAP1 or to mutant THAP1 such as the F81L THAP1 protein, the F45fs73 THAP1 protein, or any of the other THAP1 mutant proteins in Table 1. In one embodiment, a kit may include a purified rabbit anti-human THAP1 polyclonal antibody such as, for example, the purified rabbit anti-human THAP1 polyclonal antibody from ProteinTech Group (Chicago, Ill.). The antibodies may be pre-labeled; alternatively, the antibody may be unlabeled and the ingredients for labeling may be included in the kit. A secondary, labeled antibody that is capable of binding to the first antibody that binds wild-type or mutant THAP1 protein may also be included in the kit. In one embodiment, a kit for detecting the presence of a THAP1 mutation in a biological sample comprises an antibody that binds to a wild-type THAP1 protein comprising the amino acid sequence of SEQ ID NO: 11, but not to a mutant THAP1 protein comprising the amino acid sequence of, for example, SEQ ID NO: 12 or SEQ ID NO: 13. In another embodiment of the invention, a kit for detecting the presence of a THAP1 mutation in a biological sample comprises an antibody that binds to a mutant THAP1 protein comprising the amino acid sequence of SEQ ID NO: 12, but not to a wild-type THAP1 protein comprising the amino acid sequence of SEQ ID NO: 11. In yet another embodiment of the present invention, a kit for detecting the presence of a THAP1 mutation in a biological sample comprises an antibody that binds to a mutant THAP1 protein comprising the amino acid sequence of SEQ ID NO: 13, but not to a wild-type THAP1 protein comprising the amino acid sequence of SEQ ID NO: 11.

One of skill in the art will understand how to adjust protein/antibody binding conditions for various procedures. For example, one of skill in the art will appreciate that increasing the temperature, detergent (e.g., SDS) or salt concentration will result in more stringent conditions. In one embodiment, the following conditions can be used in the instant invention for procedures, such as Western blotting: Proteins can be resolved by SDS-PAGE (e.g., 8 µL of in vitro translated product/lane) and then can be transferred electrophoretically onto a Hybond-C nitrocellulose membrane (GE Healthcare). The membrane can be blocked with 5% nonfat dry milk diluted in Tris-buffered saline-0.2% Tween 20 and incubated successively with the primary antibody (e.g., anti-V5, 1:5000 in blocking buffer) overnight at 4° C. and with a secondary antibody (e.g, an anti-mouse horseradish peroxidase-conjugated secondary antibody; 1:3000; GE Healthcare) for 1 h at room temperature. Immunoreactivity can be detected with an enhanced chemiluminescence method (ECL detection reagent; GE Healthcare).

The kit may contain reaction components for immunoassays using the antibodies described above, including solid-phase matrices, standards, or reagents that allow for detection of the antibody or second labeled antibody.

The kits referred to above may include instructions for conducting the test. Furthermore, in preferred embodiments, the diagnostic kits are adaptable to high-throughput and/or automated operation.

DEFINITIONS

The following definitions are provided for clarity and illustrative purposes only, and are not intended to limit the scope of the invention.

Conservative Amino Acid Substitution

Among the common amino acids, a "conservative amino acid substitution" is illustrated, for example, by a substitution among amino acids within each of the following groups: (1) glycine, alanine, valine, leucine, and isoleucine, (2) phenylalanine, tyrosine, and tryptophan, (3) serine and threonine, (4) aspartate and glutamate, (5) glutamine and asparagine, and (6) lysine, arginine and histidine, or a combination thereof.

The amino acid designations are herein set forth as either the standard one- or three-letter code. Unless otherwise indicated, a named amino acid refers to the L-enantiomer. Polar amino acids include asparagine (Asp or N) and glutamine (Gln or Q); as well as basic amino acids such as arginine (Arg or R), lysine (Lys or K), histidine (His or H), and derivatives thereof; and acidic amino acids such as aspartic acid (Asp or D) and glutamic acid (Glu or E), and derivatives thereof. Hydrophobic amino acids include tryptophan (Tip or W), phenylalanine (Phe or F), isoleucine (Ile or I), leucine (Leu or L), methionine (Met or M), valine (Val or V), and derivatives thereof; as well as other non-polar amino acids such as glycine (Gly or G), alanine (Ala or A), proline (Pro or P), and derivatives thereof. Amino acids of intermediate polarity include serine (Ser or S), threonine (Thr or T), tyrosine (Tyr or Y), cysteine (Cys or C), and derivatives thereof. A capital letter indicates an L-enantiomer amino acid; a small letter indicates a D-enantiomer amino acid. Variants may also include modified amino acids, including 2,3-diamino butyric acid, 3- or 4-mercaptoproline derivatives, $N^5$-acetyl-$N^5$-hydroxy-L-ornithine, and α-N-hydroxyamino acids. Other modified amino acids will be known to those of skill in the art.

Dystonia

As used herein, "dystonia" refers to a disease characterized by twisting movements and abnormal postures. DYT6 dystonia refers to a form of dystonia that is inherited in an autosomal dominant (AD) manner and that is a primary form of dystonia, where dystonia is the only neurologic feature (de Carvalho Aguiar, P. M. and Ozelius, L. J., *Lancet Neurol.* (2002) 1: 316-25). DYT6 dystonia is inherited with penetrance of about 60% independent of gender. It is characterized by an average onset age of 16.1 years, cranial or cervical presentation in about half of the cases and frequent progression to involve multiple body regions.

Proband

"Proband" as used herein means the individual or member of a family being studied in a genetic investigation and is often the the first affected family member who seeks medical attention for a genetic disorder.

Founder Mutation

As used herein, a "founder mutation" refers to a mutation that appears in the DNA of one or more individuals who are founders of a distinct population.

Single Nucleotide Polymorphism (SNP)

As used herein, a "single nucleotide polymorphism", or SNP, refers to a DNA sequence variation that occurs when a single nucleotide—adenine, guanine, thymine, or cytosine—in the genome or other shared sequence differs, for example, between the members of a species, between members of a population, or between paired chromosomes in an individual.

Express and Expression

The terms "express" and "expression" mean allowing or causing the information in a gene or DNA sequence to become manifest, for example producing a protein by activating the cellular functions involved in transcription and translation of a corresponding gene or DNA sequence. A DNA sequence is expressed in or by a cell to form an "expression product" such as a protein. The expression product itself, e.g., the resulting protein, may also be said to be "expressed" by the cell. An expression product can be characterized as intracellular, extracellular or secreted. The term "intracellular" means something that is inside a cell. The term "extracellular" means something that is outside a cell. A substance is "secreted" by a cell if it appears in significant measure outside the cell, from somewhere on or inside the cell.

Transfection

The term "transfection" means the introduction of a foreign nucleic acid into a cell. The term "transformation" means the introduction of a "foreign" (i.e. extrinsic or extracellular) gene, DNA or RNA sequence to a cell, so that the host cell will express the introduced gene or sequence to produce a desired substance, typically a protein or enzyme coded by the introduced gene or sequence. The introduced gene or sequence may also be called a "cloned" or "foreign" gene or sequence, may include regulatory or control sequences, such as start, stop, promoter, signal, secretion, or other sequences used by a cells genetic machinery. The gene or sequence may include nonfunctional sequences or sequences with no known function. A host cell that receives and expresses introduced DNA or RNA has been "transformed" and is a "transformant" or a "clone". The DNA or RNA introduced to a host cell can come from any source, including cells of the same genus or species as the host cell, or cells of a different genus or species. In certain embodiments of the present invention, for example, MFB-F11 mouse fibroblast cells are stably transfected with a reporter plasmid consisting of TGF-β-responsive Smad-binding elements coupled to a secreted alkaline phosphatase reporter gene (SBE-SEAP).

Electroporation

"Electroporation", as used herein, is a significant increase in the electrical conductivity and permeability of the cell plasma membrane caused by an externally applied electrical field. It is usually used in molecular biology as a way of introducing some substance into a cell, such as loading it with a molecular probe, a drug that can change the cell's function, or a piece of coding DNA.

Expression System

The term "expression system" means a host cell and compatible vector under suitable conditions, e.g. for the expression of a protein coded for by foreign DNA carried by the vector and introduced to the host cell.

Gene or Structural Gene

The term "gene", also called a "structural gene" means a DNA sequence that codes for or corresponds to a particular sequence of amino acids which comprise all or part of one or more proteins or enzymes, and may or may not include regulatory DNA sequences, such as promoter sequences, which determine for example the conditions under which the gene is expressed. Some genes, which are not structural genes, may be transcribed from DNA to RNA, but are not translated into an amino acid sequence. Other genes may function as regulators of structural genes or as regulators of DNA transcription.

A coding sequence is "under the control of" or "operatively associated with" expression control sequences in a cell when RNA polymerase transcribes the coding sequence into RNA, particularly mRNA, which is then trans-RNA spliced (if it contains introns) and translated into the protein encoded by the coding sequence.

The term "expression control sequence" refers to a promoter and any enhancer or suppression elements that combine to regulate the transcription of a coding sequence. In a preferred embodiment, the element is an origin of replication.

Protein, Peptide or Polypeptide

The definitions of protein, peptide and polypeptide are well-known in the art. The term "protein", as used herein, is synonymous with the term "peptide" or "polypeptide", and is understood to mean a chain of amino acids arranged linearly and joined together by peptide bonds between the carboxyl and amino groups of adjacent amino acid residues.

Heterologous

The term "heterologous" refers to a combination of elements not naturally occurring. For example, heterologous DNA refers to DNA not naturally located in the cell, or in a chromosomal site of the cell. Preferably, the heterologous DNA includes a gene foreign to the cell. For example, the present invention includes chimeric DNA molecules that comprise a DNA sequence and a heterologous DNA sequence which is not part of the DNA sequence. A heterologous expression regulatory element is such an element that is operatively associated with a different gene than the one it is operatively associated with in nature. In the context of the present invention, a gene encoding a protein of interest is heterologous to the vector DNA in which it is inserted for cloning or expression, and it is heterologous to a host cell containing such a vector, in which it is expressed.

Homologous

The term "homologous" as used in the art commonly refers to the relationship between nucleic acid molecules or proteins that possess a "common evolutionary origin," including nucleic acid molecules or proteins within superfamilies (e.g., the immunoglobulin superfamily) and nucleic acid molecules or proteins from different species (Reeck et al., Cell 1987; 50: 667). Such nucleic acid molecules or proteins have sequence homology, as reflected by their sequence similarity, whether in terms of substantial percent similarity or the presence of specific residues or motifs at conserved positions.

Host Cell

The term "host cell" means any cell of any organism that is selected, modified, transformed, grown or used or manipulated in any way for the production of a substance by the cell. For example, a host cell may be one that is manipulated to express a particular gene, a DNA or RNA sequence, a protein or an enzyme. Host cells can further be used for screening or other assays that are described infra. Host cells may be cultured in vitro or one or more cells in a non-human animal (e.g., a transgenic animal or a transiently transfected animal). Suitable host cells include but are not limited to *Streptomyces* species and *E. coli*.

Treating or Treatment

"Treating" or "treatment" of a state, disorder or condition includes:

(1) Preventing or delaying the appearance of clinical or sub-clinical symptoms of the state, disorder or condition developing in a mammal that may be afflicted with or predisposed to the state, disorder or condition but does not yet experience or display clinical or subclinical symptoms of the state, disorder or condition; or (2) Inhibiting the state, disorder or condition, i.e., arresting, reducing or delaying the development of the disease or a relapse thereof (in case of maintenance treatment) or at least one clinical or sub-clinical symptom thereof; or (3) Relieving the disease, i.e., causing regression of the state, disorder or condition or at least one of its clinical or sub-clinical symptoms.

The benefit to a subject to be treated is either statistically significant or at least perceptible to the patient or to the physician.

Patient or Subject

"Patient" or "subject" refers to mammals and includes human and veterinary subjects.

Therapeutically Effective Amount

A "therapeutically effective amount" means the amount of a compound that, when administered to a mammal for treating a state, disorder or condition, is sufficient to effect such treatment. The "therapeutically effective amount" will vary depending on the compound, the disease and its severity and the age, weight, physical condition and responsiveness of the mammal to be treated.

Prophylactically Effective Amount

A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

About or Approximately

The term "about" or "approximately" means within an acceptable range for the particular value as determined by one of ordinary skill in the art, which will depend in part on how the value is measured or determined, e.g., the limitations of the measurement system. For example, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Unless otherwise stated, the term 'about' means within an acceptable error range for the particular value.

Include or Comprise

As used herein, the terms "include" and "comprise" are used synonymously. It should be understood that the terms "a" and "an" as used herein refer to "one or more" of the enumerated components. The use of the alternative (e.g., "or") should be understood to mean either one, both, or any combination thereof of the alternatives.

Purified

The term "purified" as used herein refers to material that has been isolated under conditions that reduce or eliminate the presence of unrelated materials, i.e. contaminants, including native materials from which the material is obtained. The isolated material is preferably substantially free of cell or culture components, including tissue culture components, contaminants, and the like. As used herein, the term "substantially free" is used operationally, in the context of analytical testing of the material. Preferably, purified material substantially free of contaminants is at least 50% pure; more preferably, at least 90% pure, and more preferably still at least 99% pure. Purity can be evaluated by chromatography, gel electrophoresis, immunoassay, composition analysis, biological assay, and other methods known in the art.

Mutant

As used herein, the terms "mutant" and "mutation" refer to any detectable change in genetic material (e.g., DNA) or any process, mechanism, or result of such a change. This includes gene mutations, in which the structure (e.g., DNA sequence) of a gene is altered, any gene or DNA arising from any mutation process, and any expression product (e.g., protein or enzyme) expressed by a modified gene or DNA sequence. As used herein, the term "mutating" refers to a process of creating a mutant or mutation.

Nucleic Acid Hybridization

The term "nucleic acid hybridization" refers to anti-parallel hydrogen bonding between two single-stranded nucleic acids, in which A pairs with T (or U if an RNA nucleic acid) and C pairs with G. Nucleic acid molecules are "hybridizable" to each other when at least one strand of one nucleic acid molecule can form hydrogen bonds with the complementary bases of another nucleic acid molecule under defined stringency conditions. Stringency of hybridization is determined, e.g., by (i) the temperature at which hybridization and/or washing is performed, and (ii) the ionic strength and (iii) concentration of denaturants such as formamide of the hybridization and washing solutions, as well as other parameters. Hybridization requires that the two strands contain substantially complementary sequences. Depending on the stringency of hybridization, however, some degree of mismatches may be tolerated. Under "low stringency" conditions, a greater percentage of mismatches are tolerable (i.e., will not prevent formation of an anti-parallel hybrid). See Molecular Biology of the Cell, Alberts et al., 3rd ed., New York and London: Garland Publ., 1994, Ch. 7.

Typically, hybridization of two strands at high stringency requires that the sequences exhibit a high degree of complementarity over an extended portion of their length. Examples of high stringency conditions include: hybridization to filter-bound DNA in 0.5 M $NaHPO_4$, 7% SDS, 1 mM EDTA at 65° C., followed by washing in 0.1×SSC/0.1% SDS at 68° C. (where 1×SSC is 0.15M NaCl, 0.15M Na citrate) or for oligonucleotide molecules washing in 6×SSC/0.5% sodium pyrophosphate at about 37° C. (for 14 nucleotide-long oligos), at about 48° C. (for about 17 nucleotide-long oligos), at about 55° C. (for 20 nucleotide-long oligos), and at about 60° C. (for 23 nucleotide-long oligos)). Accordingly, the term "high stringency hybridization" refers to a combination of solvent and temperature where two strands will pair to form a "hybrid" helix only if their nucleotide sequences are almost perfectly complementary (see Molecular Biology of the Cell, Alberts et al., 3rd ed., New York and London: Garland Publ., 1994, Ch. 7).

Conditions of intermediate or moderate stringency (such as, for example, an aqueous solution of 2×SSC at 65° C.; alternatively, for example, hybridization to filter-bound DNA in 0.5 M NaHPO4, 7% SDS, 1 mM EDTA at 65° C., and washing in 0.2×SSC/0.1% SDS at 42° C.) and low stringency (such as, for example, an aqueous solution of 2×SSC at 55° C.), require correspondingly less overall complementarity for hybridization to occur between two sequences. Specific temperature and salt conditions for any given stringency hybridization reaction depend on the concentration of the target DNA and length and base composition of the probe, and are normally determined empirically in preliminary experiments, which are routine (see Southern, J. Mol. Biol. 1975; 98: 503; Sambrook et al., Molecular Cloning: A Laboratory Manual, 2nd ed., vol. 2, ch. 9.50, CSH Laboratory Press, 1989; Ausubel et al. (eds.), 1989, Current Protocols in Molecular Biology, Vol. I, Green Publishing Associates, Inc., and John Wiley & Sons, Inc., New York, at p. 2.10.3).

As used herein, the term "standard hybridization conditions" refers to hybridization conditions that allow hybridization of sequences having at least 75% sequence identity. According to a specific embodiment, hybridization conditions of higher stringency may be used to allow hybridization of only sequences having at least 80% sequence identity, at least 90% sequence identity, at least 95% sequence identity, or at least 99% sequence identity.

Nucleic acid molecules that "hybridize" to any desired nucleic acids of the present invention may be of any length. In one embodiment, such nucleic acid molecules are at least 10, at least 15, at least 20, at least 30, at least 40, at least 50, and at least 70 nucleotides in length. In another embodiment, nucleic acid molecules that hybridize are of about the same length as the particular desired nucleic acid.

Techniques to isolate and modify specific nucleic acids and proteins are well known to those of skill in the art. In accordance with the present disclosure there may be employed conventional molecular biology, microbiology, and recombinant DNA techniques within the skill of the art. Such techniques are explained fully in the literature. See, e.g., Sambrook, Fritsch & Maniatis, Molecular Cloning: A Laboratory Manual, Second Edition. Cold Spring Harbor, N.Y.: Cold Spring Harbor Laboratory Press, 1989 (herein "Sambrook et al., 1989"); DNA Cloning: A Practical Approach, Volumes I and II (D. N. Glover ed. 1985); Oligonucleotide Synthesis (M. J. Gait ed. 1984); Nucleic Acid Hybridization [B. D. Hames & S. J. Higgins eds. (1985)]; Transcription And Translation [B. D. Hames & S. J. Higgins, eds. (1984)]; Animal Cell Culture [R. I. Freshney, ed. (1986)]; Immobilized Cells And Enzymes [IRL Press, (1986)]; B. Perbal, A Practical Guide To Molecular Cloning (1984); Ausubel, F. M. et al. (eds.). Current Protocols in Molecular Biology. John Wiley & Sons, Inc., 1994. These techniques include site directed mutagenesis employing oligonucleotides with altered nucleotides for generating PCR products with mutations (e.g., the "Quikchange" kit manufactured by Stratagene).

Oligonucleotide Preparation

Oligonucleotides can be prepared by any suitable method, including direct chemical synthesis by a method such as the phosphotriester method of Narang et al., 1979, Meth. Enzymol. 68:90-99; the phosphodiester method of Brown et al., 1979, Meth. Enzymol. 68:109-151; the diethylphosphoramidite method of Beaucage et al., 1981, Tetrahedron Lett. 22:1859-1862; and the solid support method of U.S. Pat. No. 4,458,066, each incorporated herein by reference. A review of synthesis methods of conjugates of oligonucleotides and modified nucleotides is provided in Goodchild, 1990, Bioconjugate Chemistry 1(3): 165-187, incorporated herein by reference.

Complementary

As used herein, "complementary" refers to a nucleic acid molecule that can form hydrogen bond(s) with another nucleic acid molecule by either traditional Watson-Crick base pairing or other non-traditional types of pairing (e.g., Hoogsteen or reversed Hoogsteen hydrogen bonding) between complementary nucleosides or nucleotides.

Target Sequence, Region or Nucleic Acid

The terms "target, "target sequence", "target region", and "target nucleic acid," as used herein, are synonymous and refer to a region or subsequence of a nucleic acid which is to be amplified or detected.

Amplification Reaction

The term "amplification reaction" refers to any chemical reaction, including an enzymatic reaction, which results in increased copies of a template nucleic acid sequence or results in transcription of a template nucleic acid. Amplification reactions include reverse transcription and the polymerase chain reaction (PCR), including Real Time PCR (see U.S. Pat. Nos. 4,683,195 and 4,683,202; PCR Protocols: A Guide to Methods and Applications (Innis et al., eds, 1990)). Exemplary "amplification reactions conditions" or "amplification conditions" typically comprise either two or three step cycles. Two step cycles have a denaturation step followed by a hybridization/elongation step. Three step cycles comprise a denaturation step followed by a hybridization step followed by a separate elongation step.

Reaction Mixture

The term "reaction mixture," as used herein, refers to a solution containing reagents necessary to carry out a given reaction. An "amplification reaction mixture", which refers to a solution containing reagents necessary to carry out an amplification reaction, typically contains oligonucleotide primers and a DNA polymerase or ligase in a suitable buffer. A "PCR reaction mixture" typically contains oligonucleotide primers, a DNA polymerase (most typically a thermostable DNA polymerase), dNTPs, and a divalent metal cation in a suitable buffer. A reaction mixture is referred to as complete if it contains all reagents necessary to enable the reaction, and incomplete if it contains only a subset of the necessary reagents. It will be understood by one of skill in the art that reaction components are routinely stored as separate solutions, each containing a subset of the total components, for reasons of convenience, storage stability, or to allow for application-dependent adjustment of the component concentrations, and that reaction components are combined prior to the reaction to create a complete reaction mixture. Furthermore, it will be understood by one of skill in the art that reaction components are packaged separately for commercialization and that useful commercial kits may contain any subset of the reaction components which includes the blocked primers of the disclosure.

Ligation and Ligase

The term "ligation" as used herein refers to the covalent joining of two polynucleotide ends. In various embodiments, ligation involves the covalent joining of a 3' end of a first polynucleotide (the acceptor) to a 5' end of a second polynucleotide (the donor). Ligation results in a phosphodiester bond being formed between the polynucleotide ends. In various embodiments, ligation may be mediated by any enzyme, chemical, or process that results in a covalent joining of the polynucleotide ends. In certain embodiments, ligation is mediated by a ligase enzyme.

As used herein, "ligase" refers to an enzyme that is capable of covalently linking the 3' hydroxyl group of a nucleotide to the 5' phosphate group of a second nucleotide. Examples of ligases include *E. coli* DNA ligase, T4 DNA ligase, etc.

The ligation reaction can be employed in DNA amplification methods such as the "ligase chain reaction" (LCR), also referred to as the "ligase amplification reaction" (LAR), see Barany, Proc. Natl. Acad. Sci., 88:189 (1991); and Wu and Wallace, Genomics 4:560 (1989) incorporated herein by reference. In LCR, four oligonucleotides, two adjacent oligonucleotides which uniquely hybridize to one strand of the target DNA, and a complementary set of adjacent oligonucleotides, that hybridize to the opposite strand are mixed and DNA ligase is added to the mixture. Provided that there is complete complementarity at the junction, ligase will covalently link each set of hybridized molecules. Importantly, in LCR, two probes are ligated together only when they base-pair with sequences in the target sample, without gaps or mismatches. Repeated cycles of denaturation, hybridization and ligation amplify a short segment of DNA. LCR has also been used in combination with PCR to achieve enhanced detection of single-base changes, see Segev, PCT Public. No. WO9001069 A1 (1990).

Orthologs

As used herein, the term "orthologs" refers to genes in different species that apparently evolved from a common ancestral gene by speciation. Normally, orthologs retain the same function through the course of evolution. Identification of orthologs can provide reliable prediction of gene function in newly sequenced genomes. Sequence comparison algorithms that can be used to identify orthologs include without limitation BLAST, FASTA, DNA Strider, and the GCG pileup program. Orthologs often have high sequence similarity. The present invention encompasses all orthologs of the desired protein.

Operatively Associated

By "operatively associated with" is meant that a target nucleic acid sequence and one or more expression control sequences (e.g., promoters) are physically linked so as to permit expression of the polypeptide encoded by the target nucleic acid sequence within a host cell.

Percent Sequence Similarity or Percent Sequence Identity

The terms "percent (%) sequence similarity", "percent (%) sequence identity", and the like, generally refer to the degree of identity or correspondence between different nucleotide sequences of nucleic acid molecules or amino acid sequences of proteins that may or may not share a common evolutionary origin (see Reeck et al., supra). Sequence identity can be determined using any of a number of publicly available sequence comparison algorithms, such as BLAST, FASTA, DNA Strider, GCG (Genetics Computer Group, Program Manual for the GCG Package, Version 7, Madison, Wis.), etc.

To determine the percent identity between two amino acid sequences or two nucleic acid molecules, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are, or are about, of the same length. The percent identity between two sequences can be determined using techniques similar to those described below, with or without allowing gaps. In calculating percent sequence identity, typically exact matches are counted.

The determination of percent identity between two sequences can be accomplished using a mathematical algorithm. A non-limiting example of a mathematical algorithm utilized for the comparison of two sequences is the algorithm of Karlin and Altschul, Proc. Natl. Acad. Sci. USA 1990, 87:2264, modified as in Karlin and Altschul, Proc. Natl. Acad. Sci. USA 1993, 90:5873-5877. Such an algorithm is incorporated into the NBLAST and XBLAST programs of Altschul et al., J. Mol. Biol. 1990; 215: 403. BLAST nucleotide searches can be performed with the NBLAST program, score=100, wordlength=12, to obtain nucleotide sequences homologous to sequences of the invention. BLAST protein searches can be performed with the XBLAST program, score=50, wordlength=3, to obtain amino acid sequences homologous to protein sequences of the invention. To obtain gapped alignments for comparison purposes, Gapped BLAST can be utilized as described in Altschul et al., Nucleic Acids Res. 1997, 25:3389. Alternatively, PSI-Blast can be used to perform an iterated search that detects distant relationship between molecules. See Altschul et al. (1997) supra. When utilizing BLAST, Gapped BLAST, and PSI-Blast programs, the default parameters of the respective programs (e.g., XBLAST and NBLAST) can be used. See ncbi.nlm.nih.gov/BLAST/ on the WorldWideWeb. Another non-limiting example of a mathematical algorithm utilized for the comparison of sequences is the algorithm of Myers and Miller, CABIOS 1988; 4: 11-17. Such an algorithm is incorporated into the ALIGN program (version 2.0), which is part of the GCG sequence alignment software package. When utilizing the ALIGN program for comparing amino acid sequences, a PAM120 weight residue table, a gap length penalty of 12, and a gap penalty of 4 can be used.

In a preferred embodiment, the percent identity between two amino acid sequences is determined using the algorithm of Needleman and Wunsch (J. Mol. Biol. 1970, 48:444-453), which has been incorporated into the GAP program in the GCG software package (Accelrys, Burlington, Mass.; available at accelrys.com on the WorldWideWeb), using either a Blossum 62 matrix or a PAM250 matrix, a gap weight of 16, 14, 12, 10, 8, 6, or 4, and a length weight of 1, 2, 3, 4, 5, or 6. In yet another preferred embodiment, the percent identity between two nucleotide sequences is determined using the GAP program in the GCG software package using a NWSgapdna.CMP matrix, a gap weight of 40, 50, 60, 70, or 80, and a length weight of 1, 2, 3, 4, 5, or 6. A particularly preferred set of parameters (and the one that can be used if the practitioner is uncertain about what parameters should be applied to determine if a molecule is a sequence identity or homology limitation of the invention) is using a Blossum 62 scoring matrix with a gap open penalty of 12, a gap extend penalty of 4, and a frameshift gap penalty of 5.

In addition to the cDNA sequences encoding various desired proteins, the present invention further provides polynucleotide molecules comprising nucleotide sequences having certain percentage sequence identities to any of the aforementioned sequences. Such sequences preferably hybridize under conditions of moderate or high stringency as described above, and may include species orthologs.

Pharmaceutically Acceptable

When formulated in a pharmaceutical composition, a therapeutic compound of the present invention can be admixed with a pharmaceutically acceptable carrier or excipient. As used herein, the phrase "pharmaceutically acceptable" refers to molecular entities and compositions that are generally believed to be physiologically tolerable and do not typically produce an allergic or similar untoward reaction, such as gastric upset, dizziness and the like, when administered to a human.

Pharmaceutically Acceptable Derivative

The term "pharmaceutically acceptable derivative" as used herein means any pharmaceutically acceptable salt, solvate or prodrug, e.g. ester, of a compound of the invention, which upon administration to the recipient is capable of providing (directly or indirectly) a compound of the invention, or an active metabolite or residue thereof. Such derivatives are recognizable to those skilled in the art, without undue experimentation. Nevertheless, reference is made to the teaching of Burger's Medicinal Chemistry and Drug Discovery, 5th Edition, Vol 1: Principles and Practice, which is incorporated herein by reference to the extent of teaching such derivatives. Preferred pharmaceutically acceptable derivatives are salts, solvates, esters, carbamates, and phosphate esters. Particularly preferred pharmaceutically acceptable derivatives are salts, solvates, and esters. Most preferred pharmaceutically acceptable derivatives are salts and esters.

Pharmaceutical Compositions and Administration

While it is possible to use a composition provided by the present invention for therapy as is, it may be preferable to administer it in a pharmaceutical formulation, e.g., in admixture with a suitable pharmaceutical excipient, diluent, or carrier selected with regard to the intended route of administration and standard pharmaceutical practice. Accordingly, in one aspect, the present invention provides a pharmaceutical composition or formulation comprising at least one active composition, or a pharmaceutically acceptable derivative thereof, in association with a pharmaceutically acceptable excipient, diluent, and/or carrier. The excipient, diluent and/or carrier must be "acceptable" in the sense of being compatible with the other ingredients of the formulation and not deleterious to the recipient thereof.

The compositions of the invention can be formulated for administration in any convenient way for use in human or veterinary medicine.

Pharmaceutical Carrier

The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Alternatively, the carrier can be a solid dosage form carrier, including but not limited to one or more of a binder (for compressed pills), a glidant, an encapsulating agent, a flavorant, and a colorant. Suitable pharmaceutical carriers are described in "Remington's Pharmaceutical Sciences" by E. W. Martin (1990, Mack Publishing Co., Easton, Pa. 18042).

In one embodiment, the pharmaceutical composition is conveniently administered as a liquid oral formulation. Although there are no physical limitations to delivery of the formulation, oral delivery is preferred because of its ease and convenience, and because oral formulations readily accommodate additional mixtures, such as milk, yogurt, and infant formula. Other oral dosage forms are well known in the art and include tablets, caplets, gelcaps, capsules, and medical foods. Tablets, for example, can be made by well-known compression techniques using wet, dry, or fluidized bed granulation methods.

Such oral formulations may be presented for use in a conventional manner with the aid of one or more suitable excipients, diluents, and carriers. Pharmaceutically acceptable excipients assist or make possible the formation of a dosage form for a bioactive material and include diluents, binding agents, lubricants, glidants, disintegrants, coloring agents, and other ingredients. Preservatives, stabilizers, dyes and even flavoring agents may be provided in the pharmaceutical composition. Examples of preservatives include sodium benzoate, ascorbic acid and esters of p-hydroxybenzoic acid. Antioxidants and suspending agents may be also used. An excipient is pharmaceutically acceptable if, in addition to performing its desired function, it is non-toxic, well tolerated upon ingestion, and does not interfere with absorption of bioactive materials.

Acceptable excipients, diluents, and carriers for therapeutic use are well known in the pharmaceutical art, and are described, for example, in Remington: The Science and Practice of Pharmacy. Lippincott Williams & Wilkins (A. R. Gennaro edit. 2005). The choice of pharmaceutical excipient, diluent, and carrier can be selected with regard to the intended route of administration and standard pharmaceutical practice.

The invention also encompasses pharmaceutical compositions and vaccines. The pharmaceutical compositions and vaccine compositions of the invention include at least one of the compositions of the invention, a suitable antigen (for vaccines), and a pharmaceutically acceptable carrier or excipient. Methods of formulating pharmaceutical compositions and vaccines are well-known to those of ordinary skill in the art, as described in Remington's, supra.

Formulations

The compositions, vaccines and formulations of the present invention may comprise pharmaceutically acceptable diluents, preservatives, solubilizers, emulsifiers, adjuvants and/or carriers. Such compositions include diluents of various buffer content (e.g., Tris-HCl, acetate, phosphate), pH and ionic strength; additives such as detergents and solubilizing agents (e.g., Tween 80, Polysorbate 80), anti-oxidants (e.g., ascorbic acid, sodium metabisulfite), preservatives (e.g., Thimersol, benzyl alcohol) and bulking substances (e.g., lactose, mannitol); incorporation of the material into particulate preparations of polymeric compounds such as polylactic acid, polyglycolic acid, etc. or into liposomes. Hylauronic acid may also be used. See, e.g., Remington's Pharmaceutical Sciences, 18th Ed. (1990, Mack Publishing Co., Easton, Pa. 18042) pages 1435 1712 which are herein incorporated by reference.

Contemplated for use herein are oral solid dosage forms, which are described generally in Remington's Pharmaceutical Sciences, 18th Ed. 1990 (Mack Publishing Co. Easton Pa. 18042) at Chapter 89, which is herein incorporated by reference. Solid dosage forms include tablets, capsules, pills, troches or lozenges, cachets, pellets, powders, or granules. Also, liposomal or proteinoid encapsulation may be used to formulate the present compositions (as, for example, proteinoid microspheres reported in U.S. Pat. No. 4,925,673). Liposomal encapsulation may be used and the liposomes may be derivatized with various polymers (e.g., U.S. Pat. No. 5,013,556). A description of possible solid dosage forms for the therapeutic is given by Marshall, K. In: Modern Pharmaceutics Edited by G. S. Banker and C. T. Rhodes Chapter 10, 1979, herein incorporated by reference. In general, the formulation will include the therapeutic agent and inert ingredients which allow for protection against the stomach environment, and release of the biologically active material in the intestine.

Also contemplated for use herein are liquid dosage forms for oral administration, including pharmaceutically acceptable emulsions, solutions, suspensions, and syrups, which may contain other components including inert diluents; adjuvants, wetting agents, emulsifying and suspending agents; and sweetening, flavoring, coloring, and perfuming agents.

For oral formulations, the location of release may be the stomach, the small intestine (the duodenum, the jejunem, or the ileum), or the large intestine. One skilled in the art has available formulations which will not dissolve in the stomach, yet will release the material in the duodenum or elsewhere in the intestine, e.g., by the use of an enteric coating. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic (i.e. powder), for liquid forms a soft gelatin shell may be used. The shell material of cachets could be thick starch or other edible paper. For pills, lozenges, molded tablets or tablet triturates, moist massing techniques can be used. The formulation of the material for capsule administration could also be as a powder, lightly compressed plugs, or even as tablets. These therapeutics could be prepared by compression.

One may dilute or increase the volume of the therapeutic agent with an inert material. These diluents could include carbohydrates, especially mannitol, lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic agent into a solid dosage form. Materials used as disintegrates include but are not limited to starch, including the commercial disintegrant based on starch, Explotab, Sodium starch glycolate, Amberlite, sodium carboxymethylcellulose, ultramylopectin, sodium alginate, gelatin, orange peel, acid carboxymethyl cellulose, natural sponge and bentonite may all be used. The disintegrants may also be insoluble cationic exchange resins. Powdered gums may be used as disintegrants and as binders and can include powdered gums such as agar, Karaya or tragacanth. Alginic acid and its sodium salt are also useful as disintegrants. Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the peptide (or derivative).

An antifrictional agent may be included in the formulation to prevent sticking during the formulation process. Lubricants may be used as a layer between the peptide (or derivative) and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties drug during formulation and to aid rearrangement during compression might be added. The glidants may include starch, talc, pyrogenic silica and hydrated silicoaluminate.

To aid dissolution of the therapeutic agent into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethomium chloride. The list of potential nonionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the protein or derivative either alone or as a mixture in different ratios.

Controlled release oral formulations may used in practicing the present invention. The therapeutic agent could be incorporated into an inert matrix which permits release by either diffusion or leaching mechanisms, e.g., gums. Slowly degenerating matrices may also be incorporated into the formulation. Some enteric coatings also have a delayed release effect. Another form of a controlled release is by a method based on the Oros therapeutic system (Alza Corp.), i.e. the therapeutic agent is enclosed in a semipermeable membrane which allows water to enter and push agent out through a single small opening due to osmotic effects.

Other coatings may be used for the formulation. These include a variety of sugars which could be applied in a coating pan. The therapeutic agent could also be given in a film coated tablet and the materials used in this instance are divided into 2 groups. The first are the nonenteric materials and include methyl cellulose, ethyl cellulose, hydroxyethyl cellulose, methylhydroxy-ethyl cellulose, hydroxypropyl cellulose, hydroxypropyl-methyl cellulose, sodium carboxy-methyl cellulose, providone and the polyethylene glycols. The second group consists of the enteric materials that are commonly esters of phthalic acid. A mix of materials might be used to provide the optimum film coating. Film coating may be carried out in a pan coater or in a fluidized bed or by compression coating.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants, preserving, wetting, emulsifying, and dispersing agents. The pharmaceutical compositions may be sterilized by, for example, filtration through a bacteria retaining filter, by incorporating sterilizing agents into the compositions, by irradiating the compositions, or by heating the compositions. They can also be manufactured using sterile water, or some other sterile injectable medium, immediately before use.

Dosage

The dosage of the therapeutic formulation or vaccine of the present invention will vary widely, depending upon the nature of the disease, the patient's medical history, the frequency of administration, the manner of administration, the clearance of the agent from the host, and the like. The initial dose may be larger, followed by smaller maintenance doses. The dose may be administered as infrequently as weekly or biweekly, or fractionated into smaller doses and administered daily, semiweekly, etc., to maintain an effective dosage level.

Following methodologies which are well-established in the art, effective doses and toxicity of the compounds, vaccines and compositions of the instant invention, which performed well in in vitro tests, are then determined in preclinical studies using small animal models (e.g., mice or rats) in which the tumor-associated antigens, dendritic cells, polypeptides, apoptotic cells, TLR adjuvants or agonists, apoptotic cell-associated agents, pharmaceutical, or vaccine compositions have been found to be therapeutically effective and in which these drugs can be administered by the same route proposed for the human clinical trials.

For any pharmaceutical composition or vaccine used in the methods of the invention, the therapeutically effective dose can be estimated initially from animal models. Dose-response curves derived from animal systems are then used to determine testing doses for the initial clinical studies in humans. In safety determinations for each composition, the dose and frequency of administration should meet or exceed those anticipated for use in the clinical trial.

As disclosed herein, the dose of the components in the compositions, vaccines and formulations of the present invention is determined to ensure that the dose administered continuously or intermittently will not exceed an amount determined after consideration of the results in test animals and the individual conditions of a patient. A specific dose naturally varies depending on the dosage procedure, the conditions of a patient or a subject animal such as age, body weight, sex, sensitivity, feed, dosage period, drugs used in combination, and seriousness of the disease. The appropriate dose and dosage times under certain conditions can be determined by the test based on the above-described indices but may be refined and ultimately decided according to the judgment of the practitioner and each patient's circumstances (age, general condition, severity of symptoms, sex, etc.) according to standard clinical techniques. DC are loaded with apoptotic cells or TLR-ligand carrying apoptotic cells or apoptotic cells carrying inactivated microbes at a ratio of 1 DC to 2 apoptotic cells. DC vaccines will be administered every 28 to 30 days at 1-12×10$^6$ DCs/vaccination. As a safety measure, vaccination may be initialized at 1×10$^6$ DC/vaccination for the first 4 vaccines. If no toxicity is observed, after completion of 4 vaccinations, doses may be increased to 4×10$^6$ DC, and finally to a maximum of 12×10$^6$ DC/vaccine. These are suggested guidelines based on DC vaccinations of patients with metastatic melanoma in the study by Palucka et al. (2006) J Immunother; 29:545-57. Actual dosage and composition or pharmaceutical formulations of TLR ligands in combination with apoptotic cell-associated agents may be determined in pre-clinical and clinical trials by standard practices known in the art.

Toxicity and therapeutic efficacy of the compositions, vaccines, and formulations of the invention can be determined by standard pharmaceutical procedures in experimental animals, e.g., by determining the LD50 (the dose lethal to 50% of the population) and the ED50 (the dose therapeutically effective in 50% of the population). The dose ratio between therapeutic and toxic effects is the therapeutic index and it can be expressed as the ratio ED50/LD50. Compositions that exhibit large therapeutic indices are preferred.

The data obtained from animal studies can be used in formulating a range of doses for use in humans. The therapeutically effective doses of in humans lay preferably within a range of circulating concentrations that include the ED50 with little or no toxicity. The dosage can vary within this range depending upon the dosage form employed and the route of administration utilized. Ideally, a single dose of each drug should be used daily.

The abbreviations in the specification correspond to units of measure, techniques, properties or compounds as follows: "min" means minutes, "h" means hour(s), "µl" means microliter(s), "ml" means milliliter(s), "mM" means millimolar, "M" means molar, "mmole" means millimole(s), "kb" means kilobase, "bp" means base pair(s), and "IU" means International Units. "Polymerase chain reaction" is abbreviated PCR; "Reverse transcriptase polymerase chain reaction" is abbreviated RT-PCR; "DNA binding domain" is abbreviated DBD; "Untranslated region" is abbreviated UTR; "Sodium dodecyl sulfate" is abbreviated SDS; and "High Pressure Liquid Chromatography" is abbreviated HPLC.

Examples

The following examples are included to demonstrate certain embodiments of the invention. These specific examples are described solely for purposes of illustration, and are not intended to limit the scope of this disclosure. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention. Although specific targets, terms, and values have been employed herein, such targets, terms, and values will likewise be understood as exemplary and non-limiting to the scope of this invention.

Example 1

Materials and Methods

Materials

In all Examples, all chemicals were obtained from Sigma-Aldrich (St. Louis, Mo.), unless otherwise indicated. DNA restriction enzymes and DNA modifying enzymes were obtained from New England BioLabs (Beverly, Mass.).

Patients

All study subjects (or parent/guardian if the study subject was less than 18 years of age) gave informed consent prior to participation, and the study was approved by Beth Israel Medical Center and Mount Sinai School of Medicine institutional review boards. Videotaped examinations and determination of affected status was undertaken as described in Bressman, S. B. et al., Ann. Neurol. (1989) 26: 612-20, which is hereby incorporated by reference in its entirety. Clinical details of affected individuals in all families analyzed (families M, C, R, W and S) are given in Table 4.

Control samples included unrelated spouses from Amish-Mennonite dystonia families (n=55), unrelated Amish-Mennonites from Dr. Jonathan Haines (n=85), CEPH controls (n=77) and Human Random DNA control samples representing UK healthy Caucasian blood donors (Sigma-Aldrich) (n=95).

TABLE 4

Clinical Characteristics of 29 THAP1 Patients from Five Families

| | Gender | Age onset (yrs) | Age exam (yrs) | SITES INVOLVED ||||||||
|---|---|---|---|---|---|---|---|---|---|---|---|
| | | | | upper face | lower face | neck | larynx | pharynx | tongue | jaw | right arm |
| 416 | F | 13 | 42 | | • | • | • | | • | • | • |
| 413 | M | 13 | 46 | • | • | • | | | • | • | • |
| 411 | M | 9 | 47 | | • | • | | | | • | |
| 302 | F | 13 | 79 | • | • | • | | | • | • | • |

TABLE 4-continued

Clinical Characteristics of 29 THAP1 Patients from Five Families

| ID | Gender | | | | | | | | | | |
|---|---|---|---|---|---|---|---|---|---|---|---|
| 303 | M | 21 | 66 | • | • | • | • | • | • | | |
| 502 | M | 9 | 13 | | | | | | | | • |
| FAMILY M | | | | | | | | | | | |
| 524 | M | 16 | 19 | | | | • | | | | |
| 212* | M | 14 | 78 | | | • | • | | | • | • |
| 309* | F | 34 | 54 | • | • | | • | • | | • | • |
| 314* | F | Unk. | 63 | | | | | | | | • |
| 319* | M | 7 | 64 | • | • | | • | • | | | • |
| 334* | F | 13 | 57 | • | • | | • | | | | • |
| 342* | F | 24 | 40 | • | • | | • | | | | • |
| 404* | F | 6 | 34 | | | • | • | | | | • |
| 417* | F | 5 | 15 | | | | | | | | • |
| 481* | M | 31 | 49 | | | | | | | | • |
| 486* | F | 28 | 45 | | | | | | | | • |
| 514* | F | 15 | 17 | | | | • | | | | • |
| 516* | F | 8 | 18 | | | | • | | • | • | • |
| 517* | F | 10 | 12 | | | | | | | | • |
| 522* | M | 10 | 23 | • | • | • | • | • | • | • | • |
| FAMILY C | | | | | | | | | | | |
| 417* | M | 38 | 55 | | | | • | • | | | • |
| 419* | F | 9 | 44 | • | • | | • | | • | • | • |
| 470* | F | 20 | 43 | • | • | | | | • | | • |
| 498* | F | 21 | 47 | • | • | | | | • | | • |
| 512* | F | 6 | 17 | | | | | | | | • |
| 526* | F | 16 | 19 | • | | | • | • | | | |
| FAMILY R | | | | | | | | | | | |
| 309* | M | 18 | 35 | • | • | • | | | | | • |
| 401* | M | 6 | 10 | | | | • | • | | • | • |

| | SITES INVOLVED | | | | Site of | | Protein |
|---|---|---|---|---|---|---|---|---|
| | left arm | right leg | left leg | trunk | Dystonia distribution | onset | Allele variant | variant |
| | | | | | | | c.241T > C | |
| 416 | • | • | | • | • | G | Cranial | |
| 413 | • | | • | • | | G | Leg | |
| 411 | | | | | | S | Cranial | |
| 302 | • | • | | • | • | G | Arm | |
| | | | | | | | c.134_135insGGGTT; 137 | |
| 303 | • | | | | | S | Cranial | |
| 502 | • | | | | | S | Arm | |
| FAMILY M | | | | | | | c.134_135insGGGTT; 137 | |
| 524 | | | | | | F | Cranial | |
| 212* | • | • | • | • | | G | Cranial | |
| 309* | | • | | | | M | Arm | |
| 314* | | | | | | F | Arm | |
| 319* | • | • | • | • | | G | Leg | |
| 334* | • | • | • | • | | G | Neck | |
| 342* | • | • | • | | | M | Cranial | |
| 404* | • | • | | • | | G | Arm | |
| 417* | | • | | | | M | Arm | |
| 481* | | | | | | F | Arm | |
| 486* | • | | | | | S | Arm | |
| 514* | | | | | | S | Neck | |
| 516* | • | • | | | | M | Arm | |
| 517* | • | • | • | | | G | Arm | |
| 522* | | | | | | S | Cranial | |
| FAMILY C | | | | | | | c.134_135insGGGTT; 137 | |
| 417* | • | | | | | S | Arm | |
| 419* | | • | | • | | G | Neck | |
| 470* | | | | | | S | Cranial | |
| 498* | | | | | | S | Cranial | |
| 512* | | | | | | S | Arm | |
| 526* | | | | | | S | Neck | |
| FAMILY R | | | | | | | c.134_135insGGGTT; 137 | F45fs73x |
| 309* | • | • | • | | | G | Cranial | |
| 401* | | • | | • | | G | Neck | |

Gender: F—female, M—male;
Dystonia distribution: G—generalized, F—focal, M—multifocal, S—segmental
*reported previously in Almasy 1997 and Saunders-Pullman 2007 and updated here.

PCR Amplification and Sequencing

DNA was extracted from white blood cells using the Purgene procedure (Gentra Systems Inc, Minneapolis, Minn.). Intron based, exon-specific primers were designed from the UCSC human genome assembly sequence (March 2006 UCSC human genome assembly genome.ucsc.edu) using Integrated DNA Technologies Primer Quest online server which is derived from Primer3 software (release 0.9) www.idtdna.com/Scitools/Applications/Primerquest/Default.aspx. Primers that may be used include, for example, the primers set forth in Table 2. Standard PCR amplification was performed using the primers set forth in Table 2 and the PCR conditions as follows: 35 cycles of 1 min at 95° C., 1 min at the annealing temperature identified in Table 2 (57° for exons 2 and 3 and 60° for exon1) and 1 min at 72° C. The first step of denaturation and the last step of extension were each 10 minutes at 95° C. and 72° C., respectively. THAP1 Exon1 sequence is GC rich and therefore the PCR reaction was performed with AccuPrime™ GC-rich DNA polymerase (Invitrogen). The PCR amplification of the other THAP1 exons was performed with Taq DNA polymerase from Applied Biosystems (ABI). The amplified fragments underwent an enzymatic cleanup process with exonuclease I and shrimp alkaline phosphatase (USB, Corporation, Cleveland, Ohio) for 15 min at 37° C. and 15 min at 85° C., followed by standard dideoxy cycle sequencing. Sequence analysis was performed using Sequencher™ version 4.8 (Gene Codes, Ann Arbor, Mich.).

Mutant Allele Cloning

PCR fragments bearing the c.134_135insGGGTT;137_139delAAC mutant allele were subcloned using the TOPO TA Cloning$^R$ Kit (Invitrogen) as described by the manufacturer and confirmed by forward and reverse sequencing. PCR was performed with THAP1 exon2 primers (Table 2) using the following PCR conditions: 35 cycles of 1 min at 95° C., 1 min at 57° C. and 1 min at 72° C. PCR products were cloned into the TOPO® vector. The products of cloning reaction were transformed into One Shot® chemically competent E. coli cells by heat-shock, bacterial culture was plated on a prewarmed LB agar plate containing 100 µg/ml spectinomycin, and incubated overnight at 37° C. Ten colonies were picked straight into PCR mixture and PCR reaction was performed following the protocol for THAP1 exon2 PCR. The products were sequenced using routine procedure to reveal either the mutant or wild type allele.

Restriction Analysis

PCR products were digested with the restriction enzymes DraI to test for a c.134_135insGGGTT;137_139delAAC mutation (e.g., SEQ ID NO: 5) or SspI to test for c.241T>C mutation (e.g., SEQ ID NO: 6). The exon 2 primers identified in Table 2 were used to generate a PCR product that was then digested with either DraI or SspI. DraI digestion of a 400 bp PCR product from wild type THAP1 results in restriction fragments of 36, 105, 113 and 146 base pairs. Digestion of a 400 bp PCR product from a c.134_135insGGGTT;137_139delAAC mutant results in restriction fragments of 36 bp, 113 bp and 251 base pairs. The c.134_135insGGGTT;137_139delAAC mutant is missing a DraI restriction site in the 251 base pair fragment. Therefore, in a heterozygous individual (one wild type and one c.134_135insGGGTT;137_139delAAC allele), a DraI digestion of the PCR products would result in restriction fragments of 36, 105, 113, 146, and 251 base pairs.

Genotyping

Figure 2:
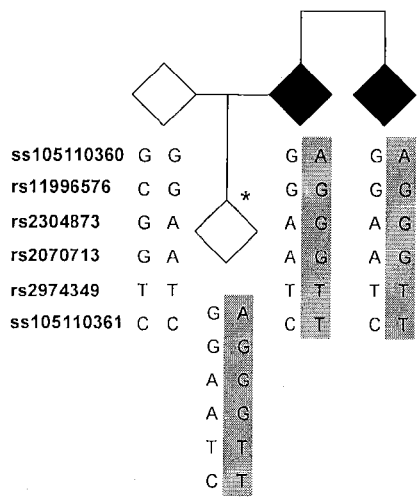
FIG. 2 shows shared haplotype in families of Mennonite origin. The pedigree of family W and fragments of family M are shown with corresponding haplotypes drawn below. All individuals are represented by diamonds for patient confidentiality. Symptomatic mutation carriers are blackened; asymptomatic mutation carriers are denoted by an asterisk. Individuals were genotyped for six SNP's and haplotypes were constructed by hand. The disease bearing haplotype, representative of the founder mutation, is highlighted in grey (SEQ ID NO: 49).
Figure 2:
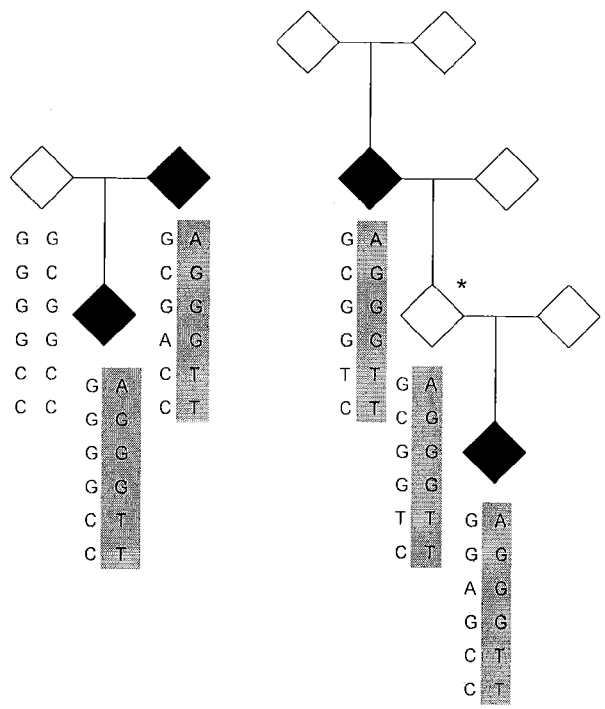
Figure 3:
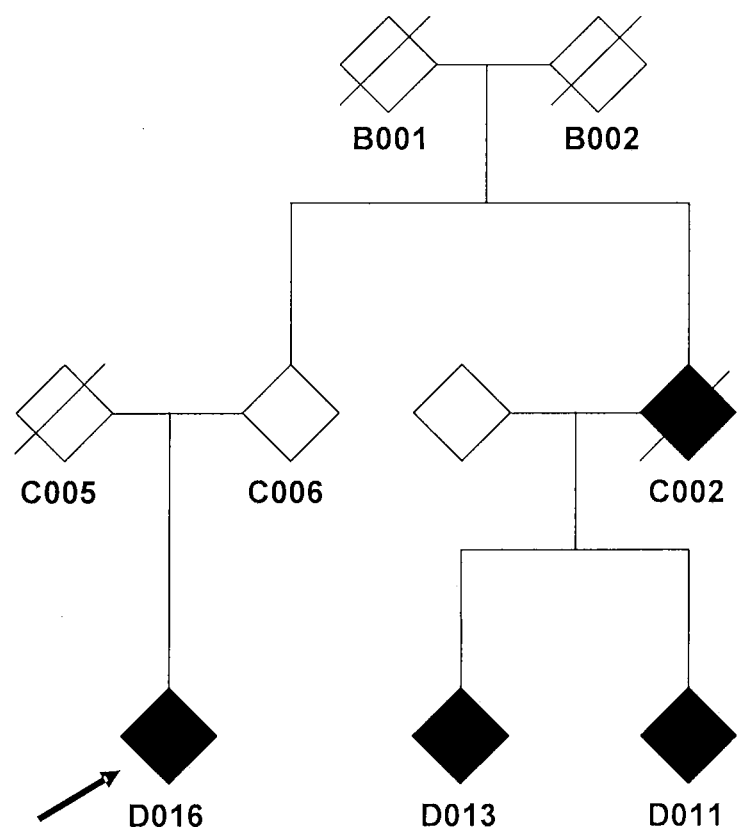
FIG. 3 shows transmission of the F81L mutation in family S. The pedigree of family S is illustrated. Filled symbols represent symptomatic mutation carriers. An arrow points to the proband.

Four reported SNPs: rs11996576, rs2304873, rs2070713, rs2974349 (dbSNP, build 28) and two novel SNPs (ss105110360 and ss105110361, dbSNP build 30) were amplified using the THAP1 exon 2 primers disclosed in Table 2 using the following PCR conditions: 35 cycles of 1 min at 95° C., 1 min at 57° C. and 1 min at 72° C. The PCR products were then sequenced. Haplotypes were constructed by hand (FIG. 2 and FIG. 3). A control frequency for the disease bearing chromosome was calculated by multiplying the individual marker allele frequencies that make up the haplotype.

Bioinformatic Analysis

Sequences of the tentative THAP1 orthologs and paralogs were withdrawn from the Gene database at NCBI. Multiple sequence alignment was performed with ClustalW[14,15] using the default parameters. Domain and Motif analysis was performed by Simple Modular Architecture Research Tool (SMART) smart.embl-heidelberg.de.

Plasmid Vectors and Antibodies

The full-length cDNA for the gene encoding human THAP1 (Ultimate ORF clone ID: IOH10776) was purchased from Invitrogen. Human THAP1 was transferred from the entry vector to the pcDNA3.1/nV5-Dest expression vector by Gateway recombinational cloning technique according to the manufacturer's instructions to introduce a V5 epitope tag at the N-terminus of THAP1, yielding pcDNA3.1/nV5-hTHAP1. The pcDNA3.1/nV5-hTHAP1-F81L mutant construct was generated by QuikChange mutagenesis (Stratagene, La Jolla, Calif.), with the forward primer 5'-AGAATGCTGTGCCCACAATAcTTCTTTG-TACTGAGCC-3' (SEQ ID NO: 18) and the reverse primer 5'-GGCTCAGTACAAAGAAgTATTGTGGGCA-CAGCATTCT-3' (SEQ ID NO: 19) (the point mutation is indicated in lower case), using the pcDNA3.1/nV5-hTHAP1 construct as template. All constructs were verified by sequencing.

The mouse monoclonal anti-V5 antibody was obtained from Invitrogen and the purified rabbit anti-Human THAP1 polyclonal antibody from ProteinTech Group (Chicago, Ill.). Secondary antibodies were purchased from GE Healthcare (Piscataway, N.J.).

In vitro Transcription/Translation

In vitro transcription/translation was performed using the TnT-coupled reticulocyte lysate system (Promega, Madison, Wis.) according to the manufacturer's instructions, with the T7 RNA polymerase promoter of the pcDNA3.1/nV5 vectors. The reactions were carried out with 1 µg of the corresponding pcDNA3.1/nV5 plasmid in 504 of lysate and incubated for 1.5 h at 30° C. Products were subjected to SDS-PAGE prior to binding assays as described below.

Cell Culture and Transfection

HEK 293T cells were grown in DMEM (GIBCO) supplemented with 10% dialyzed fetal calf serum (GIBCO) and antibiotics at 37° C. in a humidified atmosphere of 5% CO2. Cells were transfected with pcDNA3.1/nV5-hTHAP1 at 60-70% confluence by using Lipofectamine 2000 (Invitrogen), according to the manufacturer's instructions. Two days post-transfection, cells were harvested and lysed in 1% SDS. This lysate was used as a positive control in subsequent western blot analysis.

Immunoblotting

Proteins resolved by SDS-PAGE (8 µL of in vitro translated product/lane) were transferred electrophoretically onto a Hybond-C nitrocellulose membrane (GE Healthcare). The membrane was blocked with 5% nonfat dry milk diluted in Tris-buffered saline-0.2% Tween 20 and incubated successively with the primary antibody (anti-V5, 1:5000 in blocking buffer) overnight at 4° C. and with the anti-mouse horseradish peroxidase-conjugated secondary antibody (1:3000; GE Healthcare) for 1 h at room temperature. Immunoreactivity was detected with an enhanced chemiluminescence method (ECL detection reagent; GE Healthcare).

Example 2

Identification of the DYT6 Gene

The gene associated with DYT6 had previously been mapped to a 40cM (peri-centromeric) region on chromosome 8 in two Amish-Mennonite families (M and C) (Almasy, L. et al., *Ann. Neurol.* (1997) 42: 670-3), and an additional Amish-Mennonite family (R) was shown to share the DYT6 disease haplotype. All three families were descended from several "Old Order Amish" ancestral pairs (Sanders-Pullman, R. et al., *Am. J. Med. Genet. A* (2007) 143A: 2098-105). The linked region had previously been further narrowed to a 23cM region between markers D8S2317 and D8S2323; this region contains ~120 genes (March 2006 UCSC human genome assembly. genome.ucsc.edu) (Sanders-Pullman, R. et al., *Am. J. Med. Genet. A* (2007) 143A: 2098-105).

Eighteen genes in one affected individual from each of the M and C Amish-Mennonite families (see Almasy, L. et al., *Ann. Neurol.* (1997) 42: 670-3) were sequenced, including all coding exons, the 5' and 3' UTRs and at least 50 bp of upstream and downstream intronic sequence surrounding each exon. A heterozygous 5 bp (GGGTT) insertion followed by a 3 bp deletion (AAC) (c.134_135insGGGTT;137_139delAAC) in exon 2 of the THAP (Thanatos-associated protein) domain containing, apoptosis associated protein 1 (THAP1) gene, was identified in both individuals of families M and C described above. The mutation causes a frame shift at amino acid position number 44 of the protein resulting in a premature stop codon at position 73 (F45fs73X, FIG. 1A,B).

The sequence of the F45fs73X mutation was confirmed by cloning and sequencing of the mutant allele. PCR fragments bearing the c.134_135insGGGTT;137_139delAAC mutant allele obtained using the exon 2 primers set forth in Table 2 were subcloned using the TOPO TA Cloning$^R$ Kit (Invitrogen) as described by the manufacturer. The sequence of the PCR fragments was confirmed by forward and reverse sequencing.

To determine whether the mutation was associated with the DYT6 disease, we screened 23 affected individuals from the three Amish-Mennonite families M, C and R [22 previously described (Saunders-Pullman, R. et al., *Am. J. Med. Genet. A* (2007) 143A: 2098-105) and another (M-524; see Table 4) that was subsequently identified], as well as 157 family members who showed no symptoms associated with dystonia. The F45fs73X mutation completely co-segregated with the disease in all affected individuals and obligate carriers and was not present in 280 Amish-Mennonite control chromosomes.

Upon identification of the truncating mutation in THAP1, two clinically similar families with known or suspected Amish-Mennonite ancestry were screened. Family W comprised two affected individuals, the proband and his grandfather. They reported Amish-Mennonite ancestors, but a direct relationship to families M, C, or R was not established. Family S was of partial German ancestry, residing in the same region as branches of Family M; previous marker analysis was consistent with linkage to chromosome 8 (data not shown). There were four affected members in the S family with an average age onset of 12 years (range 9-13 years). Three of the affected individuals were previously reported (Family 6; see Kramer, P. L. et al., *Am. J. Hum. Genet.* (1994) 55: 468-75). The F45fs73X mutation was detected in family W and co-segregated with the disease (see FIG. 2=Supplementary FIG. 1), but this mutation was not present in family S.

To examine whether the mutation arose independently in family W or was a founder mutation, six SNPs from the THAP1 region were genotyped, and the disease bearing chromosomes from family M and W were compared. The M and W families share a haplotype A-G-G-G-T-T (SEQ ID NO: 49) (FIG. 2) that would be expected to occur in only 0.75% of control chromosomes based on the individual marker allele frequencies (dbSNP at NCBI, build 128; www.ncbi.nlm.nih.gov/sites/entrez?db=snp build 128). The haplotype results in family W confirm that the F45fs73X mutation is a founder mutation in the Amish-Mennonite population.

Since the insertion/deletion mutation was not found in family S (FIG. 3), the remainder of the THAP1 gene was sequenced for the other affected family S individuals (the remaining family S individuals were checked for the mutation by restriction enzyme digestion as described herein). Strikingly, we found a different mutation in exon 2, c.241T>C, that co-segregated with the disease in this family (FIG. 1C) but was not observed in 514 control chromosomes (154 CEPH, 170 Amish-Mennonite and 190 UK controls). The T to C substitution replaces a phenylalanine with a leucine (F81L) in a highly conserved and functionally significant AVPTIF motif (SEQ ID NO: 86) of the THAP1 protein (FIG. 1C). This finding of a different mutation in family S, as well as subsequent genealogic analysis which failed to identify Amish-Mennonite ancestry, demonstrate THAP1 as a cause of dystonia outside the Amish-Mennonite population.

Example 3

Role of F81 in DNA-Binding Activity of THAP1

The F81L missense mutation identified in Family S involves the F residue of the AVPTIF motif (SEQ ID NO: 86). Both this motif and the F81 amino acid are conserved in most orthologs of human THAP1 (FIG. 1C) and in several paralogs suggesting strong selection pressures against amino acid variations in this domain. To test the effect of the F81L mutation on the DNA-binding activity of THAP1, we performed electrophoretic mobility shift assays using the THAP-domain-binding sequence (THABS) probe 5'-AGCAAG-TAAGGGCAACTACTTCAT-3' (SEQ ID NO: 17) (Clouaire. T. et al., *Proc. Natl. Acad. Sci. U.S.A.* (2005) 102: 6907-12).

Double-stranded oligonucleotide was prepared by annealing synthetic complementary oligonucleotides (5'-AG-CAAGTAAGGGCAACTACTTCAT-3' (SEQ ID NO: 17) and the reverse complement of this oligo 5' ATGAAGTAGT-TGCCCTTACTTGCT-3' (SEQ ID NO: 48)) in 20 mM Tris/HCl (pH 7.5), 10 mM MgCl2, 50 mM NaCl, 1 mM dithiothreitol (DTT) by heating for 5 min at 95° C., and cooling to room temperature overnight. Probes were end-labeled with [gamma-$^{32}$P]ATP using T4 polynucleotide kinase. Unincorporated nucleotides were removed by column chromatography (illustra MicroSpin™ G-25 Columns, GE Healthcare), according to the manufacturer's protocol. Binding reactions were performed in 20 µl of binding buffer (20 mM Tris/HCl (pH 7.5), 150 mM KCl, 0.1% Igepal, 100 µg/mL BSA, 2.5 mM DTT, 5% glycerol, 50 µg/mL of poly(dI-dC), 50 µg/mL salmon sperm DNA and a protease inhibitor cocktail, EDTA-free) (Roche Diagnostics, Indianapolis, Ind.) containing 50,000 cpm of the $^{32}$P-labeled probe and 5 µL of in vitro translated reaction. For competition experiments, >200× excess unlabeled oligonucleotides were first added into the initial incubation reaction before adding the labeled probe. Samples were incubated at room temperature for 5 minutes, followed by a further 20 minutes in the presence of radiolabeled probe. Supershift experiments were carried out by adding 1 µg of the anti-THAP1 antibody to the binding reaction mixtures. Samples were subjected to electrophoresis on a native 4% polyacrylamide gel (acrylamide/bisacrylamide ratio 37.5:1). Following buffer at 150 V at room temperature, gels were dried and exposed to storage Phosphor screens that were scanned and analyzed using a Typhoon phosphorimager (GE Healthcare).

Wild-type human THAP1 cDNA was mutated to F81L by site-directed mutagenesis Human THAP1 was transferred from the entry vector to the pcDNA3.1/nV5-Dest expression vector by Gateway recombinational cloning technique according to the manufacturer's instructions to introduce a V5 epitope tag at the N-terminus of THAP1, yielding pcDNA3.1/nV5-hTHAP1. The pcDNA3.1/nV5-hTHAP1-F81L mutant construct was generated by QuikChange mutagenesis (Stratagene, La Jolla, Calif.), with the forward primer 5'-AGAATGCTGTGCCCACAATAcTTCTTTG-TACTGAGCC-3' (SEQ ID NO: 18) and the reverse primer 5'-GGCTCAGTACAAAGAAgTATTGTGGGCA-CAGCATTCT-3' (SEQ ID NO: 19) (the point mutation is indicated in lower case), using the pcDNA3.1/nV5-hTHAP1 construct as template. All constructs were verified by sequencing.

Figure 4:
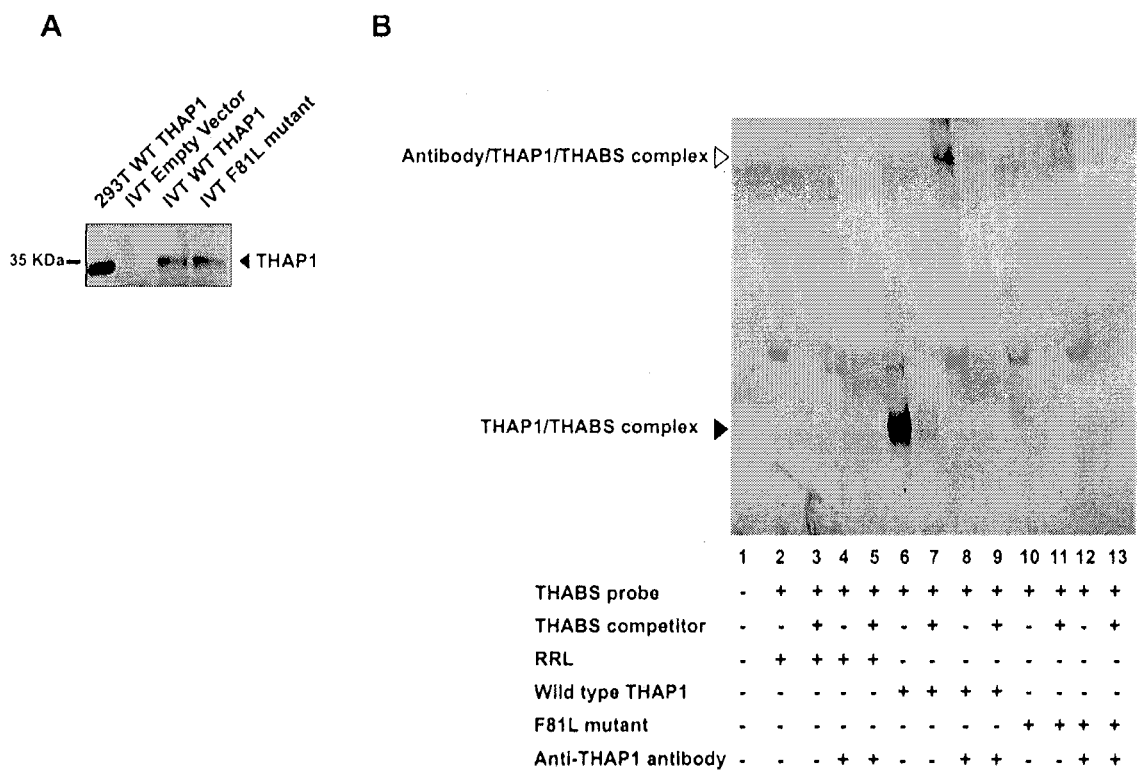
FIG. 4 shows DNA binding activity of wild type THAP1 versus the F81L mutant proteins.

The two constructs were expressed in an in vitro transcription/translation (IVTT) system and assessed by western for equal levels of protein expression (FIG. 4A). When the radiolabeled THABS probe was incubated with the IVTT wild-type THAP1, a major shifted band was detected (FIG. 4B, lane 6, arrowhead). The presence of THAP1 in the band was confirmed by its supershift with specific anti-THAP1 antibody (FIG. 4B, lane 8). The bands were competed off by unlabeled THABS oligonucleotide (FIG. 4B, lanes 7 and 9) indicating that these are specific DNA-protein interactions. The F81L mutant revealed a similar binding pattern (FIG. 4B, lanes 10 and 12), but bands were dramatically reduced in intensity compared with wild-type THAP1, indicating a reduced binding affinity to the target DNA. It is likely that both mutations identified in the DYT6 families result in the loss of DNA binding which would cause transcriptional dysregulation of downstream targets.

What is claimed is:

1. A method for detecting the presence of a THAP1 mutation in a biological sample from a human subject, comprising:
   (a) determining all or a part of a THAP1 nucleic acid coding sequence in the biological sample from the subject; and
   (b) identifying a c.85 C>T mutation in the THAP1 nucleic acid coding sequence in the biological sample from the subject, wherein the nucleotide position corresponds to position 85 of SEQ ID NO: 4.

2. The method of claim 1, wherein the determining step (a) comprises direct sequencing of all or a part of the THAP1 coding sequence.

3. The method of claim 1, wherein the determining step (a) comprises contacting genomic DNA obtained from the biological sample from the subject or cDNA produced from RNA obtained from the biological sample from the subject with a primer pair that allows for specific amplification of all or a part of the THAP1 coding sequence, under conditions permitting hybridization of the primers to the genomic DNA or cDNA; and performing an amplification reaction on the genomic DNA or cDNA.

4. The method of claim 3, wherein the primer pair is SEQ ID NO: 22 and SEQ ID NO: 22.

5. The method of claim 3, wherein the amplification is by PCR or real-time PCR.

6. The method of claim 3, wherein the determining step (a) further comprises digesting the amplified genomic DNA or cDNA with at least one restriction enzyme and comparing the restriction fragments of the amplified product from the subject with restriction fragments obtained from an amplification of a normal control sample.

* * * * *

UNITED STATES PATENT AND TRADEMARK OFFICE
CERTIFICATE OF CORRECTION

| | | |
|---|---|---|
| PATENT NO. | : 8,568,980 B2 | Page 1 of 1 |
| APPLICATION NO. | : 12/694908 | |
| DATED | : October 29, 2013 | |
| INVENTOR(S) | : Laurie Ozelius et al. | |

It is certified that error appears in the above-identified patent and that said Letters Patent is hereby corrected as shown below:

In the Specification

Replace Column 1, Lines 11 through 16 with the following paragraph:
--GOVERNMENT CLAUSE
This invention was made with government support under NS026636 awarded by The National Institutes of Health. The government has certain rights in the invention.--

Signed and Sealed this
Tenth Day of October, 2017

Joseph Matal
*Performing the Functions and Duties of the*
*Under Secretary of Commerce for Intellectual Property and*
*Director of the United States Patent and Trademark Office*

SEQUENCE LISTING

<160> NUMBER OF SEQ ID NOS: 107

<210> SEQ ID NO 1
<211> LENGTH: 2189
<212> TYPE: DNA
<213> ORGANISM: Homo sapiens

<400> SEQUENCE: 1

```
gaggttgaag ctgcctccgc catcttggag atgggagacg ggcgatggct gtggtccttc      60
tgctaatgca aacaacaaaa cgggcacact agtcaccccc gagggaggcc accatcactg     120
taactgttgg ccaaagctac aaaagaagcg agggaatcca accgagcgca gcgacactga     180
gaacagcttc ccctgccttc tgcggcggca gaagtgaagt gcctgaggac cggaaggatg     240
gtgcagtcct gctccgccta cggctgcaag aaccgctacg acaaggacaa gcccgtttct     300
ttccacaagt ttcctcttac tcgacccagt cttttgtaaag aatgggaggc agctgtcaga     360
agaaaaaact ttaaacccac caagtatagc agtatttgtt cagagcactt tactccagac     420 tgcttttaaga gagagtgcaa caacaagtta ctgaaagaga atgctgtgcc cacaatattt     480
ctttgtactg agccacatga caagaaagaa gatcttctgg agccacagga acagcttccc     540
ccacctcctt taccgcctcc tgtttcccag gttgatgctg ctattggatt actaatgccg     600
cctcttcaga cccctgttaa tctctcagtt ttctgtgacc acaactatac tgtggaggat     660
acaatgcacc agcggaaaag gattcatcag ctagaacagc aagttgaaaa actcagaaag     720
aagctcaaga ccgcacagca gcgatgcaga aggcaagaac ggcagcttga aaaattaaag     780
gaggttgttc acttccagaa agagaaagac gacgtatcag aaagaggtta tgtgattcta     840
ccaaatgact actttgaaat agttgaagta ccagcataaa aaaatgaaat gtgtattgat     900
ttctaatggg gcaataccac atatcctcct ctagcctgta aaggagtttc atttaaaaaa     960
ataacatttg attacttata taaaaacagt tcagaatatt tttttaaaaa aaattctata    1020
tatactgtaa aattataaat ttttttgttt gtaatttcag gttttttaca ttttaacaaa    1080
atattttaaa agttataaac taacctcaga cctctaatgt aagttggttt caagattggg    1140
gattttgggg ttttttttta gtatttatag aaataatgta aaaataaaaa gtaaagagaa    1200
tgagaacagt gtggtaaaag ggtgatttca gtttaaaact taaaattagt actgttttat    1260
tgagagaatt tagttatatt ttaaatcaga agtatgggtc agatcatggg acataacttc    1320
ttagaatata tatatacata tgtacatatt ctcatatgta aagtcacaag gttcatttat    1380 cttttctgaat cagttatcaa agataaattg gcaagtcagt acttaagaaa aaagatttga    1440
ttatcatcac agcagaaaaa agtcattgca tatctgatca ataacttcag attctaagag    1500
```

```
tggatttttt ttttttacat gggctcctat tttttccect actgtettge attataaaat    1560 tagaagtgta ttttcagtgg aagaaacatt tttcaataaa taaagtaagg cattgtcatc    1620
aatgaagtaa ttaaaactgg gacctgatct atgatacgct ttttctttc attacacect    1680 agctgaagga catccagttc cccagctgta gttatgtatc tgccttcaag tctctgacaa    1740
atgtgctgtg ttagtagagt ttgatttgta tcatatgata atcttgcact tgactgagtt    1800
gggacaaggc ttcacataaa aaattatttc ttcactttta acacaagtta gaaattatat    1860
cccatttagt taaatgcgtg atttatattc agaacaacct actatgtagc gtttattta     1920 ctgaatgtgg agatttaaac actgaggttt ctgttcaaac tgtgagttct gttctttgtg    1980 agaaattta catatattgg aagtgaaaat atgttctgag taaacaaata ttgctatggg     2040
agttatcttt ttagatttag aataactgtt ccaatgataa ttattacttt tatatttcaa    2100 agtcacactaa gatcgttgaa gagcaataga accttaaga cagtattaaa ggtgtgaaac    2160
aatggcaaaa aaaaaaaaaa aaaaaaaa                                       2189
```

<210> SEQ ID NO 2
<211> LENGTH: 2191
<212> TYPE: DNA
<213> ORGANISM: Homo sapiens

<400> SEQUENCE: 2

```
gaggttgaag ctgcctccgc catcttggag atgggagacg gcgatggct gtggtccttc      60 tgctaatgca acaacaaaa cgggcacact agtcacccce gagggaggec accatcactg     120 taactgttgg ccaaagctac aaaagaagcg agggaatcca accgagcgca gcgacactga    180
gaacagcttc ccctgccttc tgcggcggca gaagtgaagt gcctgaggac cggaaggatg    240
gtgcagtcct gctccgccta cggctgcaag aaccgctacg acaaggacaa gcccgttct     300 ttccacaagt ttcctcttac tcgacccagt cttgtaaag aatgggaggc agctgtcaga    360
agaaaaaact tgggtttacc accaagtata gcagtatttg ttcagagcac tttactccag    420
actgctttaa gagagagtgc aacaacaagt tactgaaaga gaatgctgtg cccacaatat    480
ttctttgtac tgagccacat gacaagaaag aagatcttct ggagccacag gaacagcttc    540
ccccacctcc tttaccgcct cctgtttccc aggttgatgc tgctattgga ttactaatgc    600
cgcctcttca gacccctgtt aatctctcag ttttctgtga ccacaactat actgtggagg    660
atacaatgca ccagcggaaa aggattcatc agctagaaca gcaagttgaa aaactcagaa    720
agaagctcaa gaccgcacag cagcgatgca gaaggcaaga acggcagctt gaaaaattaa    780
aggaggttgt tcacttccag aaagagaaag acgacgtatc agaagaggt tatgtgattc    840 taccaaatga ctactttgaa atagttgaag taccagcata aaaaaatgaa atgtgtattg    900
atttctaatg gggcaatacc acatatcctc tctagcctg taaaggagtt tcatttaaaa    960
aaataacatt tgattactta tataaaaaca gttcagaata tttttttaaa aaaaattcta   1020
tatatactgt aaaattataa atttttttgt ttgtaatttc aggttttta catttaca     1080 aaatatttta aaagttataa actaacctca gacctctaat gtaagttggt ttcaagattg   1140
gggattttgg ggtttttttt tagtatttat agaaataatg taaaaataaa agtaaagag    1200 aatgagaaca gtgtggtaaa agggtgattt cagtttaaaa cttaaaatta gtactgtttt    1260
attgagagaa tttagttata ttttaaatca gaagtatggg tcagatcatg ggacataact    1320
tcttagaata tatatataca tatgtacata ttctcatatg taaagtcaca aggttcattt    1380
atcttcctga atcagttatc aaagataaat tggcaagtca gtacttaaga aaaagatttt   1440
```

```
gattatcatc acagcagaaa aaagtcattg catatctgat caataacttc agattctaag    1500
agtggatttt ttttttttac atgggctcct atttttttccc ctactgtctt gcattataaa   1560
attagaagtg tattttcagt ggaagaaaca ttttttcaata aataaagtaa ggcattgtca   1620
tcaatgaagt aattaaaact gggacctgat ctatgatacg cttttttctt tcattacacc   1680
ctagctgaag acatccagt tccccagctg tagttatgta tctgccttca agtctctgac    1740
aaatgtgctg tgttagtaga gtttgatttg tatcatatga taatcttgca cttgactgag   1800
ttgggacaag gcttcacata aaaaattatt tcttcacttt taacacaagt tagaaattat   1860
atcccattta gttaaatgcg tgatttatat tcagaacaac ctactatgta gcgtttattt   1920
tactgaatgt ggagatttaa acactgaggt ttctgttcaa actgtgagtt ctgttctttg   1980
tgagaaattt tacatatatt ggaagtgaaa atatgttctg agtaaacaaa tattgctatg   2040
ggagttatct ttttagattt agaataactg ttccaatgat aattattact tttatatttc    2100
aaagtacact aagatcgttg aagagcaata gaacctttaa gacagtatta aaggtgtgaa    2160
acaatggcaa aaaaaaaaa aaaaaaaaa a                                     2191
```

<210> SEQ ID NO 3
<211> LENGTH: 2189
<212> TYPE: DNA
<213> ORGANISM: Homo sapiens

<400> SEQUENCE: 3

```
gaggttgaag ctgcctccgc catcttggag atgggagacg ggcgatggct gtggtccttc     60
tgctaatgca acaacaaaa cgggcacact agtcacccccc gagggaggcc accatcactg    120
taactgttgg ccaaagctac aaaagaagcg agggaatcca accgagcgca gcgacactga   180
gaacagcttc ccctgccttc tgcggcggca gaagtgaagt gcctgaggac cggaaggatg   240
gtgcagtcct gctccgccta cggctgcaag aaccgctacg acaaggacaa gcccgttttct  300 ttccacaagt ttcctcttac tcgacccagt cttgtaaag aatgggaggc agctgtcaga   360
agaaaaaact ttaaacccac caagtatagc agtatttgtt cagagcactt tactccagac   420
tgcttaagaa gagagtgcaa caacaagtta ctgaaagaga atgctgtgcc cacaatactt   480
ctttgtactg agccacatga caagaaagaa gatcttctgg agccacagga acagcttccc   540
ccacctcctt taccgcctcc tgtttcccag gttgatgctg ctattggatt actaatgccg   600
cctcttcaga cccctgttaa tctctcagtt ttctgtgacc acaactatac tgtggaggat   660
acaatgcacc agcggaaaag gattcatcag ctagaacagc aagttgaaaa actcagaaag   720
aagctcaaga ccgcacagca gcgatgcaga aggcaagaac ggcagcttga aaaattaaag   780
gaggttgttc acttccagaa agagaaagac gacgtatcag aaagaggtta tgtgattcta   840
ccaaatgact actttgaaat agttgaagta ccagcataaa aaaatgaaat gtgtattgat   900
ttctaatggg gcaataccac atatcctcct ctagcctgta aaggagtttc atttaaaaaa   960
ataacatttg attacttata taaaaacagt tcagaatatt tttttaaaaa aaattctata  1020
tatactgtaa aattataaat ttttttgttt gtaatttcag gttttttaca ttttaacaaa  1080
atattttaaa agttataaac taacctcaga cctctaatgt aagttggttt caagattggg   1140
gattttgggg tttttttta gtatttatag aaataatgta aaataaaaa gtaaagaaaa    1200 tgagaacagt gtggtaaaag ggtgatttca gtttaaaact taaaattagt actgttttat   1260
tgagagaatt tagttatatt ttaaatcaga agtatgggtc agatcatggg acataacttc   1320
ttagaatata tatatacata tgtacatatt ctcatatgta aagtcacaag gttcatttat   1380
```

```
ctttctgaat cagttatcaa agataaattg gcaagtcagt acttaagaaa aaagatttga      1440
ttatcatcac agcagaaaaa agtcattgca tatctgatca ataacttcag attctaagag      1500
tggatttttt ttttttacat gggctcctat ttttcccct actgtcttgc attataaaat      1560
tagaagtgta ttttcagtgg aagaaacatt tttcaataaa taaagtaagg cattgtcatc      1620
aatgaagtaa ttaaaactgg gacctgatct atgatacgct tttttctttc attacaccct      1680
agctgaagga catccagttc cccagctgta gttatgtatc tgccttcaag tctctgacaa      1740
atgtgctgtg ttagtagagt ttgatttgta tcatatgata atcttgcact tgactgagtt      1800
gggacaaggc ttcacataaa aaattatttc ttcacttta acacaagtta gaaattatat       1860
cccatttagt taaatgcgtg atttatattc agaacaacct actatgtagc gtttatttta      1920
ctgaatgtgg agatttaaac actgaggttt ctgttcaaac tgtgagttct gttctttgtg      1980
agaaatttta catatattgg aagtgaaaat atgttctgag taaacaaata ttgctatggg      2040
agttatcttt ttagatttag aataactgtt ccaatgataa ttattacttt tatatttcaa      2100 agtcacactaa gatcgttgaa gagcaataga acctttaaga cagtattaaa ggtgtgaaac     2160
aatggcaaaa aaaaaaaaaa aaaaaaaa                                         2189

<210> SEQ ID NO 4
<211> LENGTH: 642
<212> TYPE: DNA
<213> ORGANISM: Homo sapiens

<400> SEQUENCE: 4
atggtgcagt cctgctccgc ctacggctgc aagaaccgct acgacaagga caagcccgtt       60
tctttccaca gtttcctct tactcgaccc agtctttgta aagaatggga ggcagctgtc      120
agaagaaaaa actttaaacc caccaagtat agcagtattt gttcagagca ctttactcca     180
gactgcttta agagagagtg caacaacaag ttactgaaag agaatgctgt gcccacaata     240
tttctttgta ctgagccaca tgacaagaaa gaagatcttc tggagccaca ggaacagctt     300
cccccacctc ctttaccgcc tcctgttttcc caggttgatg ctgctattgg attactaatg    360
ccgcctcttc agacccctgt taatctctca gttttctgtg accacaacta tactgtggag    420
gatacaatgc caccgcggaa aaggattcat cagctagaac agcaagttga aaaactcaga    480
aagaagctca agaccgcaca gcagcgatgc agaaggcaag aacggcagct tgaaaaatta    540
aaggaggttg ttcacttcca gaaagagaaa gacgacgtat cagaaagagg ttatgtgatt    600
ctaccaaatg actactttga aatagttgaa gtaccagcat aa                       642

<210> SEQ ID NO 5
<211> LENGTH: 644
<212> TYPE: DNA
<213> ORGANISM: Homo sapiens

<400> SEQUENCE: 5
atggtgcagt cctgctccgc ctacggctgc aagaaccgct acgacaagga caagcccgtt       60
tctttccaca gtttcctct tactcgaccc agtctttgta aagaatggga ggcagctgtc      120
agaagaaaaa acttgggttt accaccaagt atagcagtat tgttcagag cactttactc      180 cagactgctt taagagagag tgcaacaaca agttactgaa agagaatgct gtgcccacaa     240
tacttctttg tactgagcca catgacaaga agaagatct ctggagccca caggaacagc     300
ttcccccacc tcctttaccg cctcctgttt cccaggttga tgctgctatt ggattactaa    360
tgccgcctct tcagacccct gttaatctct cagttttctg tgaccacaac tatactgtgg    420
```

-continued

```
aggatacaat gcaccagcgg aaaaggattc atcagctaga acagcaagtt gaaaaactca    480
gaaagaagct caagaccgca cagcagcgat gcagaaggca agaacggcag cttgaaaaat    540
taaaggaggt tgttcacttc cagaaagaga aagacgacgt atcagaaaga ggttatgtga    600
ttctaccaaa tgactacttt gaaatagttg aagtaccagc ataa                     644
```

<210> SEQ ID NO 6
<211> LENGTH: 642
<212> TYPE: DNA
<213> ORGANISM: Homo sapiens

<400> SEQUENCE: 6

```
atggtgcagt cctgctccgc ctacggctgc aagaaccgct acgacaagga caagcccgtt     60
tctttccaca gtttcctct tactcgaccc agtctttgta aagaatggga ggcagctgtc    120
agaagaaaaa actttaaacc caccaagtat agcagtattt gttcagagca ctttactcca    180
gactgcttta agagagagtg caacaacaag ttactgaaag agaatgctgt gcccacaata    240
cttctttgta ctgagccaca tgacaagaaa gaagatcttc tggagccaca ggaacagctt    300
cccccacctc cttaccgcc tcctgttttcc caggttgatg ctgctattgg attactaatg    360
ccgcctcttc agacccctgt taatctctca gttttctgtg accacaacta tactgtggag    420
gatacaatgc accagcggaa aaggattcat cagctagaac agcaagttga aaaactcaga    480
aagaagctca agaccgcaca gcagcgatgc agaaggcaag aacggcagct gaaaaatta     540 aaggaggtt tcacttcca gaagagaaa gacgacgtat cagaaagagg ttatgtgatt      600
ctaccaaatg actactttga aatagttgaa gtaccagcat aa                       642
```

<210> SEQ ID NO 7
<211> LENGTH: 8
<212> TYPE: DNA
<213> ORGANISM: Homo sapiens

<400> SEQUENCE: 7

```
tttaaacc                                                              8
```

<210> SEQ ID NO 8
<211> LENGTH: 9
<212> TYPE: DNA
<213> ORGANISM: Homo sapiens

<400> SEQUENCE: 8

```
atatttctt                                                             9
```

<210> SEQ ID NO 9
<211> LENGTH: 10
<212> TYPE: DNA
<213> ORGANISM: Homo sapiens

<400> SEQUENCE: 9

```
ttgggtttac                                                           10
```

<210> SEQ ID NO 10
<211> LENGTH: 9
<212> TYPE: DNA
<213> ORGANISM: Homo sapiens

<400> SEQUENCE: 10

```
atacttctt                                                             9
```

```
<210> SEQ ID NO 11
<211> LENGTH: 213
<212> TYPE: PRT
<213> ORGANISM: Homo sapiens

<400> SEQUENCE: 11

Met Val Gln Ser Cys Ser Ala Tyr Gly Cys Lys Asn Arg Tyr Asp Lys
1               5                   10                  15

Asp Lys Pro Val Ser Phe His Lys Phe Pro Leu Thr Arg Pro Ser Leu
            20                  25                  30

Cys Lys Glu Trp Glu Ala Ala Val Arg Arg Lys Asn Phe Lys Pro Thr
        35                  40                  45

Lys Tyr Ser Ser Ile Cys Ser Glu His Phe Thr Pro Asp Cys Phe Lys
    50                  55                  60

Arg Glu Cys Asn Asn Lys Leu Leu Lys Glu Asn Ala Val Pro Thr Ile
65                  70                  75                  80

Phe Leu Cys Thr Glu Pro His Asp Lys Lys Glu Asp Leu Leu Glu Pro
                85                  90                  95

Gln Glu Gln Leu Pro Pro Pro Leu Pro Pro Val Ser Gln Val
            100                 105                 110

Asp Ala Ala Ile Gly Leu Leu Met Pro Pro Leu Gln Thr Pro Val Asn
        115                 120                 125

Leu Ser Val Phe Cys Asp His Asn Tyr Thr Val Glu Asp Thr Met His
130                 135                 140

Gln Arg Lys Arg Ile His Gln Leu Glu Gln Gln Val Glu Lys Leu Arg
145                 150                 155                 160

Lys Lys Leu Lys Thr Ala Gln Gln Arg Cys Arg Arg Gln Glu Arg Gln
                165                 170                 175

Leu Glu Lys Leu Lys Glu Val Val His Phe Gln Lys Gly Lys Asp Asp
            180                 185                 190

Val Ser Glu Arg Gly Tyr Val Ile Leu Pro Asn Asp Tyr Phe Glu Ile
        195                 200                 205

Val Glu Val Pro Ala
    210

<210> SEQ ID NO 12
<211> LENGTH: 72
<212> TYPE: PRT
<213> ORGANISM: Homo sapiens

<400> SEQUENCE: 12

Met Val Gln Ser Cys Ser Ala Tyr Gly Cys Lys Asn Arg Tyr Asp Lys
1               5                   10                  15

Asp Lys Pro Val Ser Phe His Lys Phe Pro Leu Thr Arg Pro Ser Leu
            20                  25                  30

Cys Lys Glu Trp Glu Ala Ala Val Arg Arg Lys Asn Leu Gly Leu Pro
        35                  40                  45

Pro Ser Ile Ala Val Phe Val Gln Ser Thr Leu Leu Gln Thr Ala Leu
    50                  55                  60

Arg Glu Ser Ala Thr Thr Ser Tyr
65                  70

<210> SEQ ID NO 13
<211> LENGTH: 213
<212> TYPE: PRT
<213> ORGANISM: Homo sapiens

<400> SEQUENCE: 13
```

-continued

```
Met Val Gln Ser Cys Ser Ala Tyr Gly Cys Lys Asn Arg Tyr Asp Lys
1               5                   10                  15

Asp Lys Pro Val Ser Phe His Lys Phe Pro Leu Thr Arg Pro Ser Leu
            20                  25                  30

Cys Lys Glu Trp Glu Ala Ala Val Arg Arg Lys Asn Phe Lys Pro Thr
        35                  40                  45

Lys Tyr Ser Ser Ile Cys Ser Glu His Phe Thr Pro Asp Cys Phe Lys
    50                  55                  60

Arg Glu Cys Asn Asn Lys Leu Leu Lys Glu Asn Ala Val Pro Thr Ile
65                  70                  75                  80

Leu Leu Cys Thr Glu Pro His Asp Lys Lys Asp Leu Leu Glu Pro
                85                  90                  95

Gln Glu Gln Leu Pro Pro Pro Leu Pro Pro Val Ser Gln Val
                100                 105                 110

Asp Ala Ala Ile Gly Leu Leu Met Pro Pro Leu Gln Thr Pro Val Asn
            115                 120                 125

Leu Ser Val Phe Cys Asp His Asn Tyr Thr Val Glu Asp Thr Met His
    130                 135                 140

Gln Arg Lys Arg Ile His Gln Leu Glu Gln Gln Val Glu Lys Leu Arg
145                 150                 155                 160

Lys Lys Leu Lys Thr Ala Gln Gln Arg Cys Arg Arg Gln Glu Arg Gln
                165                 170                 175

Leu Glu Lys Leu Lys Glu Val Val His Phe Gln Lys Glu Lys Asp Asp
            180                 185                 190

Val Ser Glu Arg Gly Tyr Val Ile Leu Pro Asn Asp Tyr Phe Glu Ile
        195                 200                 205

Val Glu Val Pro Ala
    210
```

<210> SEQ ID NO 14
<211> LENGTH: 8
<212> TYPE: PRT
<213> ORGANISM: Homo sapiens

<400> SEQUENCE: 14

```
Pro Thr Ile Phe Leu Cys Thr Glu
1               5
```

<210> SEQ ID NO 15
<211> LENGTH: 28
<212> TYPE: PRT
<213> ORGANISM: Homo sapiens

<400> SEQUENCE: 15

```
Leu Gly Leu Pro Pro Ser Ile Ala Val Phe Val Gln Ser Thr Leu Leu
1               5                   10                  15

Gln Thr Ala Leu Arg Glu Ser Ala Thr Thr Ser Tyr
            20                  25
```

<210> SEQ ID NO 16
<211> LENGTH: 8
<212> TYPE: PRT
<213> ORGANISM: Homo sapiens

<400> SEQUENCE: 16

```
Pro Thr Ile Leu Leu Cys Thr Glu
1               5
```

<210> SEQ ID NO 17

```
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 17
agcaagtaag ggcaactact tcat                                          24

<210> SEQ ID NO 18
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
agaatgctgt gcccacaata cttctttgta ctgagcc                             37

<210> SEQ ID NO 19
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ggctcagtac aaagaagtat tgtgggcaca gcattct                             37

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
tgttccagga gcgcgagaaa                                                20

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
aaacacctgg cctcagccaa ta                                             22

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
tcctaagctg gaaagtttgg gtgc                                           24

<210> SEQ ID NO 23
<211> LENGTH: 26
<212> TYPE: DNA
```

-continued

```
<213> ORGANISM: Artificial Sequence
<220> FEATURE:
<223> OTHER INFORMATION: Description of Artificial Sequence: Synthetic
      primer

<400> SEQUENCE: 23
cactgttaac tacaaggttc caggca                                        26

<210> SEQ ID NO 24
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gcctggtcag tccacagatt ctt                                           23

<210> SEQ ID NO 25
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
actcctttac aggctagagg aggata                                        26

<210> SEQ ID NO 26
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
aggcaagaac ggcagcttga aa                                            22

<210> SEQ ID NO 27
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
aactggatgt ccttcagcta gggt                                          24

<210> SEQ ID NO 28
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
agtatgggtc agatcatggg aca                                           23

<210> SEQ ID NO 29
<211> LENGTH: 22
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 29
agccttgtcc caactcagtc aa                                              22

<210> SEQ ID NO 30
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
actgggacct gatctatgat acgct                                           25

<210> SEQ ID NO 31
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
tgaatcacag tgctatccac tggc                                            24

<210> SEQ ID NO 32
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
ccaccaagta tagcagtatt tattcagagc actttactcc                           40

<210> SEQ ID NO 33
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
ggagtaaagt gctctgaata aatactgcta tacttggtgg                           40

<210> SEQ ID NO 34
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
gacaagcccg tttctttcta caagtttcct cttactc                              37

<210> SEQ ID NO 35
<211> LENGTH: 37
<212> TYPE: DNA
<213> ORGANISM: Artificial Sequence
<220> FEATURE:
<223> OTHER INFORMATION: Description of Artificial Sequence: Synthetic
      primer
```

-continued

<400> SEQUENCE: 35
gagtaagagg aaacttgtag aaagaaacgg gcttgtc    37

<210> SEQ ID NO 36
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
gtactgagcc acatgacagg aaagaagatc ttctgga    37

<210> SEQ ID NO 37
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
tccagaagat cttctttcct gtcatgtggc tcagtac    37

<210> SEQ ID NO 38
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
gcctacggct gcaagaaacg ctacgacaag g    31

<210> SEQ ID NO 39
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
ccttgtcgta gcgtttcttg cagccgtagg c    31

<210> SEQ ID NO 40
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
agctgtcaga agaaaaaact tgggtttacc accaagtata gcag    44

<210> SEQ ID NO 41
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41 aagtttttc ttctgacagc tgcctcccat tctttacaaa gac                        43

<210> SEQ ID NO 42
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
cacaagtttc ctcttactcc acccagtctt tgtaaagaa                            39

<210> SEQ ID NO 43
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
ttctttacaa agactgggtg gagtaagagg aaacttgtg                            39

<210> SEQ ID NO 44
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
caaggacaag cccgttactt tccacaagtt tcct                                 34

<210> SEQ ID NO 45
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
aggaaacttg tggaaagtaa cgggcttgtc cttg                                 34

<210> SEQ ID NO 46
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
ggaaaaggat tcatcagcta gaaagcaagt tgaaaaactc ag                        42

<210> SEQ ID NO 47
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
ctgagttttt caacttgctt tctagctgat gaatcctttt cc                        42

<210> SEQ ID NO 48
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 48
atgaagtagt tgcccttact tgct                                             24

<210> SEQ ID NO 49
<211> LENGTH: 6
<212> TYPE: DNA
<213> ORGANISM: Homo sapiens

<400> SEQUENCE: 49 agggtt                                                                  6

<210> SEQ ID NO 50
<211> LENGTH: 642
<212> TYPE: DNA
<213> ORGANISM: Homo sapiens

<400> SEQUENCE: 50
atggtgcagt cctgctccgc ctacggctgc aagaaccgct acgacaagga caagcccgtt      60
tctttccaca gtttcctct tacttgaccc agtctttgta aagaatggga ggcagctgtc     120
agaagaaaaa actttaaacc caccaagtat agcagtattt gttcagagca ctttactcca    180
gactgcttta agagagagtg caacaacaag ttactgaaag agaatgctgt gcccacaata    240
tttctttgta ctgagccaca tgacaagaaa gaagatcttc tggagccaca ggaacagctt    300
cccccacctc ctttaccgcc tcctgttttc caggttgatg ctgctattgg attactaatg    360
ccgcctcttc agaccctgt taatctctca gttttctgtg accacaacta tactgtggag     420
gatacaatgc accagcggaa aaggattcat cagctagaac agcaagttga aaaactcaga    480
aagaagctca agaccgcaca gcagcgatgc agaaggcaag aacggcagct tgaaaaatta    540
aaggaggttg ttcacttcca gaaagagaaa gacgacgtat cagaaagagg ttatgtgatt    600
ctaccaaatg actactttga aatagttgaa gtaccagcat aa                       642

<210> SEQ ID NO 51
<211> LENGTH: 642
<212> TYPE: DNA
<213> ORGANISM: Homo sapiens

<400> SEQUENCE: 51
atggtgcagt cctgctccgc ctacggctgc aagaaccgct acgacaagga caagcccgtt      60
tctttccaca gtttcctct tactccaccc agtctttgta aagaatggga ggcagctgtc     120
agaagaaaaa actttaaacc caccaagtat agcagtattt gttcagagca ctttactcca    180
gactgcttta agagagagtg caacaacaag ttactgaaag agaatgctgt gcccacaata    240
tttctttgta ctgagccaca tgacaagaaa gaagatcttc tggagccaca ggaacagctt    300
cccccacctc ctttaccgcc tcctgttttc caggttgatg ctgctattgg attactaatg    360
ccgcctcttc agaccctgt taatctctca gttttctgtg accacaacta tactgtggag     420
gatacaatgc accagcggaa aaggattcat cagctagaac agcaagttga aaaactcaga    480
aagaagctca agaccgcaca gcagcgatgc agaaggcaag aacggcagct tgaaaaatta    540

| | |
|---|---|
| aaggaggttg ttcacttcca gaaagagaaa gacgacgtat cagaaagagg ttatgtgatt | 600 |
| ctaccaaatg actactttga aatagttgaa gtaccagcat aa | 642 |

```
<210> SEQ ID NO 52
<211> LENGTH: 642
<212> TYPE: DNA
<213> ORGANISM: Homo sapiens

<400> SEQUENCE: 52
```

| | |
|---|---|
| atggtgcagt cctgctccgc ctacggctgc aagaaccgct acgacaagga caagcccgtt | 60 |
| tctttccaca gtttcctct tactcgaccc agtctttgta aagaatggga ggcagctgtc | 120 |
| agaagaaaaa actttaaacc caccaagtat agcagtattt gttcagagca ctttactcca | 180 |
| gactgcttta agagagagtg caacaacaag ttactgaaag agaatgctgt gcccacaata | 240 |
| tttctttgta ctgagccaca tgacaggaaa aagatcttc tggagccaca ggaacagctt | 300 |
| cccccacctc ctttaccgcc tcctgttttcc caggttgatg ctgctattgg attactaatg | 360 |
| ccgcctcttc agacccctgt taatctctca gttttctgtg accacaacta tactgtggag | 420 |
| gatacaatgc accagcggaa aaggattcat cagctagaac agcaagttga aaaactcaga | 480 |
| aagaagctca agaccgcaca gcagcgatgc agaaggcaag aacggcagct tgaaaaatta | 540 |
| aaggaggttg ttcacttcca gaaagagaaa gacgacgtat cagaaagagg ttatgtgatt | 600 |
| ctaccaaatg actactttga aatagttgaa gtaccagcat aa | 642 |

```
<210> SEQ ID NO 53
<211> LENGTH: 642
<212> TYPE: DNA
<213> ORGANISM: Homo sapiens

<400> SEQUENCE: 53
```

| | |
|---|---|
| atggtgcagt cctgctccgc ctacggctgc aagaaccgct acgacaagga caagcccgtt | 60 |
| tctttccaca gtttcctct tactcgaccc agtctttgta aagaatggga ggcaactgtc | 120 |
| agaagaaaaa actttaaacc caccaagtat agcagtattt gttcagagca ctttactcca | 180 |
| gactgcttta agagagagtg caacaacaag ttactgaaag agaatgctgt gcccacaata | 240 |
| tttctttgta ctgagccaca tgacaagaaa aagatcttc tggagccaca ggaacagctt | 300 |
| cccccacctc ctttaccgcc tcctgttttcc caggttgatg ctgctattgg attactaatg | 360 |
| ccgcctcttc agacccctgt taatctctca gttttctgtg accacaacta tactgtggag | 420 |
| gatacaatgc accagcggaa aaggattcat cagctagaac agcaagttga aaaactcaga | 480 |
| aagaagctca agaccgcaca gcagcgatgc agaaggcaag aacggcagct tgaaaaatta | 540 |
| aaggaggttg ttcacttcca gaaagagaaa gacgacgtat cagaaagagg ttatgtgatt | 600 |
| ctaccaaatg actactttga aatagttgaa gtaccagcat aa | 642 |

```
<210> SEQ ID NO 54
<211> LENGTH: 641
<212> TYPE: DNA
<213> ORGANISM: Homo sapiens

<400> SEQUENCE: 54
```

| | |
|---|---|
| atggtgcagt cctgctccgc ctacggctgc aagaaccgct acgacaagga caagcccgtt | 60 |
| tctttccaca gtttcctct tactcgaccc agtctttgta aagaatggga ggcagctgtc | 120 |
| agaagaaaaa actttaaacc caccaagtat agcagtattt gttcagagca ctttactcca | 180 |
| gactgcttta agagagagtg caacaacaag ttactgaaag agaatgctgt gcccacaata | 240 |

```
tttctttgta ctgagccaca tgacaagaaa gaagatcttc tggagccaca ggaacagctt    300
cccccacctc ctttaccgcc tcctgttccc caggttgatg ctgctattgg attactaatg    360
ccgcctcttc agacccctgt taatctctca gttttctgtg accacaacta tactgtggag    420
gatacaatgc accagcggaa aaggattcat cagctagaaa gcaagttgaa aaactcagaa    480
agaagctcaa gaccgcacag cagcgatgca gaaggcaaga acggcagctt gaaaaattaa    540
aggaggttgt tcacttccag aaagagaaag acgacgtatc agaaagaggt tatgtgattc    600
taccaaatga ctactttgaa atagttgaag taccagcata a                       641
```

<210> SEQ ID NO 55
<211> LENGTH: 642
<212> TYPE: DNA
<213> ORGANISM: Homo sapiens

<400> SEQUENCE: 55

```
atggtgcagt cctgctccgc ctacggctgc aagaaccgct acgacaagga caagcccgtt     60
tctttccaca gtttcctct tactcgaccc agtctttgta aagaatggga ggcagctgtc    120
agaagaaaaa actttaaacc caccaagtat agcagtattt attcagagca ctttactcca    180
gactgcttta agagagagtg caacaacaag ttactgaaag agaatgctgt gcccacaata    240
tttctttgta ctgagccaca tgacaagaaa gaagatcttc tggagccaca ggaacagctt    300
cccccacctc ctttaccgcc tcctgttccc caggttgatg ctgctattgg attactaatg    360
ccgcctcttc agacccctgt taatctctca gttttctgtg accacaacta tactgtggag    420
gatacaatgc accagcggaa aaggattcat cagctagaac agcaagttga aaaactcaga    480
aagaagctca agaccgcaca gcagcgatgc agaaggcaag aacggcagct tgaaaaatta    540
aaggaggttg ttcacttcca gaaagagaaa gacgacgtat cagaaagagg ttatgtgatt    600
ctaccaaatg actactttga aatagttgaa gtaccagcat aa                      642
```

<210> SEQ ID NO 56
<211> LENGTH: 642
<212> TYPE: DNA
<213> ORGANISM: Homo sapiens

<400> SEQUENCE: 56

```
gtggtgcagt cctgctccgc ctacggctgc aagaaccgct acgacaagga caagcccgtt     60
tctttccaca gtttcctct tactcgaccc agtctttgta aagaatggga ggcagctgtc    120
agaagaaaaa actttaaacc caccaagtat agcagtattt gttcagagca ctttactcca    180
gactgcttta agagagagtg caacaacaag ttactgaaag agaatgctgt gcccacaata    240
tttctttgta ctgagccaca tgacaagaaa gaagatcttc tggagccaca ggaacagctt    300
cccccacctc ctttaccgcc tcctgttccc caggttgatg ctgctattgg attactaatg    360
ccgcctcttc agacccctgt taatctctca gttttctgtg accacaacta tactgtggag    420
gatacaatgc accagcggaa aaggattcat cagctagaac agcaagttga aaaactcaga    480
aagaagctca agaccgcaca gcagcgatgc agaaggcaag aacggcagct tgaaaaatta    540
aaggaggttg ttcacttcca gaaagagaaa gacgacgtat cagaaagagg ttatgtgatt    600
ctaccaaatg actactttga aatagttgaa gtaccagcat aa                      642
```

<210> SEQ ID NO 57
<211> LENGTH: 642
<212> TYPE: DNA
<213> ORGANISM: Homo sapiens

<400> SEQUENCE: 57

```
atggtgcagt cctgctccgc ctacggctgc aagaaccgct acgacaagga caagcccgtt      60
actttccaca agtttcctct tactcgaccc agtctttgta aagaatggga ggcagctgtc     120
agaagaaaaa actttaaacc caccaagtat agcagtattt gttcagagca ctttactcca     180
gactgcttta agagagagtg caacaacaag ttactgaaag agaatgctgt gcccacaata     240
tttcttgta ctgagccaca tgacaagaaa gaagatcttc tggagccaca ggaacagctt     300
cccccacctc ctttaccgcc tcctgttttcc caggttgatg ctgctattgg attactaatg   360
ccgcctcttc agacccctgt taatctctca gttttctgtg accacaacta tactgtggag     420
gatacaatgc accagcggaa aaggattcat cagctagaac agcaagttga aaaactcaga     480
aagaagctca agaccgcaca gcagcgatgc agaaggcaag aacggcagct tgaaaaatta     540
aaggaggttg ttcacttcca gaaagagaaa gacgacgtat cagaaagagg ttatgtgatt     600
ctaccaaatg actactttga aatagttgaa gtaccagcat aa                        642
```

<210> SEQ ID NO 58
<211> LENGTH: 642
<212> TYPE: DNA
<213> ORGANISM: Homo sapiens

<400> SEQUENCE: 58

```
atggtgcagt cctgctccgc ctacggctgc aagaaccgct acgacaagga caagcccgtt      60
tctttctaca gtttcctct tactcgaccc agtctttgta aagaatggga ggcagctgtc     120
agaagaaaaa actttaaacc caccaagtat agcagtattt gttcagagca ctttactcca     180
gactgcttta agagagagtg caacaacaag ttactgaaag agaatgctgt gcccacaata     240
tttcttgta ctgagccaca tgacaagaaa gaagatcttc tggagccaca ggaacagctt     300
cccccacctc ctttaccgcc tcctgttttcc caggttgatg ctgctattgg attactaatg   360
ccgcctcttc agacccctgt taatctctca gttttctgtg accacaacta tactgtggag     420
gatacaatgc accagcggaa aaggattcat cagctagaac agcaagttga aaaactcaga     480
aagaagctca agaccgcaca gcagcgatgc agaaggcaag aacggcagct tgaaaaatta     540
aaggaggttg ttcacttcca gaaagagaaa gacgacgtat cagaaagagg ttatgtgatt     600
ctaccaaatg actactttga aatagttgaa gtaccagcat aa                        642
```

<210> SEQ ID NO 59
<211> LENGTH: 642
<212> TYPE: DNA
<213> ORGANISM: Homo sapiens

<400> SEQUENCE: 59

```
atggtgcagt cctgctccgc ctacggctgc aagaaacgct acgacaagga caagcccgtt      60
tctttccaca gtttcctct tactcgaccc agtctttgta aagaatggga ggcagctgtc     120
agaagaaaaa actttaaacc caccaagtat agcagtattt gttcagagca ctttactcca     180
gactgcttta agagagagtg caacaacaag ttactgaaag agaatgctgt gcccacaata     240
tttcttgta ctgagccaca tgacaagaaa gaagatcttc tggagccaca ggaacagctt     300
cccccacctc ctttaccgcc tcctgttttcc caggttgatg ctgctattgg attactaatg   360
ccgcctcttc agacccctgt taatctctca gttttctgtg accacaacta tactgtggag     420
gatacaatgc accagcggaa aaggattcat cagctagaac agcaagttga aaaactcaga     480
aagaagctca agaccgcaca gcagcgatgc agaaggcaag aacggcagct tgaaaaatta     540
```

| | |
|---|---|
| aaggaggttg ttcacttcca gaaagagaaa gacgacgtat cagaaagagg ttatgtgatt | 600 |
| ctaccaaatg actactttga aatagttgaa gtaccagcat aa | 642 |

<210> SEQ ID NO 60
<211> LENGTH: 641
<212> TYPE: DNA
<213> ORGANISM: Homo sapiens

<400> SEQUENCE: 60

| | |
|---|---|
| aggtgcagtc ctgctccgcc tacggctgca agaaccgcta cgacaaggac aagcccgttt | 60 |
| ctttccacaa gtttcctctt actcgaccca gtctttgtaa agaatgggag gcagctgtca | 120 |
| gaagaaaaaa ctttaaaccc accaagtata gcagtatttg ttcagagcac tttactccag | 180 |
| actgctttaa gagagagtgc aacaacaagt tactgaaaga gaatgctgtg cccacaatat | 240 |
| ttctttgtac tgagccacat gacaagaaag aagatcttct ggagccacag gaacagcttc | 300 |
| ccccacctcc tttaccgcct cctgtttccc aggttgatgc tgctattgga ttactaatgc | 360 |
| cgcctcttca gacccctgtt aatctctcag tttttctgtga ccacaactat actgtggagg | 420 |
| atacaatgca ccagcggaaa aggattcatc agctagaaca gcaagttgaa aaactcagaa | 480 |
| agaagctcaa gaccgcacag cagcgatgca gaaggcaaga acggcagctt gaaaaattaa | 540 |
| aggaggttgt tcacttccag aaagagaaag acgacgtatc agaaagaggt tatgtgattc | 600 |
| taccaaatga ctactttgaa atagttgaag taccagcata a | 641 |

<210> SEQ ID NO 61
<211> LENGTH: 642
<212> TYPE: DNA
<213> ORGANISM: Homo sapiens

<400> SEQUENCE: 61

| | |
|---|---|
| atggtgcagt cctgctccgc ctacggctgc aagaaccgct acgacaagga caagcccgtt | 60 |
| tcttcccaca gtttcctct tactcgaccc agtctttgta agaatggga ggcagctgtc | 120 |
| agaagaaaaa actttaaacc caccaagtat agcagtattt gttcagagca ctttactcca | 180 |
| gactgctttta agagagagtg caacaacaag ttactgaaag agaatgctgt gcccacaata | 240 |
| tttctttgta ctgagccaca tgacaagaaa gaagatcttc tggagccaca ggaacagctt | 300 |
| cccccacctc ctttaccgcc tcctgttttcc caggttgatg ctgctattgg attactaatg | 360 |
| ccgcctcttc agacccctgt taatctctca gttttctgtg accacaacta tactgtggag | 420 |
| gatacaatgc accagcggaa aaggattcat cagctagaac agcaagttga aaaactcaga | 480 |
| aagaagctca agaccgcaca gcagcgatgc agaaggcaag aacggcagct tgaaaaatta | 540 |
| aaggaggttg ttcacttcca gaaagagaaa gacgacgtat cagaaagagg ttatgtgatt | 600 |
| ctaccaaatg actactttga aatagttgaa gtaccagcat aa | 642 |

<210> SEQ ID NO 62
<211> LENGTH: 642
<212> TYPE: DNA
<213> ORGANISM: Homo sapiens

<400> SEQUENCE: 62

| | |
|---|---|
| atggtgcagt cctgctccgc ctacggctgc aagaaccgct acgacaagga caagcccgtt | 60 |
| tcttcccaca gtttcctct tactcgaccc agtctttgta agaatggga ggcagctgtc | 120 |
| agaagaaaaa actttaaact caccaagtat agcagtattt gttcagagca ctttactcca | 180 |
| gactgctttta agagagagtg caacaacaag ttactgaaag agaatgctgt gcccacaata | 240 |

```
tttctttgta ctgagccaca tgacaagaaa gaagatcttc tggagccaca ggaacagctt        300 ccccacctc ctttaccgcc tcctgttttcc caggttgatg ctgctattgg attactaatg        360
ccgcctcttc agacccctgt taatctctca gttttctgtg accacaacta tactgtggag        420
gatacaatgc accagcggaa aaggattcat cagctagaac agcaagttga aaaactcaga        480
aagaagctca agaccgcaca gcagcgatgc agaaggcaag aacggcagct tgaaaaatta       540
aaggaggttg ttcacttcca gaaagagaaa gacgacgtat cagaaagagg ttatgtgatt       600
ctaccaaatg actactttga aatagttgaa gtaccagcat aa                         642
```

<210> SEQ ID NO 63
<211> LENGTH: 639
<212> TYPE: DNA
<213> ORGANISM: Homo sapiens

<400> SEQUENCE: 63

```
atggtgcagt cctgctccgc ctacggctgc aagaaccgct acgacaagga caagcccgtt        60
tctttccaca gtttcctct tactcgaccc agtctttgta aagaatggga ggcagctgtc       120
agaagaaaaa actttaaacc caccaagtat agcagtattt gttcagagca ctttactcca       180
gactgcttta agagagagtg caacaacaag ttactgaaag agaatgctgt gcccacaata       240
tttctttgta ctgagccaca tgacaagaaa gaagatcttc tggagccaca ggaacagctt       300 ccccacctc ctttaccgcc tcctgttttcc caggttgatg ctgctattgg attactaatg       360
ccgcctcttc agacccctgt taatctctca gtctgtgacc acaactatac tgtggaggat       420
acaatgcacc agcggaaaag gattcatcag ctagaacagc aagttgaaaa actcagaaag       480
aagctcaaga ccgcacagca gcgatgcaga aggcaagaac ggcagcttga aaaattaaag       540
gaggttgttc acttccagaa agagaaagac gacgtatcag aaagaggtta tgtgattcta       600
ccaaatgact actttgaaat agttgaagta ccagcataa                             639
```

<210> SEQ ID NO 64
<211> LENGTH: 642
<212> TYPE: DNA
<213> ORGANISM: Homo sapiens

<400> SEQUENCE: 64

```
atggtgcagt tctgctccgc ctacggctgc aagaaccgct acgacaagga caagcccgtt        60
tctttccaca gtttcctct tactcgaccc agtctttgta aagaatggga ggcagctgtc       120
agaagaaaaa actttaaacc caccaagtat agcagtattt gttcagagca ctttactcca       180
gactgcttta agagagagtg caacaacaag ttactgaaag agaatgctgt gcccacaata       240
tttctttgta ctgagccaca tgacaagaaa gaagatcttc tggagccaca ggaacagctt       300 ccccacctc ctttaccgcc tcctgttttcc caggttgatg ctgctattgg attactaatg       360
ccgcctcttc agacccctgt taatctctca gttttctgtg accacaacta tactgtggag       420
gatacaatgc accagcggaa aaggattcat cagctagaac agcaagttga aaaactcaga       480
aagaagctca agaccgcaca gcagcgatgc agaaggcaag aacggcagct tgaaaaatta       540
aaggaggttg ttcacttcca gaaagagaaa gacgacgtat cagaaagagg ttatgtgatt       600
ctaccaaatg actactttga aatagttgaa gtaccagcat aa                         642
```

<210> SEQ ID NO 65
<211> LENGTH: 642
<212> TYPE: DNA
<213> ORGANISM: Homo sapiens

```
<400> SEQUENCE: 65
atggtgcagt cctgctccgc ctacggctgc aagaaccgct acgacaagga caagcccgtt      60
tctttccaca agtttcctct tactcgaccc agtctttgta aagaatggga ggcagctgtc     120
agaagaaaaa actttaaacc caccaagtat agcagtattt gttcagagca ctttactcca     180
gactgcttta agagagagtg caacaacaag ttactgaaag agaatgctgt gcccacaata     240
tttctttgta ctgagccaca tgacaagaaa gaagatcttc tggagccaca ggaacagctt     300
cccccacctc ctttaccgcc tcctgttttc caggttgatg ctgctattgg attactaatg     360
ccgcctcttc agacccctgt taatctctca gttttctgtg accacaacta tactgtggag     420
gatacaatgc accagcggaa aaggattcat cagctagaac agcaagttga aaaactcaga     480
aagaagctca agaccgcaca gcagcgatgc agaaggcaag aacggcagct tgaaaaatta     540
aaggaggttg ttcacttcca gaaagagaaa gacgacgtac agaaagagg ttatgtgatt      600 ctaccaaatg actactttga aatagttgaa gtaccagcat aa                       642

<210> SEQ ID NO 66
<211> LENGTH: 642
<212> TYPE: DNA
<213> ORGANISM: Homo sapiens

<400> SEQUENCE: 66
atggtgcagt cctgctccgc ctacggctgc aagaaccgct acgacaagga caagcccgtt      60
tctttccaca agtttcctct tactcgaccc agtctttgta aagaatggga ggcagctgtc     120
agaagaaaaa actttaaacc caccaagtat agcagtattt gttcagagca ctttactcca     180
gactgcttta agagagagtg caacaacaag ttactgaaag agaatgctgt gcccacaata     240
tttctttgta ctgagccaca tgacaagaaa gaagatcttc tggagccaca ggaacagctt     300
cccccacctc ctttaccgcc tcctgttttc caggttgatg ctgctattgg attactaatg     360
ccgcctcttc agacccctgt taatctctca gttttctgtg accacaacta tactgtggag     420
gatgcaatgc accagcggaa aaggattcat cagctagaac agcaagttga aaaactcaga     480
aagaagctca agaccgcaca gcagcgatgc agaaggcaag aacggcagct tgaaaaatta     540
aaggaggttg ttcacttcca gaaagagaaa gacgacgtat cagaaagagg ttatgtgatt     600
ctaccaaatg actactttga aatagttgaa gtaccagcat aa                       642

<210> SEQ ID NO 67
<211> LENGTH: 640
<212> TYPE: DNA
<213> ORGANISM: Homo sapiens

<400> SEQUENCE: 67
atggtgcagt cctgctccgc ctacggctgc aagaaccgct acgacaagga caagcccgtt      60
tctttccaca agtttcctct tactcgaccc agtctttgta aagaatggga ggcagctgtc     120
agaagaaaaa actttaaacc caccaagtat agcagtattt gttcagagca ctttactcca     180
gactgcttta agagagagtg caacaacaag ttactgaaag agaatgctgt gcccacaata     240
tttctttgtt gagccacatg acaagaaaga agatcttctg gagccacagg aacagcttcc     300
cccacctcct ttaccgcctc ctgttttccca ggttgatgct gctattggat tactaatgcc     360
gcctcttcag acccctgtta atctctcagt tttctgtgac cacaactata ctgtggagga     420
tacaatgcac cagcggaaaa ggattcatca gctagaacag caagttgaaa actcagaaaa     480
gaagctcaag accgcacagc agcgatgcag aaggcaagaa cggcagcttg aaaaattaaa     540
```

```
ggaggttgtt cacttccaga aagagaaaga cgacgtatca gaaagaggtt atgtgattct    600
accaaatgac tactttgaaa tagttgaagt accagcataa                         640

<210> SEQ ID NO 68
<211> LENGTH: 642
<212> TYPE: DNA
<213> ORGANISM: Homo sapiens

<400> SEQUENCE: 68
atggtgcagt cctgctccgc ctacggctgc aagaaccgct acgacaagga caagcccgtt     60
tctttccaca gtttcctcct tactcgaccc agtctttgta agaatgggag ggcagctgtc    120
agaagaaaaa actttaaacc caccaagtat agcagtattt gttcagagca ctttactcca    180
gactgcttta agagagagtg caacaacaag ttactgaaag agaatgctgt gcccacaata    240
tttctttgta ctgagccaca tgacaagaaa gaagatcttc tggagccaca ggaacagctt    300
cccccacctc ctttaccgcc tcctgtttcc caggttgatg ctgctattgg attactaatg    360
ccgcctcttc agaccctgt taatctctca gttttctgtg accacaacta tactgtggag    420
gatacaatgc accagcggaa aaggattcat cagctagaac agcaagttga aaaactcaga    480
aagaagctca gaccgcaca gcagtgatgc agaaggcaag aacggcagct tgaaaaatta    540
aaggaggttg ttcacttcca gaagagaaa gacgacgtat cagaaagagg ttatgtgatt    600
ctaccaaatg actactttga aatagttgaa gtaccagcat aa                      642

<210> SEQ ID NO 69
<211> LENGTH: 28
<212> TYPE: PRT
<213> ORGANISM: Homo sapiens

<400> SEQUENCE: 69

Met Val Gln Ser Cys Ser Ala Tyr Gly Cys Lys Asn Arg Tyr Asp Lys
1               5                   10                  15

Asp Lys Pro Val Ser Phe His Lys Phe Pro Leu Thr
            20                  25

<210> SEQ ID NO 70
<211> LENGTH: 213
<212> TYPE: PRT
<213> ORGANISM: Homo sapiens

<400> SEQUENCE: 70

Met Val Gln Ser Cys Ser Ala Tyr Gly Cys Lys Asn Arg Tyr Asp Lys
1               5                   10                  15

Asp Lys Pro Val Ser Phe His Lys Phe Pro Leu Thr Pro Ser Leu
            20                  25                  30

Cys Lys Glu Trp Glu Ala Ala Val Arg Arg Lys Asn Phe Lys Pro Thr
        35                  40                  45

Lys Tyr Ser Ser Ile Cys Ser Glu His Phe Thr Pro Asp Cys Phe Lys
    50                  55                  60

Arg Glu Cys Asn Asn Lys Leu Leu Lys Glu Asn Ala Val Pro Thr Ile
65                  70                  75                  80

Phe Leu Cys Thr Glu Pro His Asp Lys Lys Glu Asp Leu Leu Glu Pro
                85                  90                  95

Gln Glu Gln Leu Pro Pro Pro Pro Leu Pro Pro Pro Val Ser Gln Val
            100                 105                 110

Asp Ala Ala Ile Gly Leu Leu Met Pro Pro Leu Gln Thr Pro Val Asn
        115                 120                 125
```

```
Leu Ser Val Phe Cys Asp His Asn Tyr Thr Val Glu Asp Thr Met His
    130                 135                 140

Gln Arg Lys Arg Ile His Gln Leu Glu Gln Gln Val Glu Lys Leu Arg
145                 150                 155                 160

Lys Lys Leu Lys Thr Ala Gln Gln Arg Cys Arg Arg Gln Glu Arg Gln
                165                 170                 175

Leu Glu Lys Leu Lys Glu Val Val His Phe Gln Lys Glu Lys Asp Asp
                180                 185                 190

Val Ser Glu Arg Gly Tyr Val Ile Leu Pro Asn Asp Tyr Phe Glu Ile
            195                 200                 205

Val Glu Val Pro Ala
            210

<210> SEQ ID NO 71
<211> LENGTH: 213
<212> TYPE: PRT
<213> ORGANISM: Homo sapiens

<400> SEQUENCE: 71

Met Val Gln Ser Cys Ser Ala Tyr Gly Cys Lys Asn Arg Tyr Asp Lys
1               5                   10                  15

Asp Lys Pro Val Ser Phe His Lys Phe Pro Leu Thr Arg Pro Ser Leu
                20                  25                  30

Cys Lys Glu Trp Glu Ala Ala Val Arg Arg Lys Asn Phe Lys Pro Thr
            35                  40                  45

Lys Tyr Ser Ser Ile Cys Ser Glu His Phe Thr Pro Asp Cys Phe Lys
        50                  55                  60

Arg Glu Cys Asn Asn Lys Leu Leu Lys Glu Asn Ala Val Pro Thr Ile
65                  70                  75                  80

Phe Leu Cys Thr Glu Pro His Asp Arg Lys Glu Asp Leu Leu Glu Pro
                85                  90                  95

Gln Glu Gln Leu Pro Pro Pro Leu Pro Pro Val Ser Gln Val
                100                 105                 110

Asp Ala Ala Ile Gly Leu Leu Met Pro Pro Leu Gln Thr Pro Val Asn
            115                 120                 125

Leu Ser Val Phe Cys Asp His Asn Tyr Thr Val Glu Asp Thr Met His
    130                 135                 140

Gln Arg Lys Arg Ile His Gln Leu Glu Gln Gln Val Glu Lys Leu Arg
145                 150                 155                 160

Lys Lys Leu Lys Thr Ala Gln Gln Arg Cys Arg Arg Gln Glu Arg Gln
                165                 170                 175

Leu Glu Lys Leu Lys Glu Val Val His Phe Gln Lys Glu Lys Asp Asp
                180                 185                 190

Val Ser Glu Arg Gly Tyr Val Ile Leu Pro Asn Asp Tyr Phe Glu Ile
            195                 200                 205

Val Glu Val Pro Ala
            210

<210> SEQ ID NO 72
<211> LENGTH: 213
<212> TYPE: PRT
<213> ORGANISM: Homo sapiens

<400> SEQUENCE: 72

Met Val Gln Ser Cys Ser Ala Tyr Gly Cys Lys Asn Arg Tyr Asp Lys
1               5                   10                  15

Asp Lys Pro Val Ser Phe His Lys Phe Pro Leu Thr Arg Pro Ser Leu
```

```
                        20                  25                  30
Cys Lys Glu Trp Glu Ala Thr Val Arg Arg Lys Asn Phe Lys Pro Thr
             35                  40                  45

Lys Tyr Ser Ser Ile Cys Ser Glu His Phe Thr Pro Asp Cys Phe Lys
 50                  55                  60

Arg Glu Cys Asn Asn Lys Leu Leu Lys Glu Asn Ala Val Pro Thr Ile
 65                  70                  75                  80

Phe Leu Cys Thr Glu Pro His Asp Lys Lys Glu Asp Leu Leu Glu Pro
                 85                  90                  95

Gln Glu Gln Leu Pro Pro Pro Leu Pro Pro Val Ser Gln Val
                100                 105                 110

Asp Ala Ala Ile Gly Leu Leu Met Pro Pro Leu Gln Thr Pro Val Asn
                115                 120                 125

Leu Ser Val Phe Cys Asp His Asn Tyr Thr Val Glu Asp Thr Met His
                130                 135                 140

Gln Arg Lys Arg Ile His Gln Leu Glu Gln Gln Val Glu Lys Leu Arg
145                 150                 155                 160

Lys Lys Leu Lys Thr Ala Gln Gln Arg Cys Arg Arg Gln Glu Arg Gln
                165                 170                 175

Leu Glu Lys Leu Lys Glu Val Val His Phe Gln Lys Glu Lys Asp Asp
                180                 185                 190

Val Ser Glu Arg Gly Tyr Val Ile Leu Pro Asn Asp Tyr Phe Glu Ile
                195                 200                 205

Val Glu Val Pro Ala
                210

<210> SEQ ID NO 73
<211> LENGTH: 179
<212> TYPE: PRT
<213> ORGANISM: Homo sapiens

<400> SEQUENCE: 73

Met Val Gln Ser Cys Ser Ala Tyr Gly Cys Lys Asn Arg Tyr Asp Lys
 1                   5                  10                  15

Asp Lys Pro Val Ser Phe His Lys Phe Pro Leu Thr Arg Pro Ser Leu
                 20                  25                  30

Cys Lys Glu Trp Glu Ala Ala Val Arg Arg Lys Asn Phe Lys Pro Thr
             35                  40                  45

Lys Tyr Ser Ser Ile Cys Ser Glu His Phe Thr Pro Asp Cys Phe Lys
 50                  55                  60

Arg Glu Cys Asn Asn Lys Leu Leu Lys Glu Asn Ala Val Pro Thr Ile
 65                  70                  75                  80

Phe Leu Cys Thr Glu Pro His Asp Lys Lys Glu Asp Leu Leu Glu Pro
                 85                  90                  95

Gln Glu Gln Leu Pro Pro Pro Leu Pro Pro Val Ser Gln Val
                100                 105                 110

Asp Ala Ala Ile Gly Leu Leu Met Pro Pro Leu Gln Thr Pro Val Asn
                115                 120                 125

Leu Ser Val Phe Cys Asp His Asn Tyr Thr Val Glu Asp Thr Met His
                130                 135                 140

Gln Arg Lys Arg Ile His Gln Leu Glu Ser Lys Leu Lys Asn Ser Glu
145                 150                 155                 160

Arg Ser Ser Arg Pro His Ser Ser Asp Ala Glu Gly Lys Asn Gly Ser
                165                 170                 175

Leu Lys Asn
```

```
<210> SEQ ID NO 74
<211> LENGTH: 213
<212> TYPE: PRT
<213> ORGANISM: Homo sapiens

<400> SEQUENCE: 74

Met Val Gln Ser Cys Ser Ala Tyr Gly Cys Lys Asn Arg Tyr Asp Lys
1               5                   10                  15

Asp Lys Pro Val Ser Phe His Lys Phe Pro Leu Thr Arg Pro Ser Leu
            20                  25                  30

Cys Lys Glu Trp Glu Ala Ala Val Arg Arg Lys Asn Phe Lys Pro Thr
        35                  40                  45

Lys Tyr Ser Ser Ile Tyr Ser Glu His Phe Thr Pro Asp Cys Phe Lys
    50                  55                  60

Arg Glu Cys Asn Asn Lys Leu Leu Lys Glu Asn Ala Val Pro Thr Ile
65                  70                  75                  80

Phe Leu Cys Thr Glu Pro His Asp Lys Lys Glu Asp Leu Leu Glu Pro
                85                  90                  95

Gln Glu Gln Leu Pro Pro Pro Leu Pro Pro Val Ser Gln Val
                100                 105                 110

Asp Ala Ala Ile Gly Leu Leu Met Pro Pro Leu Gln Thr Pro Val Asn
            115                 120                 125

Leu Ser Val Phe Cys Asp His Asn Tyr Thr Val Glu Asp Thr Met His
    130                 135                 140

Gln Arg Lys Arg Ile His Gln Leu Glu Gln Val Glu Lys Leu Arg
145                 150                 155                 160

Lys Lys Leu Lys Thr Ala Gln Gln Arg Cys Arg Arg Gln Glu Arg Gln
                165                 170                 175

Leu Glu Lys Leu Lys Glu Val Val His Phe Gln Lys Gly Lys Asp Asp
            180                 185                 190

Val Ser Glu Arg Gly Tyr Val Ile Leu Pro Asn Asp Tyr Phe Glu Ile
        195                 200                 205

Val Glu Val Pro Ala
    210

<210> SEQ ID NO 75
<211> LENGTH: 213
<212> TYPE: PRT
<213> ORGANISM: Homo sapiens

<400> SEQUENCE: 75

Met Val Gln Ser Cys Ser Ala Tyr Gly Cys Lys Asn Arg Tyr Asp Lys
1               5                   10                  15

Asp Lys Pro Val Thr Phe His Lys Phe Pro Leu Thr Arg Pro Ser Leu
            20                  25                  30

Cys Lys Glu Trp Glu Ala Ala Val Arg Arg Lys Asn Phe Lys Pro Thr
        35                  40                  45

Lys Tyr Ser Ser Ile Cys Ser Glu His Phe Thr Pro Asp Cys Phe Lys
    50                  55                  60

Arg Glu Cys Asn Asn Lys Leu Leu Lys Glu Asn Ala Val Pro Thr Ile
65                  70                  75                  80

Phe Leu Cys Thr Glu Pro His Asp Lys Lys Glu Asp Leu Leu Glu Pro
                85                  90                  95

Gln Glu Gln Leu Pro Pro Pro Leu Pro Pro Val Ser Gln Val
                100                 105                 110
```

```
Asp Ala Ala Ile Gly Leu Leu Met Pro Pro Leu Gln Thr Pro Val Asn
        115                 120                 125

Leu Ser Val Phe Cys Asp His Asn Tyr Thr Val Glu Asp Thr Met His
    130                 135                 140

Gln Arg Lys Arg Ile His Gln Leu Glu Gln Gln Val Glu Lys Leu Arg
145                 150                 155                 160

Lys Lys Leu Lys Thr Ala Gln Gln Arg Cys Arg Arg Gln Glu Arg Gln
                165                 170                 175

Leu Glu Lys Leu Lys Glu Val Val His Phe Gln Lys Glu Lys Asp Asp
                180                 185                 190

Val Ser Glu Arg Gly Tyr Val Ile Leu Pro Asn Asp Tyr Phe Glu Ile
                195                 200                 205

Val Glu Val Pro Ala
    210

<210> SEQ ID NO 76
<211> LENGTH: 213
<212> TYPE: PRT
<213> ORGANISM: Homo sapiens

<400> SEQUENCE: 76

Met Val Gln Ser Cys Ser Ala Tyr Gly Cys Lys Asn Arg Tyr Asp Lys
1               5                   10                  15

Asp Lys Pro Val Ser Phe Tyr Lys Phe Pro Leu Thr Arg Pro Ser Leu
                20                  25                  30

Cys Lys Glu Trp Glu Ala Ala Val Arg Arg Lys Asn Phe Lys Pro Thr
            35                  40                  45

Lys Tyr Ser Ser Ile Cys Ser Glu His Phe Thr Pro Asp Cys Phe Lys
    50                  55                  60

Arg Glu Cys Asn Asn Lys Leu Leu Lys Glu Asn Ala Val Pro Thr Ile
65                  70                  75                  80

Phe Leu Cys Thr Glu Pro His Asp Lys Lys Asp Leu Leu Glu Pro
                85                  90                  95

Gln Glu Gln Leu Pro Pro Pro Leu Pro Pro Val Ser Gln Val
                100                 105                 110

Asp Ala Ala Ile Gly Leu Leu Met Pro Pro Leu Gln Thr Pro Val Asn
        115                 120                 125

Leu Ser Val Phe Cys Asp His Asn Tyr Thr Val Glu Asp Thr Met His
    130                 135                 140

Gln Arg Lys Arg Ile His Gln Leu Glu Gln Gln Val Glu Lys Leu Arg
145                 150                 155                 160

Lys Lys Leu Lys Thr Ala Gln Gln Arg Cys Arg Arg Gln Glu Arg Gln
                165                 170                 175

Leu Glu Lys Leu Lys Glu Val Val His Phe Gln Lys Glu Lys Asp Asp
                180                 185                 190

Val Ser Glu Arg Gly Tyr Val Ile Leu Pro Asn Asp Tyr Phe Glu Ile
                195                 200                 205

Val Glu Val Pro Ala
    210

<210> SEQ ID NO 77
<211> LENGTH: 213
<212> TYPE: PRT
<213> ORGANISM: Homo sapiens

<400> SEQUENCE: 77

Met Val Gln Ser Cys Ser Ala Tyr Gly Cys Lys Lys Arg Tyr Asp Lys
```

```
                  1               5              10              15
Asp Lys Pro Val Ser Phe His Lys Phe Pro Leu Thr Arg Pro Ser Leu
                 20              25              30

Cys Lys Glu Trp Glu Ala Ala Val Arg Arg Lys Asn Phe Lys Pro Thr
                 35              40              45

Lys Tyr Ser Ser Ile Cys Ser Glu His Phe Thr Pro Asp Cys Phe Lys
                 50              55              60

Arg Glu Cys Asn Asn Lys Leu Leu Lys Glu Asn Ala Val Pro Thr Ile
 65              70              75              80

Phe Leu Cys Thr Glu Pro His Asp Lys Lys Glu Asp Leu Leu Glu Pro
                 85              90              95

Gln Glu Gln Leu Pro Pro Pro Leu Pro Pro Val Ser Gln Val
                100             105             110

Asp Ala Ala Ile Gly Leu Leu Met Pro Pro Leu Gln Thr Pro Val Asn
                115             120             125

Leu Ser Val Phe Cys Asp His Asn Tyr Thr Val Glu Asp Thr Met His
                130             135             140

Gln Arg Lys Arg Ile His Gln Leu Glu Gln Gln Val Glu Lys Leu Arg
145             150             155             160

Lys Lys Leu Lys Thr Ala Gln Gln Arg Cys Arg Arg Gln Glu Arg Gln
                165             170             175

Leu Glu Lys Leu Lys Glu Val Val His Phe Gln Lys Glu Lys Asp Asp
                180             185             190

Val Ser Glu Arg Gly Tyr Val Ile Leu Pro Asn Asp Tyr Phe Glu Ile
                195             200             205

Val Glu Val Pro Ala
                210

<210> SEQ ID NO 78
<211> LENGTH: 213
<212> TYPE: PRT
<213> ORGANISM: Homo sapiens

<400> SEQUENCE: 78

Met Val Gln Ser Cys Ser Ala Tyr Gly Cys Lys Asn Arg Tyr Asp Lys
1               5              10              15

Asp Lys Pro Val Ser Ser His Lys Phe Pro Leu Thr Arg Pro Ser Leu
                 20              25              30

Cys Lys Glu Trp Glu Ala Ala Val Arg Arg Lys Asn Phe Lys Pro Thr
                 35              40              45

Lys Tyr Ser Ser Ile Cys Ser Glu His Phe Thr Pro Asp Cys Phe Lys
                 50              55              60

Arg Glu Cys Asn Asn Lys Leu Leu Lys Glu Asn Ala Val Pro Thr Ile
 65              70              75              80

Phe Leu Cys Thr Glu Pro His Asp Lys Lys Glu Asp Leu Leu Glu Pro
                 85              90              95

Gln Glu Gln Leu Pro Pro Pro Leu Pro Pro Val Ser Gln Val
                100             105             110

Asp Ala Ala Ile Gly Leu Leu Met Pro Pro Leu Gln Thr Pro Val Asn
                115             120             125

Leu Ser Val Phe Cys Asp His Asn Tyr Thr Val Glu Asp Thr Met His
                130             135             140

Gln Arg Lys Arg Ile His Gln Leu Glu Gln Gln Val Glu Lys Leu Arg
145             150             155             160

Lys Lys Leu Lys Thr Ala Gln Gln Arg Cys Arg Arg Gln Glu Arg Gln
```

-continued

```
                165                 170                 175
Leu Glu Lys Leu Lys Glu Val Val His Phe Gln Lys Glu Lys Asp Asp
            180                 185                 190
Val Ser Glu Arg Gly Tyr Val Ile Leu Pro Asn Asp Tyr Phe Glu Ile
            195                 200                 205
Val Glu Val Pro Ala
            210

<210> SEQ ID NO 79
<211> LENGTH: 213
<212> TYPE: PRT
<213> ORGANISM: Homo sapiens

<400> SEQUENCE: 79

Met Val Gln Ser Cys Ser Ala Tyr Gly Cys Lys Asn Arg Tyr Asp Lys
1               5                   10                  15
Asp Lys Pro Val Ser Phe His Lys Phe Pro Leu Thr Arg Pro Ser Leu
            20                  25                  30
Cys Lys Glu Trp Glu Ala Ala Val Arg Arg Lys Asn Phe Lys Leu Thr
        35                  40                  45
Lys Tyr Ser Ser Ile Cys Ser Glu His Phe Thr Pro Asp Cys Phe Lys
    50                  55                  60
Arg Glu Cys Asn Asn Lys Leu Leu Lys Glu Asn Ala Val Pro Thr Ile
65                  70                  75                  80
Phe Leu Cys Thr Glu Pro His Asp Lys Lys Glu Asp Leu Leu Glu Pro
                85                  90                  95
Gln Glu Gln Leu Pro Pro Pro Leu Pro Pro Val Ser Gln Val
            100                 105                 110
Asp Ala Ala Ile Gly Leu Leu Met Pro Pro Leu Gln Thr Pro Val Asn
            115                 120                 125
Leu Ser Val Phe Cys Asp His Asn Tyr Thr Val Glu Asp Thr Met His
        130                 135                 140
Gln Arg Lys Arg Ile His Gln Leu Glu Gln Gln Val Glu Lys Leu Arg
145                 150                 155                 160
Lys Lys Leu Lys Thr Ala Gln Gln Arg Cys Arg Arg Gln Glu Arg Gln
                165                 170                 175
Leu Glu Lys Leu Lys Glu Val Val His Phe Gln Lys Glu Lys Asp Asp
            180                 185                 190
Val Ser Glu Arg Gly Tyr Val Ile Leu Pro Asn Asp Tyr Phe Glu Ile
            195                 200                 205
Val Glu Val Pro Ala
            210

<210> SEQ ID NO 80
<211> LENGTH: 212
<212> TYPE: PRT
<213> ORGANISM: Homo sapiens

<400> SEQUENCE: 80

Met Val Gln Ser Cys Ser Ala Tyr Gly Cys Lys Asn Arg Tyr Asp Lys
1               5                   10                  15
Asp Lys Pro Val Ser Phe His Lys Phe Pro Leu Thr Arg Pro Ser Leu
            20                  25                  30
Cys Lys Glu Trp Glu Ala Ala Val Arg Arg Lys Asn Phe Lys Pro Thr
        35                  40                  45
Lys Tyr Ser Ser Ile Cys Ser Glu His Phe Thr Pro Asp Cys Phe Lys
    50                  55                  60
```

```
Arg Glu Cys Asn Asn Lys Leu Leu Lys Glu Asn Ala Val Pro Thr Ile
 65                  70                  75                  80

Phe Leu Cys Thr Glu Pro His Asp Lys Lys Glu Asp Leu Leu Glu Pro
                 85                  90                  95

Gln Glu Gln Leu Pro Pro Pro Leu Pro Pro Val Ser Gln Val
            100                 105                 110

Asp Ala Ala Ile Gly Leu Leu Met Pro Pro Leu Gln Thr Pro Val Asn
            115                 120                 125

Leu Ser Val Cys Asp His Asn Tyr Thr Val Glu Asp Thr Met His Gln
        130                 135                 140

Arg Lys Arg Ile His Gln Leu Glu Gln Gln Val Glu Lys Leu Arg Lys
145                 150                 155                 160

Lys Leu Lys Thr Ala Gln Gln Arg Cys Arg Arg Gln Glu Arg Gln Leu
                165                 170                 175

Glu Lys Leu Lys Glu Val Val His Phe Gln Lys Glu Lys Asp Asp Val
            180                 185                 190

Ser Glu Arg Gly Tyr Val Ile Leu Pro Asn Asp Tyr Phe Glu Ile Val
            195                 200                 205

Glu Val Pro Ala
        210

<210> SEQ ID NO 81
<211> LENGTH: 213
<212> TYPE: PRT
<213> ORGANISM: Homo sapiens

<400> SEQUENCE: 81

Met Val Gln Phe Cys Ser Ala Tyr Gly Cys Lys Asn Arg Tyr Asp Lys
  1               5                  10                  15

Asp Lys Pro Val Ser Phe His Lys Phe Pro Leu Thr Arg Pro Ser Leu
                 20                  25                  30

Cys Lys Glu Trp Glu Ala Ala Val Arg Arg Lys Asn Phe Lys Pro Thr
             35                  40                  45

Lys Tyr Ser Ser Ile Cys Ser Glu His Phe Thr Pro Asp Cys Phe Lys
 50                  55                  60

Arg Glu Cys Asn Asn Lys Leu Leu Lys Glu Asn Ala Val Pro Thr Ile
 65                  70                  75                  80

Phe Leu Cys Thr Glu Pro His Asp Lys Lys Glu Asp Leu Leu Glu Pro
                 85                  90                  95

Gln Glu Gln Leu Pro Pro Pro Leu Pro Pro Val Ser Gln Val
            100                 105                 110

Asp Ala Ala Ile Gly Leu Leu Met Pro Pro Leu Gln Thr Pro Val Asn
            115                 120                 125

Leu Ser Val Phe Cys Asp His Asn Tyr Thr Val Glu Asp Thr Met His
        130                 135                 140

Gln Arg Lys Arg Ile His Gln Leu Glu Gln Gln Val Glu Lys Leu Arg
145                 150                 155                 160

Lys Lys Leu Lys Thr Ala Gln Gln Arg Cys Arg Arg Gln Glu Arg Gln
                165                 170                 175

Leu Glu Lys Leu Lys Glu Val Val His Phe Gln Lys Glu Lys Asp Asp
            180                 185                 190

Val Ser Glu Arg Gly Tyr Val Ile Leu Pro Asn Asp Tyr Phe Glu Ile
            195                 200                 205

Val Glu Val Pro Ala
        210
```

<210> SEQ ID NO 82
<211> LENGTH: 213
<212> TYPE: PRT
<213> ORGANISM: Homo sapiens

<400> SEQUENCE: 82

Met Val Gln Ser Cys Ser Ala Tyr Gly Cys Lys Asn Arg Tyr Asp Lys
1               5                   10                  15

Asp Lys Pro Val Ser Phe His Lys Phe Pro Leu Thr Arg Pro Ser Leu
            20                  25                  30

Cys Lys Glu Trp Glu Ala Ala Val Arg Arg Lys Asn Phe Lys Pro Thr
        35                  40                  45

Lys Tyr Ser Ser Ile Cys Ser Glu His Phe Thr Pro Asp Cys Phe Lys
    50                  55                  60

Arg Glu Cys Asn Asn Lys Leu Leu Lys Glu Asn Ala Val Pro Thr Ile
65                  70                  75                  80

Phe Leu Cys Thr Glu Pro His Asp Lys Lys Glu Asp Leu Leu Glu Pro
                85                  90                  95

Gln Glu Gln Leu Pro Pro Pro Leu Pro Pro Val Ser Gln Val
            100                 105                 110

Asp Ala Ala Ile Gly Leu Leu Met Pro Pro Leu Gln Thr Pro Val Asn
        115                 120                 125

Leu Ser Val Phe Cys Asp His Asn Tyr Thr Val Asp Thr Met His
    130                 135                 140

Gln Arg Lys Arg Ile His Gln Leu Glu Gln Val Glu Lys Leu Arg
145                 150                 155                 160

Lys Lys Leu Lys Thr Ala Gln Gln Arg Cys Arg Arg Gln Glu Arg Gln
                165                 170                 175

Leu Glu Lys Leu Lys Glu Val Val His Phe Gln Lys Gly Lys Asp Asp
            180                 185                 190

Val Pro Glu Arg Gly Tyr Val Ile Leu Pro Asn Asp Tyr Phe Glu Ile
        195                 200                 205

Val Glu Val Pro Ala
    210

<210> SEQ ID NO 83
<211> LENGTH: 213
<212> TYPE: PRT
<213> ORGANISM: Homo sapiens

<400> SEQUENCE: 83

Met Val Gln Ser Cys Ser Ala Tyr Gly Cys Lys Asn Arg Tyr Asp Lys
1               5                   10                  15

Asp Lys Pro Val Ser Phe His Lys Phe Pro Leu Thr Arg Pro Ser Leu
            20                  25                  30

Cys Lys Glu Trp Glu Ala Ala Val Arg Arg Lys Asn Phe Lys Pro Thr
        35                  40                  45

Lys Tyr Ser Ser Ile Cys Ser Glu His Phe Thr Pro Asp Cys Phe Lys
    50                  55                  60

Arg Glu Cys Asn Asn Lys Leu Leu Lys Glu Asn Ala Val Pro Thr Ile
65                  70                  75                  80

Phe Leu Cys Thr Glu Pro His Asp Lys Lys Glu Asp Leu Leu Glu Pro
                85                  90                  95

Gln Glu Gln Leu Pro Pro Pro Leu Pro Pro Val Ser Gln Val
            100                 105                 110

```
Asp Ala Ala Ile Gly Leu Leu Met Pro Pro Leu Gln Thr Pro Val Asn
            115                 120                 125

Leu Ser Val Phe Cys Asp His Asn Tyr Thr Val Glu Asp Ala Met His
    130                 135                 140

Gln Arg Lys Arg Ile His Gln Leu Glu Gln Gln Val Glu Lys Leu Arg
145                 150                 155                 160

Lys Lys Leu Lys Thr Ala Gln Gln Arg Cys Arg Arg Gln Glu Arg Gln
                165                 170                 175

Leu Glu Lys Leu Lys Glu Val Val His Phe Gln Lys Glu Lys Asp Asp
            180                 185                 190

Val Ser Glu Arg Gly Tyr Val Ile Leu Pro Asn Asp Tyr Phe Glu Ile
            195                 200                 205

Val Glu Val Pro Ala
            210

<210> SEQ ID NO 84
<211> LENGTH: 83
<212> TYPE: PRT
<213> ORGANISM: Homo sapiens

<400> SEQUENCE: 84

Met Val Gln Ser Cys Ser Ala Tyr Gly Cys Lys Asn Arg Tyr Asp Lys
1               5                   10                  15

Asp Lys Pro Val Ser Phe His Lys Phe Pro Leu Thr Arg Pro Ser Leu
                20                  25                  30

Cys Lys Glu Trp Glu Ala Ala Val Arg Arg Lys Asn Phe Lys Pro Thr
            35                  40                  45

Lys Tyr Ser Ser Ile Cys Ser Glu His Phe Thr Pro Asp Cys Phe Lys
    50                  55                  60

Arg Glu Cys Asn Asn Lys Leu Leu Lys Glu Asn Ala Val Pro Thr Ile
65                  70                  75                  80

Phe Leu Cys

<210> SEQ ID NO 85
<211> LENGTH: 168
<212> TYPE: PRT
<213> ORGANISM: Homo sapiens

<400> SEQUENCE: 85

Met Val Gln Ser Cys Ser Ala Tyr Gly Cys Lys Asn Arg Tyr Asp Lys
1               5                   10                  15

Asp Lys Pro Val Ser Phe His Lys Phe Pro Leu Thr Arg Pro Ser Leu
                20                  25                  30

Cys Lys Glu Trp Glu Ala Ala Val Arg Arg Lys Asn Phe Lys Pro Thr
            35                  40                  45

Lys Tyr Ser Ser Ile Cys Ser Glu His Phe Thr Pro Asp Cys Phe Lys
    50                  55                  60

Arg Glu Cys Asn Asn Lys Leu Leu Lys Glu Asn Ala Val Pro Thr Ile
65                  70                  75                  80

Phe Leu Cys Thr Glu Pro His Asp Lys Lys Glu Asp Leu Leu Glu Pro
                85                  90                  95

Gln Glu Gln Leu Pro Pro Pro Leu Pro Pro Val Ser Gln Val
                100                 105                 110

Asp Ala Ala Ile Gly Leu Leu Met Pro Pro Leu Gln Thr Pro Val Asn
            115                 120                 125

Leu Ser Val Phe Cys Asp His Asn Tyr Thr Val Glu Asp Thr Met His
    130                 135                 140
```

-continued

Gln Arg Lys Arg Ile His Gln Leu Glu Gln Gln Val Glu Lys Leu Arg
145                 150                 155                 160

Lys Lys Leu Lys Thr Ala Gln Gln
                165

<210> SEQ ID NO 86
<211> LENGTH: 6
<212> TYPE: PRT
<213> ORGANISM: Unknown
<220> FEATURE:
<223> OTHER INFORMATION: Description of Unknown: Motif sequence

<400> SEQUENCE: 86

Ala Val Pro Thr Ile Phe
1               5

<210> SEQ ID NO 87
<211> LENGTH: 63
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(5)
<223> OTHER INFORMATION: Any amino acid; this region may encompass 2-4
      residues
<220> FEATURE:
<221> NAME/KEY: MOD_RES
<222> LOCATION: (7)..(59)
<223> OTHER INFORMATION: Any amino acid; this region may encompass 35-53
      residues
<220> FEATURE:
<221> NAME/KEY: MOD_RES
<222> LOCATION: (61)..(62)
<223> OTHER INFORMATION: Any amino acid

<400> SEQUENCE: 87

Cys Xaa Xaa Xaa Xaa Cys Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Cys Xaa Xaa His
    50                  55                  60

<210> SEQ ID NO 88
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 88

His His His His His His
1               5

<210> SEQ ID NO 89
<211> LENGTH: 31
<212> TYPE: DNA
<213> ORGANISM: Homo sapiens

<400> SEQUENCE: 89
agaagaaaaa acttgggttt accaccaagt a                              31

<210> SEQ ID NO 90
<211> LENGTH: 29
<212> TYPE: DNA
<213> ORGANISM: Homo sapiens

<400> SEQUENCE: 90
agaagaaaaa actttaaacc caccaagta                                            29

<210> SEQ ID NO 91
<211> LENGTH: 87
<212> TYPE: PRT
<213> ORGANISM: Homo sapiens

<400> SEQUENCE: 91

Met Val Gln Ser Cys Ser Ala Tyr Gly Cys Lys Asn Arg Tyr Asp Lys
1               5                   10                  15

Asp Lys Pro Val Ser Phe His Lys Phe Pro Leu Thr Arg Pro Ser Leu
            20                  25                  30

Cys Lys Glu Trp Glu Ala Ala Val Arg Arg Lys Asn Phe Lys Pro Thr
        35                  40                  45

Lys Tyr Ser Ser Ile Cys Ser Glu His Phe Thr Pro Asp Cys Phe Lys
    50                  55                  60

Arg Glu Cys Asn Asn Lys Leu Leu Lys Glu Asn Ala Val Pro Thr Ile
65                  70                  75                  80

Phe Leu Cys Thr Glu Pro His
                85

<210> SEQ ID NO 92
<211> LENGTH: 87
<212> TYPE: PRT
<213> ORGANISM: Canis sp.

<400> SEQUENCE: 92

Met Val Gln Ser Cys Ser Ala Tyr Gly Cys Lys Asn Arg Tyr Asp Lys
1               5                   10                  15

Asp Lys Pro Val Ser Phe His Lys Phe Pro Leu Thr Arg Pro Ser Leu
            20                  25                  30

Cys Lys Lys Trp Glu Ala Ala Val Arg Arg Lys Asn Phe Lys Pro Thr
        35                  40                  45

Lys Tyr Ser Ser Ile Cys Ser Glu His Phe Thr Pro Asp Cys Phe Lys
    50                  55                  60

Arg Glu Cys Asn Asn Lys Leu Leu Lys Glu Asn Ala Val Pro Thr Ile
65                  70                  75                  80

Phe Leu Cys Thr Glu Pro His
                85

<210> SEQ ID NO 93
<211> LENGTH: 87
<212> TYPE: PRT
<213> ORGANISM: Bos sp.

<400> SEQUENCE: 93

Met Val Gln Ser Cys Ser Ala Tyr Gly Cys Lys Asn Arg Tyr Asp Lys
1               5                   10                  15

Asp Lys Pro Val Ser Phe His Lys Phe Pro Leu Thr Arg Pro Ser Leu
            20                  25                  30

Cys Lys Lys Trp Glu Ala Ala Val Arg Arg Lys Asn Phe Lys Pro Thr
        35                  40                  45

```
Lys Tyr Ser Ser Ile Cys Ser Glu His Phe Thr Pro Asp Cys Phe Lys
 50                  55                  60

Arg Glu Cys Asn Asn Lys Leu Leu Lys Glu Asp Ala Val Pro Thr Ile
 65                  70                  75                  80

Phe Leu Cys Thr Glu Pro His
                 85

<210> SEQ ID NO 94
<211> LENGTH: 87
<212> TYPE: PRT
<213> ORGANISM: Mus sp.

<400> SEQUENCE: 94

Met Val Gln Ser Cys Ser Ala Tyr Gly Cys Lys Asn Arg Tyr Asp Lys
 1               5                  10                  15

Asp Lys Pro Val Ser Phe His Lys Phe Pro Leu Thr Arg Pro Ser Leu
                20                  25                  30

Cys Lys Gln Trp Glu Ala Ala Val Lys Arg Lys Asn Phe Lys Pro Thr
            35                  40                  45

Lys Tyr Ser Ser Ile Cys Ser Glu His Phe Thr Pro Asp Cys Phe Lys
 50                  55                  60

Arg Glu Cys Asn Asn Lys Leu Leu Lys Glu Asn Ala Val Pro Thr Ile
 65                  70                  75                  80

Phe Leu Tyr Ile Glu Pro His
                 85

<210> SEQ ID NO 95
<211> LENGTH: 87
<212> TYPE: PRT
<213> ORGANISM: Rattus sp.

<400> SEQUENCE: 95

Met Val Gln Ser Cys Ser Ala Tyr Gly Cys Lys Asn Arg Tyr Asp Lys
 1               5                  10                  15

Asp Lys Pro Val Ser Phe His Lys Phe Pro Leu Thr Arg Pro Ser Leu
                20                  25                  30

Cys Lys Gln Trp Glu Ala Ala Val Arg Arg Lys Asn Phe Lys Pro Thr
            35                  40                  45

Lys Tyr Ser Ser Ile Cys Ser Glu His Phe Thr Pro Asp Cys Phe Lys
 50                  55                  60

Arg Glu Cys Asn Asn Lys Leu Leu Lys Glu Asn Ala Val Pro Thr Ile
 65                  70                  75                  80

Phe Leu Tyr Ile Glu Pro His
                 85

<210> SEQ ID NO 96
<211> LENGTH: 87
<212> TYPE: PRT
<213> ORGANISM: Gallus sp.

<400> SEQUENCE: 96

Met Val Gln Ser Cys Ser Ala Tyr Arg Cys Arg Asn Arg Tyr Asp Lys
 1               5                  10                  15

Glu Lys Pro Ile Ser Phe His Lys Phe Pro Leu Thr Arg Pro Asp Leu
                20                  25                  30

Cys Lys Lys Trp Glu Ala Ala Val Lys Arg Lys Asn Phe Lys Pro Thr
            35                  40                  45

Lys Tyr Ser Ser Ile Cys Ser Glu His Phe Thr Pro Asp Cys Phe Lys
 50                  55                  60
```

```
Arg Glu Cys Asn Asn Lys Leu Leu Lys Glu Asn Ala Val Pro Thr Ile
 65                  70                  75                  80

Phe Cys Tyr Thr Glu Pro Ser
                85

<210> SEQ ID NO 97
<211> LENGTH: 82
<212> TYPE: PRT
<213> ORGANISM: Danio rerio

<400> SEQUENCE: 97

Met Val Gln Ser Cys Ser Ala Tyr Gly Cys Lys Asn Arg Tyr Gln Lys
 1               5                  10                  15

Asp Arg Asn Ile Ser Phe His Lys Phe Pro Leu Ala Arg Pro Glu Val
                20                  25                  30

Cys Val Gln Trp Val Ser Ala Met Ser Arg Arg Asn Phe Lys Pro Thr
            35                  40                  45

Lys Tyr Ser Asn Ile Cys Ser Gln His Phe Thr Ser Asp Cys Phe Lys
    50                  55                  60

Gln Glu Cys Asn Asn Arg Val Leu Lys Asp Asn Ala Val Pro Ser Leu
 65                  70                  75                  80

Phe Thr

<210> SEQ ID NO 98
<211> LENGTH: 87
<212> TYPE: PRT
<213> ORGANISM: Xenopus sp.

<400> SEQUENCE: 98

Met Val Gln Ser Cys Ser Ala Tyr Gly Cys Lys Asn Arg Tyr Asp Lys
 1               5                  10                  15

Asp Arg Pro Ile Ser Phe His Lys Phe Pro Leu Lys Arg Pro Leu Leu
                20                  25                  30

Cys Lys Lys Trp Glu Ala Ala Val Arg Arg Ala Asp Phe Lys Pro Thr
            35                  40                  45

Lys Tyr Ser Ser Ile Cys Ser Asp His Phe Thr Ala Asp Cys Phe Lys
    50                  55                  60

Arg Glu Cys Asn Asn Lys Leu Leu Lys Asp Asn Ala Val Pro Thr Val
 65                  70                  75                  80

Phe Ala Leu Ala Glu Ile Lys
                85

<210> SEQ ID NO 99
<211> LENGTH: 86
<212> TYPE: PRT
<213> ORGANISM: Homo sapiens

<400> SEQUENCE: 99

Met Pro Thr Asn Cys Ala Ala Gly Cys Ala Thr Thr Tyr Asn Lys
 1               5                  10                  15

His Ile Asn Ile Ser Phe His Arg Phe Pro Leu Asp Pro Lys Arg Arg
                20                  25                  30

Lys Glu Trp Val Arg Leu Val Arg Arg Lys Asn Phe Val Pro Gly Lys
            35                  40                  45

His Thr Phe Leu Cys Ser Lys His Phe Glu Ala Ser Cys Phe Asp Leu
    50                  55                  60

Thr Gly Gln Thr Arg Arg Leu Lys Met Asp Ala Val Pro Thr Ile Phe
 65                  70                  75                  80
```

Asp Phe Cys Thr His Ile
                85

<210> SEQ ID NO 100
<211> LENGTH: 88
<212> TYPE: PRT
<213> ORGANISM: Homo sapiens

<400> SEQUENCE: 100

Met Pro Lys Ser Cys Ala Ala Arg Gln Cys Cys Asn Arg Tyr Ser Ser
1               5                   10                  15

Arg Arg Lys Gln Leu Thr Phe His Arg Phe Pro Phe Ser Arg Pro Glu
            20                  25                  30

Leu Leu Lys Glu Trp Val Leu Asn Ile Gly Arg Gly Asn Phe Lys Pro
        35                  40                  45

Lys Gln His Thr Val Ile Cys Ser Glu His Phe Arg Pro Glu Cys Phe
    50                  55                  60

Ser Ala Phe Gly Asn Arg Lys Asn Leu Lys His Asn Ala Val Pro Thr
65                  70                  75                  80

Val Phe Ala Phe Gln Asp Pro Thr
                85

<210> SEQ ID NO 101
<211> LENGTH: 91
<212> TYPE: PRT
<213> ORGANISM: Homo sapiens

<400> SEQUENCE: 101

Met Val Ile Cys Cys Ala Ala Val Asn Cys Ser Asn Arg Gln Gly Lys
1               5                   10                  15

Gly Glu Lys Arg Ala Val Ser Phe His Arg Phe Pro Leu Lys Asp Ser
            20                  25                  30

Lys Arg Leu Ile Gln Trp Leu Lys Ala Val Gln Arg Asp Asn Trp Thr
        35                  40                  45

Pro Thr Lys Tyr Ser Phe Leu Cys Ser Glu His Phe Thr Lys Asp Ser
    50                  55                  60

Phe Ser Lys Arg Leu Glu Asp Gln His Arg Leu Leu Lys Pro Thr Ala
65                  70                  75                  80

Val Pro Ser Ile Phe His Leu Thr Glu Lys Lys
                85                  90

<210> SEQ ID NO 102
<211> LENGTH: 95
<212> TYPE: PRT
<213> ORGANISM: Homo sapiens

<400> SEQUENCE: 102

Met Val Lys Cys Cys Ser Ala Ile Gly Cys Ala Ser Arg Cys Leu Pro
1               5                   10                  15

Asn Ser Lys Leu Lys Gly Leu Thr Phe His Val Phe Pro Thr Asp Glu
            20                  25                  30

Asn Ile Lys Arg Lys Trp Val Leu Ala Met Lys Arg Leu Asp Val Asn
        35                  40                  45

Ala Ala Gly Ile Trp Glu Pro Lys Gly Asp Val Leu Cys Ser Arg
    50                  55                  60

His Phe Lys Lys Thr Asp Phe Asp Arg Ser Ala Pro Asn Ile Lys Leu
65                  70                  75                  80

Lys Pro Gly Val Ile Pro Ser Ile Phe Asp Ser Pro Tyr His Leu

```
                85                  90                  95

<210> SEQ ID NO 103
<211> LENGTH: 99
<212> TYPE: PRT
<213> ORGANISM: Homo sapiens

<400> SEQUENCE: 103

Met Pro Arg His Cys Ser Ala Ala Gly Cys Cys Thr Arg Asp Thr Arg
1               5                   10                  15

Glu Thr Arg Asn Arg Gly Ile Ser Phe His Arg Leu Pro Lys Lys Asp
            20                  25                  30

Asn Pro Arg Arg Gly Leu Trp Leu Ala Asn Cys Gln Arg Leu Asp Pro
        35                  40                  45

Ser Gly Gln Gly Leu Trp Asp Pro Ala Ser Glu Tyr Ile Tyr Phe Cys
    50                  55                  60

Ser Lys His Phe Glu Glu Asp Cys Phe Glu Leu Val Gly Ile Ser Gly
65                  70                  75                  80

Tyr His Arg Leu Lys Glu Gly Ala Val Pro Thr Ile Phe Glu Ser Phe
                85                  90                  95

Ser Lys Leu

<210> SEQ ID NO 104
<211> LENGTH: 91
<212> TYPE: PRT
<213> ORGANISM: Homo sapiens

<400> SEQUENCE: 104

Met Pro Lys Tyr Cys Arg Ala Pro Asn Cys Ser Asn Thr Ala Gly Arg
1               5                   10                  15

Leu Gly Ala Asp Asn Arg Pro Val Ser Phe Tyr Lys Phe Pro Leu Lys
            20                  25                  30

Asp Gly Pro Arg Leu Gln Ala Trp Leu Gln His Met Gly Cys Glu His
        35                  40                  45

Trp Val Pro Ser Cys His Gln His Leu Cys Ser Glu His Phe Thr Pro
    50                  55                  60

Ser Cys Phe Gln Trp Arg Trp Gly Val Arg Tyr Leu Arg Pro Asp Ala
65                  70                  75                  80

Val Pro Ser Ile Phe Ser Arg Gly Pro Pro Ala
                85                  90

<210> SEQ ID NO 105
<211> LENGTH: 95
<212> TYPE: PRT
<213> ORGANISM: Homo sapiens

<400> SEQUENCE: 105

Met Thr Arg Ser Cys Ser Ala Val Gly Cys Ser Thr Arg Asp Thr Val
1               5                   10                  15

Leu Ser Arg Glu Arg Gly Leu Ser Phe His Gln Phe Pro Thr Asp Thr
            20                  25                  30

Ile Gln Arg Ser Lys Trp Ile Arg Ala Val Asn Arg Val Asp Pro Arg
        35                  40                  45

Ser Lys Lys Ile Trp Ile Pro Gly Pro Gly Ala Ile Leu Cys Ser Lys
    50                  55                  60

His Phe Gln Glu Ser Asp Phe Glu Ser Tyr Gly Ile Arg Arg Lys Leu
65                  70                  75                  80

Lys Lys Gly Ala Val Pro Ser Val Ser Leu Tyr Lys Ile Pro Gln
```

```
<210> SEQ ID NO 106
<211> LENGTH: 96
<212> TYPE: PRT
<213> ORGANISM: Homo sapiens

<400> SEQUENCE: 106

Met Pro Ala Arg Cys Val Ala Ala His Cys Gly Asn Thr Thr Lys Ser
1               5                   10                  15

Gly Lys Ser Leu Phe Arg Phe Pro Lys Asp Arg Ala Val Arg Leu Leu
            20                  25                  30

Trp Asp Arg Phe Val Arg Gly Cys Arg Ala Asp Trp Tyr Gly Gly Asn
        35                  40                  45

Asp Arg Ser Val Ile Cys Ser Asp His Phe Ala Pro Ala Cys Phe Asp
    50                  55                  60

Val Ser Ser Val Ile Gln Lys Asn Leu Arg Phe Ser Gln Arg Leu Arg
65                  70                  75                  80

Leu Val Ala Gly Ala Val Pro Thr Leu His Arg Val Pro Ala Pro Ala
                85                  90                  95

<210> SEQ ID NO 107
<211> LENGTH: 106
<212> TYPE: PRT
<213> ORGANISM: Homo sapiens

<400> SEQUENCE: 107

Met Pro Gly Phe Thr Cys Cys Val Pro Gly Cys Tyr Asn Asn Ser His
1               5                   10                  15

Arg Asp Lys Ala Leu His Phe Tyr Thr Phe Pro Lys Asp Ala Glu Leu
            20                  25                  30

Arg Arg Leu Trp Leu Lys Asn Val Ser Arg Ala Gly Val Ser Gly Cys
        35                  40                  45

Phe Ser Thr Phe Gln Pro Thr Thr Gly His Arg Leu Cys Ser Val His
    50                  55                  60

Phe Gln Gly Gly Arg Lys Thr Tyr Thr Val Arg Val Pro Thr Ile Phe
65                  70                  75                  80

Pro Leu Arg Gly Val Asn Glu Arg Lys Val Ala Arg Arg Pro Ala Gly
                85                  90                  95

Ala Ala Ala Ala Arg Arg Arg Gln Gln Gln
                100                 105
```